United States Patent [19]
Cai et al.

[11] Patent Number: 5,358,938
[45] Date of Patent: Oct. 25, 1994

[54] COMPOUNDS AND METHODS FOR THE TREATMENT OF DISORDERS MEDIATED BY PLATELET ACTIVATING FACTOR OR PRODUCTS OF 5-LIPOXYGENASE

[75] Inventors: Xiong Cai, Allston; Saijat Hussoin, Cambridge; San-Bao Hwang, Wayland; David Killian, Cambridge, all of Mass.; T. Y. Shen, Charlottesville, Va.

[73] Assignee: CytoMed, Inc., Cambridge, Mass.

[21] Appl. No.: 912,788

[22] Filed: Jul. 13, 1992

[51] Int. Cl.$^5$ .................. A61K 31/535; H01N 43/40; C07D 333/22; C07D 413/00

[52] U.S. Cl. .................. 514/231.5; 514/237.2; 514/333; 514/337; 514/438; 514/448; 514/471; 514/473; 544/124; 544/146; 544/152; 546/256; 546/283; 546/284; 549/62; 549/66; 549/67; 549/68; 549/70; 549/71; 549/72; 549/73; 549/74; 549/75; 549/77; 549/78; 549/79; 549/80; 549/473; 549/475; 549/476; 549/477; 549/478; 549/480; 549/483; 549/484; 549/487; 549/488; 549/491; 549/492; 549/494; 549/496; 549/497; 549/498; 549/499; 549/500; 549/501; 549/502

[58] Field of Search .................. 549/77, 62, 63, 64, 549/65, 66, 67, 68, 70, 71, 72, 73, 74, 75, 78, 79, 80, 473, 475, 476, 477, 478, 480, 483, 484, 487, 488, 491, 492, 494, 495, 496, 497, 498, 499, 500, 501, 502; 544/124, 146, 152; 546/256, 283, 284; 514/231.5, 237.2, 333, 337, 438, 445, 448, 471, 472, 473

[56] References Cited

U.S. PATENT DOCUMENTS

| | | | |
|---|---|---|---|
| 4,539,332 | 9/1985 | Biftu et al. | 514/461 |
| 4,757,084 | 7/1988 | Biftu et al. | 514/438 |
| 4,910,206 | 3/1990 | Houlihan | 514/292 |
| 4,916,145 | 4/1990 | Tilley et al. | 514/357 |
| 4,959,361 | 9/1990 | Walser | 514/220 |
| 4,987,132 | 1/1991 | Mase et al. | 514/252 |
| 4,992,428 | 2/1991 | Houlihan et al. | 514/63 |
| 4,996,203 | 2/1991 | Biftu et al. | 514/231.5 |
| 5,001,123 | 3/1991 | Biftu et al. | 514/235.2 |

FOREIGN PATENT DOCUMENTS

| | | |
|---|---|---|
| 0144804A | 6/1985 | European Pat. Off. . |
| 0199324 | 10/1986 | European Pat. Off. . |
| 0217204 | 4/1987 | European Pat. Off. . |
| 0322033 | 12/1987 | European Pat. Off. . |
| 0252823A1 | 1/1988 | European Pat. Off. . |
| 0319947A2 | 6/1989 | European Pat. Off. . |
| 0338993A1 | 10/1989 | European Pat. Off. . |
| 0365089A2 | 4/1990 | European Pat. Off. . |

(List continued on next page.)

OTHER PUBLICATIONS

Biftu, T., et al., "Confirmation and Activity of Tetrahydrofuran Lignans and Analogues as Specific Platelet Activating Factor Antagonists," *J. Med. Chem.* vol. 29, No. 10 (1986) pp. 1917–1921.

Corey, E. J., et al., "Dual Binding Modes to the Recep- (List continued on next page.)

*Primary Examiner*—C. Warren Ivy
*Assistant Examiner*—Raymond Covington
*Attorney, Agent, or Firm*—Kilpatrick & Cody

[57] ABSTRACT

2,5-Diaryl tetrahydrofurans, 2,5-diaryl terahydrothiophenes, 2,4-diaryl tetrahydrofurans, 2,4-diaryl tetrahydrothiphenes, 1,3-diaryl cyclopentanes, 2,4-diaryl pyrrolidines, and 2,5-diaryl pyrrolidines are disclosed that reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase.

A method to treat disorders mediated by PAF or leukotrienes is also disclosed, that includes administering an effective amount of one or more of the above-identified compounds or a pharmaceutically acceptable salt thereof, optionally in a pharmaceutically acceptable carrier.

25 Claims, 12 Drawing Sheets

FOREIGN PATENT DOCUMENTS

| | | |
|---|---|---|
| 0367110A1 | 5/1990 | European Pat. Off. . |
| 0388309A2 | 9/1990 | European Pat. Off. . |
| 0402150A1 | 12/1990 | European Pat. Off. . |
| 0402151A1 | 12/1990 | European Pat. Off. . |
| 0402155 | 12/1990 | European Pat. Off. . |
| 0402156 | 12/1990 | European Pat. Off. . |
| 0416609A2 | 3/1991 | European Pat. Off. . |
| 3701344A1 | 7/1987 | Fed. Rep. of Germany . |
| 3724031A1 | 7/1987 | Fed. Rep. of Germany . |
| 3724164A1 | 7/1987 | Fed. Rep. of Germany . |
| 3936828A1 | 5/1990 | Fed. Rep. of Germany . |
| 4006471A1 | 9/1990 | Fed. Rep. of Germany . |
| WO90/12015 | of 0000 | PCT Int'l Appl. . |
| WO92/15294 | 9/1992 | PCT Int'l Appl. . |
| 2197650A | 5/1988 | United Kingdom . |
| 2233974A | 1/1991 | United Kingdom . |
| WO92/09566 | 6/1992 | WIPO . |

OTHER PUBLICATIONS tor for Platelet Activating Factor (PAF) of Anti-PAF Trans-2,5-Diarylfurans," *Tetrahedron Letters*, vol. 29, No. 24 (1988) pp. 2899-2902.

Ponpipom, M. M., et al., "(±)-Trans-2-(3-Methylsulfonyl-4-Propoxyphenyl)-5-(3,4,5-Trimethoxyyphenyl)Tetrahydrofuran (L-659,989), A Novel Potent PAF Receptor Antagnonist," *Biochemical and Biophysical Research Communications*, vol. 150, No. 3 (1988) pp. 1213-1220.

Bartroli, J. *J. Med. Chem.* vol. 34 (1991) pp. 3328-3334.

Carlcellar, E., et al., *J. Med. Chem.*, vol. 35 (1992) pp. 676-683.

Crawley, G. C., "Methoxytetrahydropyrans, A New Series of Selective and Orally Potent 5-Lipoxygenase Inhibitors," *J. Med. Chem.*, vol. 35, No. 14 (1992) pp. 2600-2609.

Musser, J. H., et al., "5-Lipoxygenase: Properties, Pharmacology, and the Quinolinyl(bridge)aryl Class of Inhibitors," *J. Med. Chem.*, vol. 35, No. 14 (1992) pp. 2502-2524.

Guthrie, R. W., et al., "Propenyl Carboxamide Derivatives As Antagonists of Platelet Activating Factor," *J. Med. Chem.*, vol. 33 (1990) pp. 2856-2864.

Graham, D. W., et al., "1,3-Diarylcyclopentanes: A New Class Potent Receptor Antagonists," MEDI (1990).

Lave, D. et al., "Pyrrolo[1,2-c]Thiazole Derivatives: Potent PAF Receptor Antagonists" *Drugs of the Future*, vol. 14, No. 9 (1989) pp. 891-898.

Ogiso, A., et al., "The Structure of Futoenone, A Novel Spiro-Cyclohexadienone Derivative," *Tetrahedron Letters*, No. 16, (1968) pp. 2003-2008.

Ogiso, A., et al., "The Structure and Total Synthesis of Futoenone, a Constitute of *Piper futokadzura* SIEB, et ZUCC.", *Chem. Pharm. Bull.*, vol. 18, No. 1, (1970) pp. 105-114.

Ponpipom, M. M., et al., "Structure-Activity Relationships of Kadsurenone Analogues," *J. Med. Chem.*, vol. 30 (1987) pp. 136-142.

Shen, T. Y., "Characterization of a Platelet-Activating Factor Receptor Isolated from Halifenteng (*Piper futokadsura*): Specific Inhibition of *in vito* and *in vivo* Platelet-Activating Factor-Induced Effects," *Proc. Natl. Acad. Sci. USA*, vol. 82, (Feb. 1985) pp. 672-676.

Weber, K. H., et al., "Hetrazepines as Antagonists of Platelet Activating Factor," *Medicinal Research Reviews*, vol. 9, No. 1 (Jan.-Mar. 1989) pp. 181-218.

Feinmark, S. J., "Leukotriene C, Biosynthesis during Polymorphonuclear Leukocyte-Vascular Cell Interactions," *Methods in Enzymology*, vol. 187, pp. 559-560 (1990).

Hwang, S., "Specific Receptors of Platelet-Activating Factor, Receptor Heterogeneity, and Signal Transduction Mechanisms," *J. Lipid Mediators*, vol. 2 (1990) pp. 123-158.

McColl, S. R., "Determination of 5-Lipoxygenase Activity Human Polymorphonuclear Leukocytes Using High-Performance Liquid Chromatography," *J. Chromatography*, vol. 378 (1986) pp. 44-449.

O'Donnell, M., et al., "Comparison of the Pulmonary Pharmacology of Leukotrienes and PAF; Effects of their Antagonists," *Therapeutic Approaches to Inflammatory Diseases* Proceedings of the Fourth International Conference of the Inflammatory Research Association, Oct. 23-27, 1988, White Haven, Pa., p. 169.

Page, C., et al., "PAF; New Antagonists, New Rules in Diseases and a Major Role in Reproductive Biology," *3rd International Conference on Platelet-Activating Factor and Structurally Related Alkyl Ether Lipids*, Tokyo, Japan, May 8-12, 1989.

Shen, T. Y. et al., "The Chemical and Biological Properties of PAF Agonists, Antagonists, and Biosynthetic Inhibitors," *Platelet-Activating Factor and Related Lipid Mediators*, Plenum Press, New York, N.Y., pp. 153-190 (1987).

| | | | | |
|---|---|---|---|---|
| X=O, Z=CH₂CH₂CH₃ | Y=CH₂Ph | Y'=H | | 3 |
| X=O, Z=CH₂CH₂CH₃ | Y=CH₂CH₂OH | Y'=H | | 4 |
| X=O, Z=CH₂CH₂CH₃ | Y=CH2CH=CH2 | Y'=CH₂CH=CH₂ | | 5 |
| X=S, Z=CH₂CH₂CH₃ | Y=CH₂Ph | Y'=H | | 7 |
| X=S, Z=CH₂CH₂CH₃ | Y=CH₂CH₂CH | Y'=H | | 9 |
| X=S, Z=CH₂CH₂CH₃ | Y=CH₂CH=CH₂ | Y'=CH₂CH=CH₂ | | 11 |
| X=S, Z=CH₃ | Y=CH₂Ph | Y'=H | | 6 |
| X=S, Z=CH₃ | Y=CH₂CH₂OH | Y'=H | | 8 |
| X=S, Z=CH₃ | Y=CH2CH=CH | Y'=CH₂CH=CH₂ | | 10 |
| X=O,S; Z=CH₂CH₂CH₃ | Y=CONAOH | Y'=H  A=H, alkyls | | 12-32 38-41 |

COMPOUNDS AND METHODS FOR THE TREATMENT OF DISORDERS MEDIATED BY PLATELET ACTIVATING FACTOR OR PRODUCTS OF 5-LIPOXYGENASE

BACKGROUND OF THE INVENTION

This invention is in the area of pharmaceutical compositions and methods for the treatment of inflammatory and immune disorders, and specifically provides novel compounds that reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase.

Platelet activating factor (PAF, 1-O-alkyl-2-acetyl-sn-glycerol-3-phosphorylcholine) is a potent inflammatory phospholipid mediator with a wide variety of biological activities. PAF was initially identified as a water soluble compound released by immunoglobulin E (IgE)-sensitized rabbit basophils. It is now known that PAF is also generated and released by monocytes, macrophages, polymorphonuclear leukocytes (PMNs), eosinophils, neutrophils, natural killer lymphocytes, platelets and endothelial cells, as well as by renal and cardiac tissues under appropriate immunological and non-immunological stimulation. (Hwang, "Specific receptors of platelet-activating factor, receptor heterogeneity, and signal transduction mechanisms", *Journal of Lipid Mediators* 2, 123 (1990)). PAF causes the aggregation and degranulation of platelets at very low concentrations. The potency (active at $10^{-12}$ to $10^{-9}$M), tissue level (picomoles) and short plasma half life (2-4 minutes) of PAF are similar to those of other lipid mediators such as thromboxane $A_2$, prostaglandins, and leukotrienes.

PAF mediates biological responses by binding to specific PAF receptors found in a wide variety of cells and tissues. Structure-activity studies on PAF and its analogs indicate that the ability of PAF to bind to these receptors is highly structure specific and stereospecific. (Shen, et al., "The Chemical and Biological Properties of PAF Agonists, Antagonists, and Biosynthetic Inhibitors", *Platelet-Activating Factor and Related Lipid Mediators*, F. Snyder, Ed. Plenum Press, New York, N.Y. 153 (1987)).

While PAF mediates essential biological responses, it also appears to play a role in pathological immune and inflammatory responses. Many published studies have provided evidence for the involvement of PAF in human diseases, including arthritis, acute inflammation, asthma, endotoxic shock, pain, psoriasis, ophthalmic inflammation, ischemia, gastrointestinal ulceration, myocardial infarction, inflammatory bowel diseases, and acute respiratory distress syndrome. Animal models also demonstrate that PAF is produced or increased in certain pathological states.

The involvement of PAF in pathological inflammatory and immune states has stimulated a substantial research effort to identify PAF receptor antagonists. In 1983, a phospholipid analog referred to as CV-3998 (rac-3-(N-n-octadecyl-carbamoyloxy-ω-methoxypropyl-2-thiazolioethyl phosphate) was reported to have PAF receptor antagonist properties. (Terashita, et al., *Life Sciences* 32, 1975 (1983).) In other early work in this area, Shen, et al., (in *Proc. Natl. Acad. Sci. (U.S.A.)* 82, 672 (1985)), reported that kadsurenone, a neolignan derivative isolated from Piper futokadsura Sieb et Zucc (a Chinese herbal plant) was a potent, specific and competitive inhibitor of PAF activity at the receptor level.

Hwang, et al., disclosed in 1985 that trans-2,5-bis-(3,4-trimethoxyphenyl)tetrahydrofuan (L-652,731) inhibits the binding of tritiated PAF to PAF receptor sizes. (Hwang, et al., "Trans-2,5-bis-(3,4,5-trimethoxyphenyl)tetrahydrofuran", *Journal of Biological Chemistry* 260, 15639 (1985).) L-652,731 was found to be orally active, and to inhibit PAF-induced rat cutaneous vascular permeability at a dosage of 30 mg/kg body weight. The compound was found to have no effect on the enzyme 5-lipoxygenase. Hwang, et al. also reported that trans-L-652,731 (wherein the aryl groups at the 2 and 5 positions are on opposite sides of the plane of the tetrahydrofuran ring) is approximately 1000 times more potent than cis-L-652,731 (wherein the 2 and 5 aryl substituents are on the same side of the plane of the tetrahydrofuran ring).

In 1988, Hwang, et al., reported that L-659,989 (trans-2-(3-methoxy-4-propoxyphenyl-5-methylsulfonyl)-5-(3,4,5-trimethoxyphenyl)tetrahydrofuran) is an orally active, potent, competitive PAF receptor antagonist, with an equilibrium inhibition constant 10 times greater than that of trans-L-652,731. (Hwang, et al., *J. Pharmacol. Ther.* 246, 534 (1988).)

U.S. Pat. No. 4,996,203, 5,001,123 and 4,539,332 to Biftu et al. and European Patent Application Nos. 89202593.3, 90306235.4, and 90306234.7 disclose that a specific class of 2,5-diaryl tetrahydrofurans are PAF receptor antagonists.

Leukotrienes, like PAF, are potent local mediators, playing a major role in inflammatory and allergic responses, including arthritis, asthma, psoriasis, and thrombotic disease. Leukotrienes are straight chain eicosanoids produced by the oxidation of arachidonic acid by lipoxygenases. Arachidonic acid is oxidized by 5-lipoxygenase to the hydroperoxide 5-hydroxyperoxyeicosatetraenoic acid (5-HPETE), that is converted to leukotriene $A_4$, that in turn can be converted to leukotriene $B_4$, $C_4$, or $D_4$. The slow-reacting substance of anaphylaxis is now known to be a mixture of leukotrienes $C_4$, $D_4$, and $E_4$, all of which are potent bronchoconstrictors. There has been a research effort to develop specific receptor antagonists or inhibitors of leukotriene biosynthesis, to prevent or minimize pathogenic inflammatory responses mediated by these compounds.

Leukotrienes are released simultaneously from leukocytes with PAF, possibly from a common phospholipid precursors such as 1-O-hexadecyl-2-arachidonyl-sn-glycerophosphocholine, and upon cellular activation, act synergistically with PAF in many biological models. Recently, it was reported that the tetrahydrothiphene derivative of L-652,731, trans-2,5-bis-(3,4,5-trimethoxyphenyl)tetrahydrothiophene (L-653,150), is a potent PAF antagonist and a moderate inhibitor of 5-lipoxygenase. It has been disclosed that certain 2,5-diaryl tetrahydrothiophenes are PAF antagonists and leukotriene synthesis inhibitors (Biftu, et al., *Abstr. of 6th Int. Conf. on Prostaglandins and Related Compounds*, Jun. 3-6, 1986, Florence, Italy, U.S. Pat. No. 4,757,084 to Biftu)

Given the significant number of pathological immune and inflammatory responses that are mediated by PAF and leukotrienes, there remains a need to identify new compounds and compositions that exhibit PAF receptor antagonistic activity or inhibit the enzyme 5-lipoxygenase. European Patent Application Nos. 90117171.0 and 901170171.0 disclose indole, benzofuran, and benzothiphene lipoxygenase inhibiting compounds.

Therefore, it is an object of the present invention to provide compounds that reduce the chemotaxis and respiratory burst leading to the formation of damaging oxygen radicals during an inflammatory or immune response.

It is another object of the present invention to provide pharmaceutical compositions for the treatment of pathological immune or inflammatory disorders mediated by PAF or products of 5-lipoxygenase.

It is another object of the present invention to provide a method for the treatment of pathological immune or inflammatory disorders mediated by PAF or products of 5-lipoxygenase.

SUMMARY OF THE INVENTION 2,5-Diaryl tetrahydrothiophenes, tetrahydrofurans, and pyrrolidines, 1,3-diaryl cyclopentanes, and 2,4-diaryl tetrahydrothiophenes, tetrahydrofurans and pyrrolidines are disclosed of the structures:

Formula I $$Ar^1 \underset{X}{\overset{R^1 \quad R^2}{\diagdown \diagup}} Ar^2$$

wherein:

$Ar^1$ = [phenyl with $W_n$, $W_n$ substituents and $Y$ (m)] or [pyridyl N-containing ring with $Y_n$, $W_n$ substituents]

$Ar^2$ = [phenyl with $W_p$, $Y_m$ substituents] or [pyridyl N-containing ring with $W_p$, $Y_n$ substituents]

wherein:

X is O, S, S(O), S(O)$_2$, CR$^9$, or NR$^{10}$;

W is independently —AN(OM)C(O)N(R$^3$)R$^4$, —AN(R$^3$)C(O)N(OM)R$^4$, —AN(OM)C(O)R$^4$, —AC(O)N(OM)R$^4$, —N(OM)C(O)N(R$^3$)R$^4$, —N(R$^3$)C(O)N(OM)R$^4$, —N(OM)C(O)R$^4$, —C(O)N(OM)R$^4$, —OR$^6$N(R$^5$)R$^6$—(C$_5$H$_4$N)R$^6$R$^7$, —OR$^6$N(COR$^5$)-R$^6$—(C$_5$H$_4$N)R$^6$R$^7$, —OR$^6$OC(O)N(COR$^5$)-R$^6$—(C$_5$H$_4$N)R$^6$R$^7$, —OR$^6$O(CO)N-(CO$_2$R$^6$)R$^6$(C$_5$H$_4$N)R$^6$R$^7$, —A(C$_5$H$_4$N)R$^6$R$^7$, or —A(C$_5$H$_4$N)R$^6$R$^7$;

n is 1 or 2;

m is 1, 2 or 3;

p is 0 or 1;

A is alkyl, alkenyl, alkynyl, alkyaryl, aralkyl, halo lower alkyl, halo lower alkyl, halo lower alkynyl, —C$^{1-10}$alkyl(oxy)C$^{1-10}$alkyl, —C$^{1-10}$alkyl(thio)C$^{1-10}$alkyl, —N(R$^3$)C(O)alkyl, —N(R$^3$)C(O)alkenyl, —N(R$^3$)C(O)alkynyl, —N(R$^3$)C(O)(alkyl)oxy(alkyl), —N(R$^3$)C(O)(alkyl)thio (alkyl), —N(R$^3$)C(O)N(alkyl), —N(R$^3$)C(O)N(alkenyl), —N(R$^3$)C(O)N(alkynyl), —N(R$^3$)C(O)N(alkyl)oxy(alkyl), —N(R$^3$)C(O)N(alkyl)thio(alkyl), —N(R$^3$)C(O$_2$)alkyl, —N(R$^3$)C(O$_2$)alkenyl, —N(R$^3$)C($_2$)alkynyl, —N(R$^3$)C(O$_2$)(alkyl)oxy(alkyl), —N(R$^3$)C(O$_2$)(alkyl)thio(alkyl), —OC(O$_2$)alkyl, —OC(O$_2$)alkyl, —OC(O$_2$)alkenyl, —OC(O$_2$)alkynyl, —OC(O$_2$)(alkyl)oxy(alkyl), —OC(O$_2$)(alkyl)thio(alkyl), —N(R$^3$)C(S)alkyl, —N(R$^3$)C(S)alkenyl, —N(R$^3$)C(S)alkynyl, —N(R$^3$C(S)(alkyl)oxy(alkyl), —N(R$^3$)C(S)(alkyl)thio(alkyl), —N(R$^3$)C(S)N(alkyl), —N(R$^3$)C(S)N(alkenyl), —N(R$^3$)C(S)N(alkynyl), —N(R$^3$)C(S)N(alkyl)oxy(alkyl), —N(R$^3$)C(S)N(alyl)thio(alkyl), —N(R$^3$)C(S)S(alkyl), —N(R$^3$)C(S)S(alkenyl), —N(R$^3$)C(S)S(alkynyl), —N(R$^3$)C(S)S(alkyl)oxy(alkyl), —N(R$^3$)C(S)S(alkyl)thio(alkyl), —SC(S)S(alkyl), —SC(S)S(alkenyl), —SC(S)S(alkynyl), —SC(S)S(alkyl)oxy(alkyl), and —SC(S)S(alkyl)thio(alkyl);

M is hydrogen, a pharmaceutically acceptable cation, or a metabolically cleavable leaving group;

Y is independently:

(a) hydrogen;

(b) R$^{1-6}$, R$^8$, R$^{10}$, —OR$^3$, —OR$^{11}$, —OR$^{12}$, R$^3$S—, R$^5$S—, R$^3$SO—, R$^5$SO—, R$^3$SO$_2$—, R$^5$SO$_2$—, CF$_3$O—, CF$_3$S—, CF$_3$SO$_2$, —OCH$_2$oxycyclopropyl, —OCH$_2$C(O)OR$^3$, —OCH$_2$OR$^3$, —OCH$_2$C(O)R$^3$, —OCH$_2$C$_3$-$_8$cycloalkyl, —OCH$_2$CH(R)R$^3$, —OCH$_2$cyclopropyl, —OCH$_2$-aryl, —OCH$_2$CH(OH)CH$_2$OH, aryl-CH$_2$—SO$_2$—, (R$^3$)$_2$CHCH$_2$SO$_2$—, —CH$_2$CH(OH)C-H$_2$OH, CF$_3$SO$_2$—, R$^3$R$^4$N—, —OCH$_2$CO$_2$R$^3$, —NR$^3$COR$^3$, —OCONH$_2$, —OCONR$^2$R$^4$, —CONH$_2$, —CONR$^3$R$^4$, —CR$^3$R$^3$R$^4$, —SO$_2$NR$^3$R$^4$, —SONR$^3$R$^4$, —CH$_3$OCH$_2$NR$^3$R$^6$, —SNR$^3$R$^4$, —CO$_2$R$^3$, —NR$^3$R$^4$SO$_2$R$^3$, —NR$^3$R$^4$SOR, —COR$^3$, —CONR$^3$, —NO$_2$, —CN, —N(R$^5$)CONR$^3$R$^4$, —CH$_2$N(R$^5$)CONR$^3$R$^4$, —R$^6$NR$^3$R$^4$, —OR$^6$NR$^3$R$^4$, —O(O)CR$^5$, —O-(O)CNR$^3$R$^4$,

—OR$^6$N⟨ ⟩O,

—SR$^6$NR$^3$R$^4$, —S(O)R$^6$NR$^3$R$^4$, —SO$_2$R$^6$NR$^3$R$^4$,

—SO$_2$OR$^6$CON⟨ ⟩O,

—SR$^6$OH, —S(O)R$^6$OH, —SO$_2$R$^6$OH, —OR$^6$OC-(O)N(CO$_2$R$^6$)R$^6$;

(c) a heterocycle, including but not limited to, pyrryl, furyl, pyridyl, thiophenyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbozoyl, and isoxazolyl and the like, optionally substituted with a group described in Y section (b);

(d) —CON(R$^3$)—[phenyl-X′]

wherein X′ is halo, —C(O)aryl, CF$_3$, or OR$^3$; —NR$_3$COR$^3$; —OCONH$_2$; —CR$^3$R$^3$R$^4$; —CH$_2$OR$^3$; —CH- $_2OR^3$; —$CH_2CO_2R^3$; —$CH_2OCOR^3$; $R^3CH(R^3)CH_2SO_3$—; —$NHCH_2COOR^3$; halo such as F, Cl, Br and I; $N+R^3R^3R^4R^7$; —$NR^3SO_2R^3$; $COR^3$; $NO_2$; or CN; or

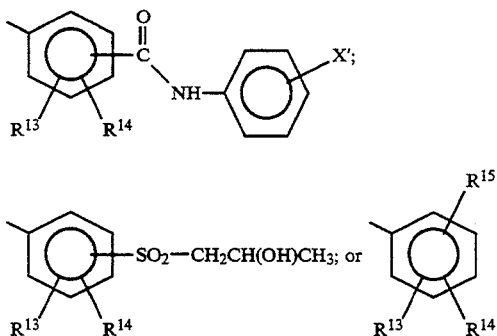

wherein $R^{13}$, $R^{14}$ and $R^{15}$ independently represents: BO— wherein B is —$CH_2$-oxacyclopropyl, —$CH_2OR^3$, —$CH_2C(O)R^3$, —$CH_2CH(R^3)R^3$, —$CH_2$Aryl, —$CH_2CH(OH)$—$CH_2OH$; $R^3C(R^3)_2CH_2SO_2$; or $R^{13}$-$R^{14}$ or $R^{14}$-$R^{15}$ are joined together to form a bridge such as —$OCHR^2CHR^2$—$S(O)_n$- wherein n is 0 to 3; or

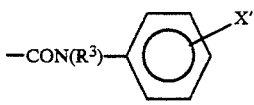

where X' is halo, —C(O)aryl, —$CF_3$, or —$OR^3$; —$CH_2OR^3$; —$CH_2CO_2R^3$; —$CH_2COR^3$; —$NHCH_2COOR^3$; —$N+R^3R^3R^4R^7$.

$R^1$ and $R^2$ are independently hydrogen, halogen, or lower alkyl, specifically including lower alkyl of 1-6 carbon atoms, e.g., methyl, cyclopropylmethyl, ethyl, isopropyl, butyl, pentyl and hexyl, as well as $C_{3-8}$ cycloalkyl, for example, cyclopentyl; halo lower alkyl especially $C_{1-6}$ haloalkyl, for example, trifluoromethyl; halo especially fluoro; —COOH; —$CONR^{16}R^{17}$ wherein $R^{16}$ and $R^{17}$ independently represent $C_{1-6}$ alkyl and hydrogen, —$COOR^3$, lower alkenyl especially $C_{2-6}$ alkenyl e.g., vinyl, allyl, $CH_3CH=CH$—$CH_2$—$CH_2$, and $CH_3CH_2)$—$_3CH=CH$—; —$COR^3$; —$CH_2OR^3$; lower alkynyl especially $C_{2-6}$ alkynyl e.g., —C≡CH; —$CH_2NR^4R^3$; —$CH_2SR^3$; =O; —$OR^3$; or —$NR^3R^4$;

$R^3$ and $R^4$ are independently alkyl, alkenyl, alkynyl, aryl, aralkyl, alkyaryl, hydrogen, $C_{1-6}$ alkoxy-$C_{1-10}$ alkyl, $C_{1-6}$ alkylthio-$C_{1-10}$ alkyl, and $C_{1-10}$ substituted alkyl (wherein the substituent is independently hydroxy or carbonyl, located on any of $C_{1-10}$);

$R^5$ is lower alkyl, lower alkenyl, lower alkynyl, hydroxyl, hydrogen, halo lower alkyl, halo lower alkenyl, halo lower alkynyl, aralkyl, or aryl;

$R^6$ is lower alkyl, lower alkenyl, lower alkynyl, aralkyl, halo lower alkyl, halo lower alkenyl, halo lower alkynyl, or aryl;

$R^7$ is an organic or inorganic anion;

$R^8$ is halo alkyl, halo lower alkyl, halo lower alkenyl, halo lower alkynyl, lower alkenyl, lower alkynyl, aralkyl, or aryl;

$R^9$ is independently hydrogen, halogen, lower alkyl, halo lower alkyl, lower alkenyl, lower alkynyl, —$CONR^3R^4$, —$COR^5$, —$CO_2R^5$, —$CH_2OR^5$, —$CH_2NR^5R^5$, —$CH_2SR^5$, =O, =$NR^5$, —$NR^3R^4$, —$NR^3R^4 R^7$, or —$OR^5$;

$R^{10}$ is —$R^3$, —$R^8$, —$C(O)N(OR^3)R^3$, or —$OR^3$.

$R^{11}$ is $C_1$ to $C_{12}$ alkyl; substituted $C_1$ to $C_{12}$ alkyl wherein the substituent is selected from the group consisting of hydroxy and amino, alkenyl, lower alkoxyalkyl; alkylcarbonylalkyl, -alkylamino, -alkylamino(alkyl or dialyl), lower alkyl $S(O)_m$-lower alkyl in which m is 0, 1 or 2; imidazolyl lower alkyl, morpholinyl lower alkyl, thiazolinyl lower alkyl, piperidinyl lower alkyl, imidazolylcarbonyl, morpholinyl carbonyl, amorpholinyl (lower alkyl) aminocarbonyl, N-pyrrylpyridinyl-lower alkyl; pyridylthio-lower alkyl; morpholinyllower alkyl; hydroxyphenylthio-lower alkyl; cyanophenylthio-lower alkyl; imidazolylthio-lower alkyl; triazolylthio-lower alkyl; triazolylphenylthio-lower alkyl; tetrazolylthio-lower alkyl; tetrazolylphenylthio-lower alkyl; aminophenylthio-lower alkyl; N,N-di-substituted aminophenylthio-lower alkyl wherein the substituents each independently represent lower alkyl; amidinophenylthio-lower alkyl; phenylsulfinyl-lower alkyl; or phenylsulfonyl lower alkyl;

$R^{12}$ is alkyl; substituted alkyl wherein the substituent is selected from the group consisting of hydroxy and amino; -lower alkyl-O-$R^{18}$, wherein $R^{18}$ is —$PO_2(O-H)$—M+ wherein M+ is a pharmaceutically acceptable cation; —$C(O)(CH_2)_2CO_2$—M+, or —$SO_3$—M+; -lower akylcarbonyl-lower alkyl; -carboxy lower alkyl; -lower alkylamino-lower alkyl; N,N-di-substituted amino lower alkyl-, wherein the substituents each independently represent lower alkyl; pyridyl-lower alkyl; imidazolyl-lower alkyl; imidazolyl-Y-lower alkyl wherein Y is thio or amino; morpholinyl-lower alkyl; pyrrolidinyl-lower alkyl; thiazolinyl-lower alkyl; piperidinyl-lower alkyl; morpholinyl-lower hydroxyalkyl; N-pyrryl; piperazinyl-lower alkyl; N-substituted piperazinyl-lower alkyl, wherein the substituent is lower alkyl; triazolyl-lower alkyl; tetrazolyl-lower alkyl; tetrazolylamino-lower alkyl; or thiazolyl-lower alkyl; and Formula II

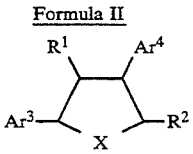

$Ar^3$ and $Ar^4$ are independently

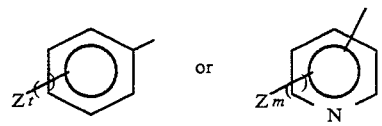

wherein
X is O, S, S(O), $S(O)_2$, or $NR^{10}$;
m is 1, 2, or 3;
t is 1, 2, 3, or 4;
Z is independently W or Y; and Formula III

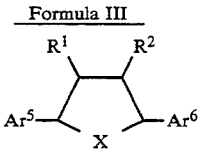

wherein $Ar^5$ is:

-continued
Formula III

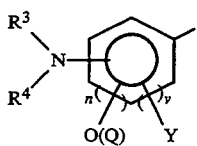

wherein $Ar^6$ is:

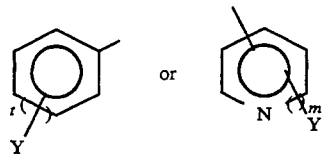

v is 0, 1, or 2; and

Q is selected from the group consisting of substituted $C_1$ to $C_{12}$ alkyl wherein the substituent is selected from the group consisting of hydroxy and amino, alkylcarbonylalkyl, alkyl; lower alkyl $S(O)_m$-lower alkyl in which m is 1 or 2; imidazolyl lower alkyl, morpholinyl lower alkyl, thiazolinyl lower alkyl, piperidinyl ower alkyl, imidazolylcarbonyl, morpholinyl carbonyl, amorpholinyl (lower alkyl) aminocarbonyl, N-pyrrylpyridinyl-lower alkyl; pyridylthio-lower alkyl; morpholinyl-lower alkyl; hydroxyphenylthio-lower alkyl; cyanophenylthio-lower alkyl; imidazolylthio-lower alkyl; triazolylthio-lower alkyl; triazolylphenylthio-lower alkyl; tetrazolylthio-lower alkyl; tetrazolylphenylthio-lower alkyl; aminophenylthio-lower alkyl; N,N-di-substituted aminophenylthio-lower alkyl wherein the amine substituents each independently represent lower alkyl; amidinophenylthio-lower alkyl; phenylsulfinyl-lower alkyl; or phenylsulfonyl lower alkyl; -lower alkyl-O-$R^{18}$, wherein $R^{18}$ is —$PO_2(OH)$—M+ wherein M+ is a pharmaceutically acceptable cation; —$C(O)(CH_2)_2CO_2$—M+, or —$SO_3$—M+; -lower alkylcarbonyl-lower alkyl; -carboxy lower alkyl; -lower alkylamino-lower alkyl; N,N-di-substituted amino lower alkyl-, wherein the amine substituents each independently represent lower alkyl; pyridyl-lower alkyl; imidazolyl-lower alkyl; imidazolyl-Y'-lower alkyl wherein Y' is thio or amino; morpholinyl-lower alkyl; pyrrolidinyl-lower alkyl; thiazolinyl-lower alkyl; piperidinyl-lower alkyl; morpholinyl-lower hydroxyalkyl; N-pyrryl; piperazinyl-lower alkyl; N-substituted piperazinyl-lower alkyl, wherein the amino substituent is lower alkyl; triazolyl-lower alkyl; tetrazolyl-lower alkyl; tetrazolylamino-lower alkyl; or thiazolyl-lower alkyl.

These compounds in general reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase.

A method to treat disorders mediated by PAF or leukotrienes is also disclosed, that includes administering an effective amount of one or more of the above-identified compounds or a pharmaceutically acceptable salt thereof, optionally in a pharmaceutically acceptable carrier.

Examples of immune and allergic disorders include general inflammation, cardiovascular disorders, skeletal-muscular disorders, osteoarthritis, gout, asthma, lung edema, adult respiratory distress syndrome, pain, aggregation of platelets, rheumatoid arthritis, juvenile rheumatoid arthritis, psoriatic arthritis, psoriasis, autoimmune uveitis, allergic encephalomyelitis, systemic lupus erythematosis, acute necrotizing hemorrhagic encephalopathy, idiopathic thrombocytopenia, polychondritis, chronic active hepatitis, idiopathic sprue, Crohn's disease, Graves opthalmopathy, primary biliary cirrhosis, uveitis posterior, interstitial lung fibrosis; allergic asthma; and inappropriate allergic responses to environmental stimuli such as poison ivy, pollen, insect stings and certain foods, including atopic dermatitis and contact dermatitis.

The compounds disclosed herein can also be used as research tools to study the structure and location of PAF receptors as well as biological pathways involving leukotrienes.

DETAILED DESCRIPTION OF THE INVENTION

Figure 1:
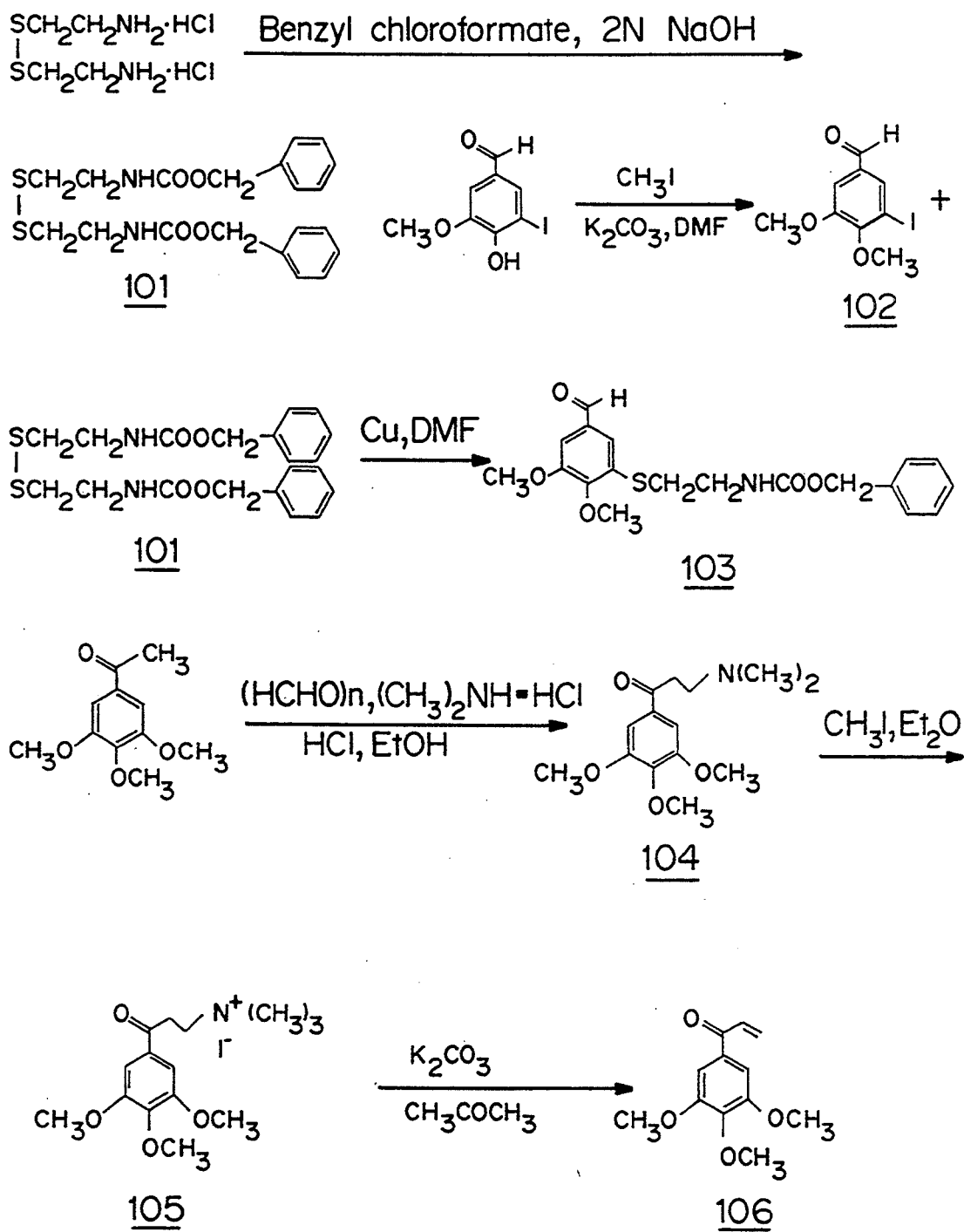
FIG. 1 is a schematic illustration of a process for a preparation of 3,4,5-trimethoxyphenylvinylketone (compound 106, FIG. 1).

I. Description and Synthesis of the Compounds

A. Compounds

The term alkyl, as used herein, unless otherwise specified, refers to a saturated straight, branched, or cyclic hydrocarbon of $C_1$ to $C_{10}$, and specifically includes methyl, ethyl, propyl, isopropyl, butyl, isobutyl, t-butyl, phenyl, cyclopentyl, isopentyl, neopentyl, hexyl, isohexyl, cyclohexyl, 3-methylpentyl, 2,2-dimethylbutyl, and 2,3-dimethylbutyl.

The term lower alkyl, as used herein, and unless otherwise specified, refers to a $C_1$ to $C_6$ saturated straight, branched, or cyclic (in the case of $C_{5-6}$) hydrocarbon, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term alkenyl, as referred to herein, and unless otherwise specified, refers to a straight, branched, or cyclic (in the case of $C_{5-6}$) hydrocarbon of $C_2$ to $C_{10}$ with at least one double bond.

The term lower alkenyl, as referred to herein, and unless otherwise specified, refers to an alkenyl group of $C_2$ to $C_6$, and specifically includes vinyl and allyl.

The term lower alkylamino refers to an amino group that has one or two lower alkyl substituents.

The term alkynyl, as referred to herein, and unless otherwise specified, refers to a $C_2$ to $C_{10}$ straight or branched hydrocarbon with at least one triple bond.

The term lower alkynyl, as referred to herein, and unless otherwise specified, refers to a $C_2$ to $C_6$ alkynyl group, specifically including acetylenyl and propynyl.

The term aryl, as used herein, and unless otherwise specified, refers to a phenyl or substituted phenyl, wherein the substituent is halo or lower alkyl.

The term halo, as used herein, includes fluoro, chloro, bromo, and iodo.

The term halo (alkyl, alkenyl, or alkynyl) refers to a (alkyl, alkenyl, or alkynyl) group in which at least one of the hydrogens in the group has been replaced with a halogen atom.

The term aralkyl refers to an aryl group with an alkyl substituent.

The term alkaryl refers to an alkyl group that has an aryl substituent.

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary amine.

The term "metabolically cleavable leaving group" refers to a moiety that can be cleaved in vivo from the molecule to which it is attached, and includes but is not limited to an organic or inorganic anion, a pharmaceutically acceptable cation, acyl (for example, (alkyl)C(O), including acetyl, propionyl, and butyryl), alkyl, phosphate, sulfate and sulfonate.

The term "enantiomerically enriched composition or compound" refers to a composition or compound that includes at least 95% by weight of a single enantiomer of the compound.

The term PAF receptor antagonist refers to a compound that binds to a PAF receptor with a binding constant of 30 μM or lower.

The term 5-lipoxygenase inhibitor refers to a compound that inhibits the enzyme at 30 μM or lower in a broken cell system.

The term pharmaceutically active derivative refers to any compound that upon administration to the recipient, is capable of providing directly or indirectly, the compounds disclosed herein.

The 2,5-diaryl tetrahydrothiophenes, pyrrolidines, and tetrahydrofurans, 1,3 diaryl cyclopentanes, and the 2,4-diaryl tetrahydrothiophenes, pyrrolidines and tetrahydrofurans of the above-defined formulas exhibit PAF receptor antagonist activity or inhibit the enzyme 5-lipoxygenase, or have dual activity, and are thus useful in the treatment of humans who have immune and allergic disorders that are mediated by PAF or products of 5-lipoxygenase.

The following are nonlimiting examples of compounds that fall within Formulas I, II, and III. These examples are merely exemplary, and are not intended to limit the scope of the invention.

Formula I cis and trans Isomers of the following compounds:

N-Alkyl/arylhydroxyureas:

2-[5-(N'-Butyl-N'-hydroxyureidyl)-3-methoxy-4-methoxyethoxyphenyl]-5-(3,4,5-trimethoxyphenyl)-tetrahydrothiophene.

2-[5-(N'-Butyl-N'-hydroxyureidyl)-3-methoxy-4-methoxythioethoxyphenyl]-5-(3,4,5-trimethoxyphenyl)-tetrahydrofuran.

2-[5-(N'-Butyl-N'-hydroxyureidyl)-4-hydroxyphenylthioethoxy-3-methoxyethoxyphenyl]-5-(3,4,5-trimethoxyphenyl)-tetrahydrofuran.

2-[5-(N'-Butyl-N'-hydroxyureidyl)-4-(N-nicotinoyl-N-phenylaminoethoxy)-3-methoxyphenyl]-5-(3,4,5-trimethoxyphenyl)-tetrahydrofuran.

2-[5-(N'-Butyl-N'-hydroxyureidyl)-4-(N-3-pyridiniumcarbonyl-N-phenylaminoethoxy)-3-methoxyphenyl]-5-(3,4,5-trimethoxyphenyl)-tetrahydrofuran-propyl iodide.

2-[5-(N'-p-Chlorophenyl-N'-hydroxyureidyl)-4-(N-3-pyridiniumcarbonyl-N-phenylaminoethoxy)-3-methoxyphenyl]-5-(3,4,5-trimtoxyphenyl)-tetrahydrofuran-propyl iodide.

2-[5-(N'-Butyl-N'-hydroxyureidyl)-4-(N-3-pyridiniumcarbonyl-N-phenylaminoethoxy)-3-methoxyphenyl]-5-(3,4,5-trimethoxyphenyl)-tetrahydrofuran-ethyl iodide.

2-[5-(N'-p-Chlorophenyl-N'-hydroxyureidyl)-4-(N-3-pyridiniumcarbonyl-N-phenylaminoethoxy)-3-methoxyphenyl]-5-(3,4,5-trimethoxyphenyl)-tetrahydrofuran-ethyl iodide.

2-[5-(N'-p-Chlorophenyl-N'-hydroxyureidyl)-3-methoxy-4-propoxyphenyl)-5-(3,4,5-trimethoxyphenyl)-tetrahydrofuran.

2-[5-(N'-p-Chlorophenyl-N'-hydroxyureidyl)-4-methoxyethoxy-3-methoxyphenyl]-5-(3,4,5-trimethoxyphenyl)-tetrahydrothiophene.

2-[5-(N'-p-Chlorophenyl-N'-hydroxyureidyl)-4-methylthioethoxy-3-methoxyphenyl]-5-(3,4,5-trimethoxyphenyl)-tetrahydrofuran.

2-[5-(N'-p-Chlorophenyl-N'-hydroxyureidyl)-4-p-hydroxyphenylthioethoxy-3-methoxyphenyl]-5-(3,4,5-trimethoxyphenyl)-tetrahydrofuran.

2-[5-(N'-p-Chlorophenyl-N'-hydroxyureidyl)-4-(N-nicotinoyl-N-phenylaminoethoxy)-3-methoxyphenyl]-5-(3,4,5-trimethoxyphenyl)-tetrahydrofuran.

2-[5-(N'-Butyl-N'-hydroxyureidyl)-4-p-cyanophenylthioethoxy-3-methoxyphenyl]-5-(3,4,5-trimethoxyphenyl)-tetrahydrofuran.

2-[5-(N'-p-Chlorophenyl-N'-hydroxyureidyl)-4-p-cyanophenylthioethoxy-3-methoxyphenyl]-5-(3,4,5-trimethoxyphenyl)-tetrahydrofuran.

2-[5-(N'-Butyl-N'-hydroxyureidyl)-4-p-methoxyphenylthioethoxy-3-methoxyphenyl]-5-(3,4,5-trimethoxyphenyl)-tetrahydrofuran.

2-[5-(N'-p-Chlorophenyl-N'-hydroxyureidyl)-4-p-methoxyphenylthioethoxy-3-methoxyphenyl]-5-(3,4,5-trimethoxyphenyl)-tetrahydrofuran.

2-[5-(N'-tert-Butyl-N'-hydroxyureidyl)-3-methoxy-4-propoxyphenyl]-5-(3,4,5-trimethoxyphenyl)-tetrahydrothiophene.

2-[5-(N'-n-Butyl-N'-hydroxyureidyl)-3-methoxy-4-propoxyphenyl]-5-(3,4,5-trimethoxy phenyl)-tetrahydrofuran.

2-[5-(N'-Ethyl-N'-hydroxyureidyl)-3-methoxy-4-propoxyphenyl]-5-(3,4,5-trimethoxy phenyl)-tetrahydrofuran.

2-[5-(N'-Cyclohexyl-N'-hydroxyureidyl)-3-methoxy-4-propoxyphenyl]-5-(3,4,5-trimethoxy phenyl)-tetrahydrofuran.

2-[5-(N'-Benzyl-N'-hydroxyureidyl)-3-methoxy-4-propoxyphenyl]-5-(3,4,5-trimethoxyphenyl)-tetrahydrofuran.

2-(5-N'-Hydroxyureidyl-3-methoxy-4-propoxyphenyl)-5-(3,4,5-trimethoxyphenyl)-tetrahydrothiophene.

2-[5-(N'-Hydroxy-N'-methylureidyl)-3-methoxy-4-propoxyphenyl]-5-(3,4,5-trimethoxyphenyl)-tetrahydrothiophene.

2-[5-(N'-Hydroxy-N'-i-propylureidyl)-3-methoxy-4-propoxyphenyl]-5-(3,4,5-trimethoxyphenyl)-tetrahydrothiophene.

2-[5-(N'-sec-Butyl-N'-hydroxyureidyl)-3-methoxy-4-propoxyphenyl]-5-(3,4,5-trimethoxyphenyl)-tetrahydrothiophene.

2-[5-(N'-Hydroxy-N'-propylureidyl)-3-methoxy-4-propoxyphenyl]-5-(3,4,5-trimethoxyphenyl)-tetrahydrothiophene.

2-[5-(N'-Hydroxy-N'-propylureidyl)-3-methoxy-4-propoxyphenyl]-5-(3,4,5-trimethoxyphenyl)-tetrahydrofuran.

2-[5-(N'-Hydroxy-N'-n-pentylureidyl)-3-methoxy-4-propoxyphenyl]-5-(3,4,5-trimethoxyphenyl)-tetrahydrofuran.

2-[5-(N'-Cyclohexyl-N'-hydroxyureidyl)-3-methoxy-4-propoxyphenyl]-5-(3,4,5-trimethoxyphenyl)-tetrahydrofuran.

2-[5-(N'-Hexyl-N'-hydroxyureidyl)-3-methoxy-4-propoxyphenyl]-5-(3,4,5-trimethoxyphenyl)-tetrahydrofuran.

2-[5-(N'-Benzyl-N'-hydroxyureidyl)-3-methoxy-4-propoxyphenyl]-5-(3,4,5-trimethoxyphenyl)-tetrahydrofuran.

2-[5-(N'-Hydroxy-N'-octylureidyl)-3-methoxy-4-propoxyphenyl]-5-(3,4,5-trimethoxyphenyl)-tetrahydrofuran.

2-[5-(N'-Hydroxy-N'-methoxyethylureidyl)-3-methoxy-4-propoxyphenyl]-5-(3,4,5-trimethoxyphenyl)-tetrahydrofuran.

2-[5-(N'-Decyl-N'-hydroxyureidyl)-3-methoxy-4-propoxyphenyl]-5-(3,4,5-trimethoxyphenyl)-tetrahydrofuran.

2-[5-(N'-Hydroxy-N'-n-pentylureidyl)-3-methoxy-4-propoxyphenyl]-5-(3,4,5-trimethoxyphenyl)-tetrahydrothiophene.

2-[5-(N'-Cyclohexyl-N'-hydroxyureidyl)-3-methoxy-4-propoxyphenyl]-5-(3,4,5-trimethoxyphenyl)-tetrahydrothiophene.

2-[5-(N'-Hexyl-N'-hydroxyureidyl)-3-methoxy-4-propoxyphenyl]-5-(3,4,5-trimethoxyphenyl)-tetrahydrothiophene.

2-[5-(N'-Benzyl-N'-hydroxyureidyl)-3-methoxy-4-propoxyphenyl]-5-(3,4,5-trimethoxyphenyl)-tetrahydrothiophene.

2-[5-(N'-Hydroxy-N'-octylureidyl)-3-methoxy-4-propoxyphenyl]-5-(3,4,5-trimethoxyphenyl)-tetrahydrothiophene.

2-[5-(N'-Hydroxy-N'-methoxyethylureidyl)-3-methoxy-4-propoxyphenyl]-5-(3,4,5-trimethoxyphenyl)-tetrahydrothiophene.

2-[5-(N'-Decyl-N'-hydroxyureidyl)-3-methoxy-4-propoxyphenyl]-5-(3,4,5-trimethoxyphenyl)-tetrahydrothiophene.

Triple bonded hydroxamates:

2-[5-[1-(N-Acetyl-N-hydroxyamino)propyn-3-yl]-3-methoxy-4-propoxyphenyl]-5-(3,4,5-trimethoxyphenyl)-tetrahydrofuran.

2-[5-[1-(N-Hydroxy-N-propanoylamino)propyn-3-yl]-3-methoxy-4-propoxyphenyl]-5-(3,4,5-trimethoxyphenyl)-tetrahydrofuran.

2-[5-[1-(N-Butanoyl-N-hydroxyamino)propyn-3-yl]-3-methoxy-4-propoxyphenyl]-5-(3,4,5-trimethoxyphenyl)-tetrahydrofuran.

2-[5-[1-(N-Hydroxy-N-i-propanoylamino)propyn-3-yl]-3-methoxy-4-propoxyphenyl]-5-(3,4,5-trimethoxyphenyl)-tetrahydrofuran.

2-[5-[1-(N-Hydroxy-N-cyclohexanecarbonylamino)-propyn-3-yl]-3-methoxy-4-propoxyphenyl]-5-(3,4,5-trimethoxyphenyl)-tetrahydrofuran.

2-[5-[1-(N-Benzoyl-N-hydroxylamino)propyn-3-yl]-3-methoxy-4-propoxyphenyl]-5-(3,4,5-trimethoxyphenyl)-tetrahydrofuran.

2-[5-[1-(N-hydroxy-N-3-phenoxybenzoylamino)-propyn-3-yl]-3-methoxy-4-propoxyphenyl]-5-(3,4,5-trimethoxyphenyl)-tetrahydrofuran.

2-[5-[1-(N-hydroxy-N-4-methoxybenzoylamino)-propyn-3-yl]-3-methoxy-4-propoxyphenyl]-5-(3,4,5-trimethoxyphenyl)-tetrahydrofuran.

2-[5-[1-(N-3-Benzoylbenzoyl-N-hydroxyamino)propyn-3-yl]-3-methoxy-4-propoxyphenyl]-5-(3,4,5-trimethoxyphenyl)-tetrahydrofuran.

2-[5-[1-(N-Hydroxy-N-4-hydroxybenzoylamino)-propyn-3-yl]-3-methoxy-4-propoxyphenyl]-5-(3,4,5-trimethoxypheny)-tetrahydrofuran.

Triple bonded ureas:

2-[5-[1-(N'-Hydroxy-N'-methylureidyl)propyn-3-yl]-3-methoxy-4-propoxyphenyl]-5-(3,4,5-trimethoxyphenyl)-tetrahydrofuran.

2-[5-[1-(N'-Ethyl-N'-hydroxyureidyl)propyn-3-yl]-3-methoxy-4-propoxyphenyl]-5-(3,4,5-trimethoxyphenyl)-tetrahydrofuran.

2-[5-[1-(N'-Hydroxy-N'-propylureidyl)propyn-3-yl]-3-methoxy-4-propoxyphenyl]-5-(3,4,5-triomethoxyphenyl)-tetrahydrofuran.

2-[5-[1(N'-n-Butyl-N'-hydrpxyureidyl)propyn-3-yl]-3-methoxy-4-propoxyphenyl]-5-(3,4,5-trimethoxyphenyl)-tetrahydrofuran.

2-[5-[1-(N'-Hydroxy-N'-i-propylureidyl)propyn-3-yl]-3-methoxy-4-propoxyphenyl]-5-(3,4,5-trimethoxyphenyl)-tetrahydrofuran.

2-[5-[1-(N'-t-Butyl-N'-hydroxyureidyl)propyn-3-yl]-3-methoxy-4-propoxyphenyl]-5-(3,4,5-trimethoxyphenyl)-tetrahydrofuran.

2-[5-[1-(N'-Benzyl-N'-hydroxyureidyl)propyn-3-yl]-3-methoxy-4-propoxyphenyl]-5-(3,4,5-trimethoxyphenyl)-tetrahydrofuran.

2-[5-[1-(N'-Cyclopropylmethyl-N'-hydroxyureidyl)-propyn-3-yl]-3-methoxy-4-propoxyphenyl]-5-(3,4,5-trimethoxyphenyl)-tetrahydrofuran.

2-[5-[1-(N'-Allyl-N'-hydroxyureidyl)propyn-3-yl]-3-methoxy-4-propoxyphenyl]-5-(3,4,5-trimethoxyphenyl)-tetrahydrofuran.

2-[5-[1-(N'-Hydroxy-N'-hydroxyethylureidyl)propyn-3-yl]-3-methoxy-4-propoxyphenyl]-5-(3,4,5-trimethoxyphenyl)-tetrahydrofuran.

Double bonded hydroxamates: Both cis and trans isomers at the tetrahydrofuran ring 2-[5-[trans-1-(N-Acetyl-N-hydroxyamino)propen-3-yl]-3-methoxy-4-propoxyphenyl]-5-(3,4,5-trimethoxyphenyl)-tetrahydrofuran.

2-[5-[trans-1-(N-Hydroxy-N-propanoylamino)propen-3-yl]-3-methoxy-4-propoxyphenyl]-5-(3,4,5-trimethoxyphenyl)-tetrahydrofuran.

2-[5-[trans-1-(N-Butanoyl-N-hydroxyamino)propen-3-yl]-3-methoxy-4-propoxyphenyl]-5-(3,4,5-trimethoxyphenyl)-tetrahydrofuran.

2-[5-[trans-1-(N-hydroxy-N-nicotinoylamino)propen-3-yl]-3-methoxy-4-propoxyphenyl]-5-(3,4,5-trimethoxyphenyl)-terahydrofuran.

2-[5-[trans-1-(N-hydroxy-N-phenylacetylamino)propen-3-yl]-3-methoxy-4-propoxyphenyl]-5-(3,4,5-trimethoxyphenyl)-tetrahydrofuran.

2-[5-[trans-1-(N-3-Phenoxybenzoyl-N-hydroxyamino)-propen-3-yl]-3-methoxy-4-propoxyphenyl]-5-(3,4,5-trimethoxyphenyl)-tetrahydrofuran.

2-[5-[trans-1-(N-3-Chlorobenzoyl-N-hydroxyamino)-propen-3-yl]-3-methoxy-4-propoxyphenyl]-5-(3,4,5-trimethoxyphenyl)-tetrahydrofuran.

2-[5-[trans-1-(N-3-Chlorobenzoyl-N-hydroxyamino)-propen-3-yl]-3-methoxy-4-propoxyphenyl]-5-(3,4,5-trimethoxyphenyl)-tetrahydrofuran.

2-[5-[trans-1-(N-2,4-Difluorobenzoyl-N-hydroxyamino)propen-3-yl]-3-methoxy-4-propoxyphenyl]-5-(3,4,5-trimethoxyphenyl)-tetrahydrofuran.

2-[5-[trans-1-(N-3,4-Methylenedioxybenzoyl-N-hydroxyamino)propen-3-yl]-3-methoxy-4-propoxyphenyl]-5-(3,4,5-trimethoxyphenyl)-tetrahydrofuran.

and also the corresponding saturated hydroxamates, e.g.,

2-[5-[1-(N-3,4-Methylenedioxybenzoyl-N-hydroxyamino)propyl]-3-methoxy-4-propoxyphenyl]-5-(3,4,5-trimethoxyphenyl)-tetrahydfforuan.

Double bonded ureas: Both cis and trans isomer at the tetrahydrofuran ring.

2-[5-[trans-1-(N'-Hydroxy-N'-methylureidyl)propen-3-yl]-3-methoxy-4-propoxyphenyl]-5-(3,4,5-trimethoxyphenyl)-tetrahydrofuran.

2-[5-[trans-1-(N'-Ethyl-N'-hydroxyureidyl)propen-3-yl]-3-methoxy-4-propoxyphenyl]-5-(3,4,5-trimethoxyphenyl)-tetrahydrofuran.

2-[5-[trans-1-(N'-Hydroxy-N'-propylureidyl)propen-3-yl]-3-methoxy-4-propoxyphenyl]-5-(3,4,5-trimethoxyphenyl)-tetrahydrofuran.

2-[5-[trans-1-(N'-Butyl-N'-hydroxyureidyl)propen-3-yl]-3-methoxy-4-propoxyphenyl]-5-(3,4,5-trimethoxyphenyl)-tetrahydrofuran.

2-[5-[trans-1-(N'-Hydroxy-N'-i-propylureidyl)propen-3-yl]-3-methoxy-4-propoxyphenyl]-5-(3,4,5-trimethoxyphenyl)-tetrahydrofuran.

2-[5-[trans-1-(N'-t-Butyl-N'-hydroxyureidyl)propen-3-yl]-3-methoxy-4-propoxyphenyl]-5-(3,4,5-trimethoxyphenyl)-tetrahydrofuran.

2-[5-[trans-1-(N'-Benzyl-N'-hydroxyureidyl)propen-3-yl]-N-3-methoxy-4-propoxyphenyl]-5-(3,4,5-trimethoxyphenyl)-tetrahydrofuran.

2-[5-[trans-1-(N'-Allyl-N'-hydroxyureidyl)propen-3-yl]-3-methoxy-4-propoxyphenyl]-5-(3,4,5-trimethoxyphenyl)-tetrahydrofuran.

2-[5-[trans-1-(N'-Cyclohexyl-N'-hydroxyureidyl)propen-3-yl]-3-methoxy-4-propoxyphenyl-5-(3,4,5-trimethoxyphenyl)-tetrahydrofuran.

2-[5-[trans-1-(N'-Hydroxy-N'-methylthioethylureidyl)-propen-3-yl]-3-methoxy-4-propoxyphenyl]-5-(3,4,5-trimethoxyphenyl)-tetrahydrofuran.

2-[5-[trans-1-(N'-Cyclohexyl-N'-hydroxyureidyl)propen-3-yl]-3-methoxy-4-propoxy]-5-(3,4,5-trimethoxyphenyl)-tetrahydrofuran.

and also the corresponding saturated ureas, e.g.,

2-[5-[1(N'-Cyclohexyl-N'-hydroxyureidyl)propyl]-3-methoxy-4-propoxyphenyl]-5-(3,4,5-trimethoxyphenyl)-tetrahydrofuran.

Formula II cis and trans isomer of the following compounds:

N-Alkyl/arylhydroxyureas:

4-[5-(N'-Butyl-N'-hydroxyureidyl)-3-methoxy-4-methoxyethoxyphenyl]-2-(3,4,5-trimethoxyphenyl)-tetrahydrofuran 4-[5-(N'-Butyl-N'-hydroxyureidyl)-3-methoxy-4-methylthioethoxyphenyl]-2-(3,4,5-trimethoxyphenyl)-tetrahydrofuran 4-[5-(N'-Butyl-N'-hydroxyureidyl)-4-p-hydroxyphenylthioethoxy-3-methoxyphenyl]-2-(3,4,5-trimethoxyphenyl)-tetrahydrofuran 4-[5-(N'-Butyl-N'-hydroxyureidyl)-3-methoxy-4-(N-nicotinoyl-N-phenyaminoethoxy)-phenyl]-2-(3,4,5-trimethoxyphenyl)-tetrahydrofuran 4-[5-(N'-Butyl-N'-hydroxyureidyl)-3-methoxy-4-[(N-(N-propyl-3-pyridiniumcarbonyl)]-N-phenylaminoethoxy)-phenyl]-2-(3,4,5-trimethoxyphenyl)-tetrahydrofuran iodide 4-[5-(N'-p-Chlorophenyl-N'-hydroxyureidyl)-3-methoxy-4-(N-(N-propyl-3-pyridiniumcarbonyl)-N-phenylaminoethoxy)-phenyl]-2-(3,4,5-trimethoxyphenyl)-tetrahydrofuran iodide 4-[5-(N'-Butyl-N'-hydroxyureidyl)-3-methoxy-4-(N-(N-ethyl-3-pyridiniumcarbonyl)-N-phenyaminoethoxy)-phenyl]-2-(3,4,5-trimethoxyphenyl)-tetrahydrofuran iodide 4-[5-(N'-p-Chlorophenyl-N'-hydroxyureidyl)-3-methoxy-4-(N-(N-ethyl-3-pyridiniumcarbonyl)-N-phenyaminoethoxy)-phenyl]-2-(3,4,5-trimethoxyphenyl)-tetrahydrofuran iodide 4-[5-(N'-p-Chlorophenyl-N'-hydroxyureidyl)-3-methoxy-4-propoxyphenyl]-2-(3,4,5-trimethoxyphenyl)-tetrahydrofuran 4-[5-(N'-p-Chlorophenyl-N'-hydroxyureidyl)-3-methoxy-4-methoxyethoxyphenyl]-2-(3,4,5-trimethoxyphenyl)-tetrahydrofuran 4-[5-(N'-p-Chlorophenyl-N'-p-hydroxyureidyl)-3-methoxy-4-methylthioethoxyphenyl]-2-(3,4,5-trimethoxyphenyl)-tetrahydrofuran 4-[5-(N'-p-Chlorophenyl-N'-hydroxyureidyl)-4-p-hydroxyphenylthioethoxy-3-methoxyphenyl]-2-(3,4,5-trimethoxyphenyl)-tetrahydrofuran 4-[5-(N'-p-Chlorophenyl-N'-hydroxyureidyl)-3-methoxy-4-(N-nicotinoyl-N-phenylaminoethoxy)-phenyl]-2-(3,4,5-trimethoxyphenyl)-tetrahydrofuran 4-[5-(N'-Butyl-N'-hydroxyureidyl)-4-p-cyanophenylthioethoxy-3-methoxyphenyl]-2-(3,4,5-trimethoxyphenyl)-tetrahydrofuran.

4-[5-(N'-p-Chlorophenyl-N'-hydroxyureidyl)-4-p-cyanophenylthioethoxy-3-methoxyphenyl]-2-(3,4,5-trimethoxyphenyl)-tetrahydrofuran.

4-[5-(N'-Butyl-N'-hydroxyureidyl)-3-methoxy-4-p-methoxyphenylthioethoxyphenyl]-2-(3,4,5-trimethoxyphenyl)-tetrahydrofuran 4-[5-(N'-p-Chlorophenyl-N'-hydroxyureidyl)-3-methoxy-4-p-methoxyphenylthioethoxyphenyl]-2-(3,4,5-trimethoxyphenyl)-tetrahydrofuran 4-[5-(N'-tert-Butyl-N'-hydroxyureidyl)-3-methoxy-4-propoxyphenyl]-2-(3,4,5-trimethoxyphenyl)-tetrahydrothiophene 4-[5-(N'-Butyl-N'-hydroxyureidyl)-3-methoxy-4-propoxyphenyl]-2-(3,4,5-trimethoxyphenyl)-tetrahydrofuran 4-[5-(N'-Ethyl-N'-hydroxyureidyl)-3-methoxy-4-propoxyphenyl]-2-(3,4,5-trimethoxyphenyl)-tetrahydrofuran 4-[4-(N'-Cyclohexyl-N'-hydroxyureidyl)-3-methoxy-4-propoxyphenyl]-2-(3,4,5-trimethoxyphenyl)-tetrahydrofuran 4-[5-(N'-Benzyl-N'-hydroxyureidyl)-3-methoxy-4-propoxyphenyl]-2-(3,4,5-trimethoxyphenyl)-tetrahydrofuran 4-[5-N'-Hydroxyureidyl-3-methoxy-4-propoxyphenyl]-2-(3,4,5-trimethoxyphenyl)-tetrahydrothiophene 4-[5-(N'-Hydroxy-N'-methylureidyl)-3-methoxy-4-propoxyphenyl]-2-(3,4,5-trimethoxyphenyl)-tetrahydrothiophene 4-[5-(N'-Hydroxy-N'-i-propylureidyl)-3-methoxy-4-propoxyphenyl]-2-(3,4,5-trimethoxyphenyl)-tetrahydrothiophene 4-[5-(N'-sec-Butyl-N'-hydroxyureidyl)-3-methoxy-4-propoxyphenyl]-2-(3,4,5-trimethoxyphenyl)-tetrahydrothiophene 4-[5-(N'-Hydroxy-N'-n-propylureidyl)-3-methoxy-4-propoxyphenyl]-2-(3,4,5-trimethoxyphenyl)-tetrahydrothiophene 4-[5-(N'-Hydroxy-N'-n-propylureidyl)-3-methoxy-4-propoxyphenyl]-2-(3,4,5-trimethoxyphenyl)-tetrahydrofuran 4-[5-(N'-Hydroxy-N'-n-pentylureidyl)-3-methoxy-4-propoxyphenyl]-2-(3,4,5-trimethoxyphenyl)-tetrahydrofuran 4-[5-(N'-Hydroxy-N'-n-pentylureidyl)-3-methoxy-4-propoxyphenyl]-2-(3,4,5-trimethoxyphenyl)-tetrahydrofuran 4-[5-(N'-Hydroxy-N'-n-pentylureidyl)-3-methoxy-4-propoxyphenyl]-2-(3,4,5-trimethoxyphenyl)-tetrahydrofuran 4-[5-(N'-Cyclohexyl-N'-hydroxyureidyl)-3-methoxy-4-propoxyphenyl]-2-(3,4,5-trimethoxyphenyl)-tetrahydrofuran 4-[5-(N'-n-Hexyl-N'-hydroxyureidyl)-3-methoxy-4-propoxyphenyl]-2-(3,4,5-trimethoxyphenyl)-tetrahydrofuran 4-[5-(N'-Benzyl-N'-hydroxyureidyl)-3-methoxy-4-propoxyphenyl]-2-(3,4,5-trimethoxyphenyl)-tetrahydrothiophene 4-[5-(N'-Hydroxy-N'-n-octylureidyl)-3-methoxy-4-propoxyphenyl]-2-(3,4,5-trimethoxyphenyl)-tetrahydrofuran 4-[5-(N'-Hydroxy-N'-methoxyethylureidyl)-3-methoxy-4-propoxyphenyl]-2-(3,4,5-trimethoxyphenyl)-tetrahydrofuran 4-[5-(N'-n-Decyl-N'-hydroxyureidyl)-3-methoxy-4-propoxyphenyl]-2-(3,4,5-trimethoxyphenyl)-tetrahydrofuran 4-[5-(N'-Hydroxy-N'-n-pentylureidyl)-3-methoxy-4-propoxyphenyl]-2-(3,4,5-trimethoxyphenyl)-tetrahydrothiophene 4-[5-(N'-Cyclohexyl-N'-hydroxylureidyl)-3-methoxy-4-propoxyphenyl]-2-(3,4,5-trimethoxyphenyl)-tetrahydrothiophene 4-[5-(N'-n-Hexyl-N'-hydroxyureidyl)-3-methoxy-4-propoxyphenyl]-2-(3,4,5-trimethoxyphenyl)-tetrahydrothiophene 4-[5-(N'-Hydroxy-N'-n-octylureidyl)-3-methoxy-4-propoxyphenyl]-2-(3,4,5-trimethoxyphenyl)-tetrahydrothiophene 4-[5-(N'-Hydroxy-N'-methoxyethylureidyl)-3-methoxy-4-propoxyphenyl]-2-(3,4,5-trimethoxyphenyl)-tetrahydrothiophene 4-[5-(N'-n-Decyl-N'-hydroxylureidyl)-3-methoxy-4-propoxyphenyl]-2-(3,4,5-trimethoxyphenyl)-tetrahydrothiophene Triple bonded hydroxamates:
4-[5-[1-(N-Acetyl-N-hydroxyamino)propyn-3-yl]-3-methoxy-4-propoxyphenyl]-2-(3,4,5-trimethoxyphenyl)-tetrahydrofuran.

4-[5-[1-(N-Hydroxy-N-propanoylamino)propyn-3-yl]-3-methoxy-4-propoxyphenyl]-2-(3,4,5-trimethoxyphenyl)-tetrahydrofuran.

4-[5-[1-(N-Butanoyl-N-hydroxyamino)propyn-3-yl]-3-methoxy-4-propoxyphenyl]-2-(3,4,5-trimethoxyphenyl)-tetrahydrofuran.

4-[5-[1-(N-Hydroxy-N-i-propanoylamino)propyn-3-yl]-3-methoxy-4-propoxyphenyl]-2-(3,4,5-trimethoxyphenyl)-tetrahydrofuran.

4-[5-[1-(N-Cyclohexanecarbonyl-N-hydroxyamino)-propyn-3-yl]-3-methoxy-4-propoxyphenyl]-2-(3,4,5-trimethoxyphenyl)-tetrahydrofuran 4-[5-[1-(N-Benzoyl-N-hydroxylamino)propyn-3-yl]-3-methoxy-4-propoxyphenyl]-2(3,4,5-trimethoxyphenyl)-tetrahydrofuran.

4-[5-[1-(N-Hydroxy-N-3-phenoxyoxybenzoylamino)-propyn-3-yl]-3-methoxy-4-propoxyphenyl]-2-(3,4,5-trimethoxyphenyl)-tetrahydrofuran.

4-[5-[1-(N-Hydroxy-N-4-methoxybenzoylamino)-propyn-3-yl]-3-methoxy-4-propoxyphenyl]-2-(3,4,5-trimethoxyphenyl)-tetrahydrofuran.

4-[5-[1-(N-3-Benzoyl-N-hydroxyamino)propyn-3-yl]-3-methoxy-4-propoxyphenyl]-2-(3,4,5-trimethoxyphenyl)-tetrahydrofuran.

4-[5-[1-(N-Hydroxy-N-4-hydroxybenzoylamino)-propyn-3-yl]-3-methoxy-4-propoxyphenyl]-2-(3,4,5-trimethoxyphenyl)-tetrahydrofuran.

Triple bonded ureas:

4-[5-[1-(N'-Hydroxy-N'-methylureidyl)propyn-3-yl]-3-methoxy-4-propoxyphenyl]-2-(3,4,5-trimethoxyphenyl)-tetrahydrofuran.

4-[5-[1-(N'-Ethyl-N'-hydroxyureidyl)propyn-3-yl]-3-methoxy-4-propoxyphenyl]-2-(3,4,5-trimethoxyphenyl)-tetrahydrofuran.

4-[5-[1-(N'-Hydroxy-N'-propylureidyl)propyn-3-yl]-3-methoxy-4-propoxyphenyl]-2-(3,4,5-trimethoxyphenyl)-tetrahydrofuran.

4-[5-[1(N'-n-Butyl-N'-hydroxyureidyl)propyn-3-yl]-3-methoxy-4-propoxyphenyl]-2-(3,4,5-trimethoxyphenyl)-tetrahydrofuran.

4-[5-[1-(N'-Hydroxy-N'-i-propylureidyl)propyn-3-yl]-3-methoxy-4-propoxyphenyl]-2-(3,4,5-trimethoxyphenyl)-tetrahydrofuran.

4-[5-[1-(N'-t-Butyl-N'-hydroxyureidyl)propyn-3-yl]-3-methoxy-4-propoxyphenyl]-2-(3,4,5-trimethoxyphenyl)-tetrahydrofuran.

4-[5-[1-(N'-Benzyl-N'-hydroxyureidyl)propyn-3-yl]-3-methoxy-4-propoxyphenyl]-2-(3,4,5-trimethoxyphenyl)-tetrahydrofuran.

4-[5-[1-(N'-Cyclopropylmethyl-N'-hydroxyureidyl)-propyn-3-yl]-3-methoxy-4-propoxyphenyl]-2-(3,4,5-trimethoxyphenyl)-tetrahydrofuran.

4-[5-[1-(N'-Allyl-N'-hydroxyureidyl)propyn-3-yl]-3-methoxy-4-propoxyphenyl]-2-(3,4,5-trimethoxyphenyl)-tetrahydrofuran.

4-[5-[1-(N'-Hydroxy-N'-hydroxyethylureidyl)propyn-3-yl]-3-methoxy-4-propoxyphenyl]-2-(3,4,5-trimethoxyphenyl)-tetrahydrofuran.

Double bonded hydroxamates: Both cis and trans isomers at the tetrahydrofuran ring 4-[5-[trans-1-(N-Acetyl-N-hydroxyamino)propen-3-yl]-3-methoxy-4-propoxyphenyl]-2-(3,4,5-trimethoxyphenyl)-tetrahydrofuran.

4-[5-[trans-1-(N-Hydroxy-N-propanoylamino)propen-3-yl]-3-methoxy-4-propoxyphenyl]-2-(3,4,5-trimethoxyphenyl)-tetrahydrofuran.

4-[5-[trans-1-(N-Butyl-N-hydroxyamino)propen-3-yl]-3-methoxy-4-propoxyphenyl]-2-(3,4,5-trimethoxyphenyl)-tetrahydrofuran.

4-[5-[trans-1-(N-hydroxy-N-nicotinoylamino)propen-3-yl]-3-methoxy-4-propoxyphenyl]-2-(3,4,5-trimethoxyphenyl)-tetrahydrofuran.

4-[5-[trans-1-(N-Hydroxy-N-phenylacetylamino)propen-3-yl]-3-methoxy-4-propoxyphenyl]-2-(3,4,5-trimethoxyphenyl)-tetrahydrofuran.

4-[5-[trans-1-(N-Hydroxy-N-3-phenoxybenzoylamino)-propen-3-yl]-3-methoxy-4-propoxyphenyl]-2-(3,4,5-trimethoxyphenyl)-tetrahydrofuran.

4-[5-trans-1-(N-3-Chlorobenzoyl-N-hydroxyamino)propen-3-yl]-3-methoxy-4-propoxyphenyl]-2-(3,4,5-trimethoxyphenyl)-tetrahydrofuran.

4-[5-[trans-1-(N-3-Chlorobenzoyl-N-hydroxyamino-propen-3-yl]-3-methoxy-4-propoxyphenyl]-2-(3,4,5-trimethoxyphenyl)-tetrahydrofuran.

4-[5-[trans-1-(N-2,4-Difluorobenzoyl-N-hydroxyamino)Propen-3-yl]-3-methoxy-4-propoxyphenyl]-2-(3,4,5-trimethoxyphenyl)-tetrahydrofuran.

4-[5-[trans-1-(N-Hydroxy-N-3,4-methylenedioxybenzoylamino)propen-3-yl]-3-methoxy-4-propoxyphenyl]-2-(3,4,5-trimethoxyphenyl)-tetrahydrofuran.

and also the corresponding saturated hydroxamates, e.g., 4-[5-[1-(-N-Hydroxy N-3,4-methylenedioxybenzoyl-N-hydroxyamino)propyl]-3-methoxy-4-propoxyphenyl]-2-(3,4,5-trimethoxyphenyl)tetrahydrofuran.

Double bonded ureas: Both cis and trans isomer at the tetrahydrofuran ring.

4-[5-[trans-1-(N'-Hydroxy-N'-methylureidyl)propen-3-yl]-3-methoxy-4propoxyphenyl]-2-(3,4,5-trimethoxyphenyl)-tetrahydrofuran.

4-[5-[trans-1-(N'-Ethyl-N'-hydroxyureidyl)propen-3-yl]-3-methoxy-4-propoxyphenyl]-2-(3,4,5-trimethoxyphenyl)-tetrahydrofuran.

4-[5-trans-1-(N'-Hydroxy-N'-propylureidyl)propen-3-yl]-3-methoxy-4-propoxyphenyl]-2-(3,4,5-trimethoxyphenyl)-tetrahydrofuran.

4-[5-[trans-1-(N'-Butyl-N'-hydroxyureidyl)propen-3-yl]-3-methoxy-4-propoxyphenyl]-2-(3,4,5-trimethoxyphenyl)-tetrahydrofuran.

4-[5-[trans-1-(N'-Hydroxy-N'-i-propylureidyl)propen-3-yl]-3-methoxy-4-propoxyphenyl]-2-(3,4,5-trimethoxyphenyl)-tetrahydrofuran.

4-[5-[trans-1-(N'-t-Butyl-N'-hydroxyureidyl)propen-3-yl]-3-methoxy-4-propoxyphenyl]-2-(3,4,5-trimethoxyphenyl)-tetrahydrofuran.

4-[5-[trans-1-(N'-Benzyl-N'-hydroxyureidyl)propen-3-yl]-N-3-methoxy-4-propoxyphenyl]-2-(3,4,5-trimethoxyphenyl)-tetrahydrofuran.

4-[trans-1-(N'-Allyl-N'-hydroxyureidyl)propen-3-yl]-3-methoxy-4-propoxyphenyl]-2-(3,4,5-trimethoxyphenyl)-tetrahydrofuran.

4-[5-[trans-1-(N'-Cyclohexyl-N'-hydroxyureidyl)propen-3-yl]-3-methoxy-4-propoxyphenyl-2-(3,4,5-trimethoxyphenyl)-tetrahydrofuran.

4-[5-[trans-1-(N'-Hydroxy-N'-methylthioethylureidyl)-propen-3-yl]-3-methoxy-4-propoxyphenyl]-2-(3,4,5-trimethoxyphenyl)-tetrahydrofuran.

4-]5-[trans-1-(N'-Cyclohexyl-N'-hydroxyureidyl)propen-3-yl]-3-methoxy-4-propoxy]-2-(3,4,5-trimethoxyphenyl)-tetrahydrofuran.

and also the corresponding saturated ureas, e.g., 4-[5-[1(N'-Cyclohexyl-N'-hydroxyureidyl)propyl]-3-methoxy-4-propoxyphenyl]-2-(3,4,5-trimethoxyphenyl)-tetrahydrofuran.

Formula III cis and trans Isomers of the following compounds 2-(3-Methoxy-4-methoxyethoxy-5-N-methylaminophenyl)-5-(3,4,5-trimethoxyphenyl)-tetrahydrothiophene.

2-(3-Methoxy-4-methoxyethoxy-5-N-ethylaminophenyl)-5-(3,4,5-trimethoxyphenyl)-tetrahydrothiophene.

2-(3-Methoxy-4-methoxyethoxy-5-N,N-dipropylaminophenyl)-5-(3,4,5-trimethoxyphenyl)-tetrahydrothiophene.

2-(3-Methoxy-4-methylthioethoxy-5-N-methylaminophenyl)-5-(3,4,5-trimethoxyphenyl)-tetrahydrofuran.

2-(4-p-Hydroxyphenylthioethoxy-3-methoxy-5-N-methylaminophenyl)-5-(3,4,5-trimethoxyphenyl)-tetrahydrofuran.

2-[3-Methoxy-4-methoxyethoxy-5-(1-pyrrolidinyl) phenyl]-5-(3,4,5-trimethoxyphenyl)-tetrahydrothiophene.

2-(3-Methoxy-4-methoxyethoxy-5-N,N-diethylaminophenyl)-5-(3,4,5-trimethoxyphenyl)-tetrahydrothiophene.

2-[4-p-Cyanophenylthioethoxy-3-methoxy-5-(1-pyrrolidinyl)phenyl]-5-(3,4,5-trimethoxyphenyl)-tetrahydrofuran.

2-(3-Methoxy-4-p-methoxyphenylthioethoxy-5-N,N-dimethylaminophenyl)-5-(3,4,5-trimethoxyphenyl)-terahydrofuran.

2-(3-Methoxy-4-p-cyanophenylthioethoxy-5-N,N-diethylaminophenyl)-5-(3,4,5-trimethoxyphenyl)-tetrahydrothiophene.

2-(4-p-Hydroxyphenylthioethoxy-3-methoxy-5-N-methylaminophenyl)-5-(3,4,5-trimethoxyphenyl)-tetrahydrothiophene.

2-(4-p-Cyanophenylthioethoxy-3-methoxy-5-N,N-dimethylaminophenyl)-5-(3,4,5-trimethoxyphenyl)-tetrahydrothiophene.

2-[3-Methoxy-4-p-methoxyphenylthioethoxy-5-(4-morpholinyl)phenyl]-5-(3,4,5-trimethoxyphenyl)-tetrahydrothiophene.

2-(3-Methoxy-4-p-methoxyphenylthioethoxy-5-N,N-dimethylaminophenyl)-5-(3,4,5-trimethoxyphenyl)-tetrahydrothiophene.

2-(4-p-Cyanophenylthioethoxy-3-methoxy-5-N-methylaminophenyl)-5-(3,4,5-trimethoxyphenyl)-tetrahydrofuran.

2-(4-p-Cyanophenylthioethoxy-3-methoxy-5-N-methylaminophenyl)-5-(3,4,5-trimethoxyphenyl)-tetrahydrothiophene.

2-[4-p-Cyanophenylthioethoxy-3-methoxy-5-(4-morpholinyl)phenyl]-5-(3,4,5-trimethoxyphenyl)-tetrahydrofuran.

2-(3-Methoxy-4-methoxyethoxy-5-N,N-dibutylaminophenyl)-5-(3,4,5-trimethoxyphenyl)-tetrahydrothiophene.

2-(3-Methoxy-4-methylthioethoxy-5-N-methylaminophenyl)-5-(3,4,5-trimethoxyphenyl)-tetrahydrothiophene.

B. Stereochemistry

The 2,5-diaryl tetrahydrofurans, tetrahydrothiophenes, and pyrrolidines, 1,3-cyclopentanes, and the 2,4-diaryl tetrahydrofurans, tetrahydrothiophenes, and pyrrolidines disclosed herein exhibit a number of sterochemical configurations. Carbon atoms 2 and 5 (or 2 and 4, in the compounds of Formula II) in the center ring are chiral, and thus the center ring exists at a minimum as a diastereomeric pair. Each diastereomer exists as a set of enantiomers. Therefore, based on the chiral $C_2$ and $C_5$ (or $C_2$ and $C_4$, in Formula II) atoms alone, the compound is a mixture of four enantiomers.

If nonhydrogen substituents are located on carbon atoms 3 and 4 in the center ring, (or Carbon atoms 3 and 5, in Formula II compounds) then the $C_3$ and $C_4$ atoms are also chiral, and can also exist as a diastereomeric pair, that is again a mixture of four enantiomers.

The R groups in the active compounds described herein can likewise include chiral carbons, and thus, optically active centers.

It is sometimes found that one or more enantiomers of a biologically active compound is more active, and perhaps less toxic, than other enantiomers of the same compound. Such enantiomerically enriched compounds are often preferred for pharmaceutical administration to humans. For example, it has been discovered that trans-2,5-diaryl tetrahydrothiophene and trans-2,5-diaryl tetrahydrofuran are often more active PAF receptor antagonists than their cis counterparts.

One of ordinary skill in the art can easily synthesize and separate the enantiomers of the disclosed compounds using chiral reagents and known procedures, and can evaluate the biological activity of the isolated enantiomer using methods disclosed herein or otherwise known. Through the use of chiral NMR shift reagents, polarimetry, or chiral HPLC, the optical enrichment of the compound can be determined.

Classical methods of resolution include a variety of physical and chemical techniques. Often the simplest and most efficient technique is repeated recrystallization. Recrystallization can be performed at any stage in the preparation of the compound, or the final enantiomeric product. If successful, this simple approach represents a method of choice.

When recrystallization fails to provide material of acceptable optical purity, other methods can be evaluated. If the compound is basic, one can use chiral acids that form diastereomeric derivative that may possess significantly different solubility properties. Nonlimiting examples of chiral acids include malic acid, mandelic acid, dibenzoyl tartaric acid, 3-bromocamphor-8-sulfonic acid, 10-camphorsulfonic acid, and di-p-toluoyl-tartaric acid. Similarly, acylation of a free hydroxyl group with a chiral acid also results in the formation of diastereomeric derivatives whose physical properties may differ sufficiently to permit separation.

Enantiomerically pure or enriched compounds can be obtained by passing the racemic mixture through a chromatographic column that has been designed for chiral separations, including cyclodextrin bonded columns marketed by Rainin Corporation.

A variety of chemical reagents and experimental procedures have been developed in recent years to produce enantiomerically pure or enriched products. For example, individual 2S,5S or 2R,5R enantiomers of 2,5-diaryl tetrahydrofurans can be prepared by the method described by Corey et al. (Corey, E. J. et al., *Tetrahedron Lettes* 29, 2899 (1988)).

C. Synthesis of Active Compounds

The 2,5-diaryl tetrahydrofurans and tetrahydrothiophenes disclosed herein can be prepared in a variety of ways known to those skilled in the art, including by methods disclosed in or obvious in view of methods disclosed in U.S. Pat. Nos. 4,539,332, 4,757,084, 4,996,203 and 5,001,123, and European Patent Application Nos. 90306234.7, 90306235.4, and 89202593.3. Examples 1–14, and corresponding FIGS. 1–6, provide detailed descriptions of the preparation of a number of active 2,5-diaryl tetrahydrofurans and tetrahydrothiophenes.

1,3-Diaryl cyclopentanes can be prepared as described in Example 15 (FIG. 7) following the procedure of Graham, et al. (1.3-Diaryl Cyclopentanes: A New Class of Potent PAF Receptor Antagonists. 197th ACS National Meeting, Dallas, Tex., Apr. 9–14, 1989, Division of Medicinal Chemistry, poster no. 25 (abstract)), or by other known methods.

2,5-Diaryl pyrrolidines can be prepared as described in Example 16 (FIG. 8), or by other methods known to those skilled in the art, including that described by Boekvall, et al. (*J. Org. Chem.* 55, 826 (1990)).

2,4-Diaryl tetrahydrofurans and tetrahydrothiophenes can be prepared as described in detail in Example 17 (FIG. 9), or by other methods known to those skilled in the art. 2,4-Diaryl pyrrolidines can also be prepared by adaptations of methods described herein, or by other known methods.

EXAMPLE 1

Figure 2:
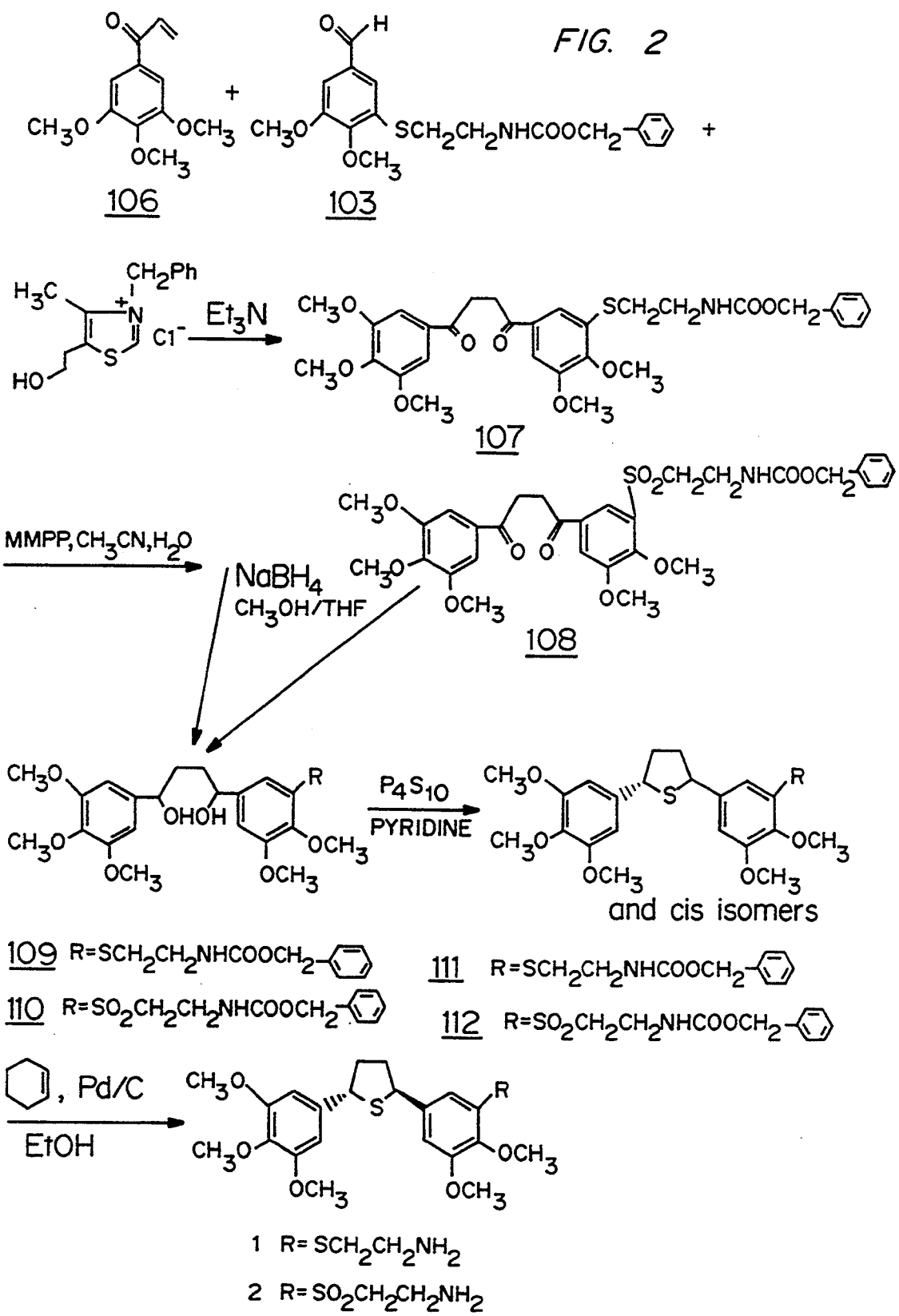
FIG. 2 is a schematic illustration of a process for apreparation of trans-2-(3,4-dimethoxy-5-aminoethylthiophenyl)-5-(3,4,5-trimethoxyphenyl)tetrahydrothiophene (compound 1, FIG. 2) and trans-2-(3,4-dimethoxy-5-aminoethyl sulfonylphenyl)-5-(3,4,5-trimethoxyphenyl)-tetrahydrothiophene (compound 2, FIG. 2).

Preparation of trans-2-(3,4-dimethyl-5-aminoethylthiophenyl)-5-(3,4,5-trimethoxyphenyl)-tetrahydrothiophene (1, FIG. 2)

N,N-Dibenzyloxycarbonyl cystamine (compound 101, FIG. 1)

Cystamine dichloride (18 g, 79.93 mmole) was dissolved in 180 mL of 2N NaOH (14.4 g, 360 mmole). To this solution was added benzyl chloroformate (29.72 g, 174.21 mmole) dropwise at 0° C. A precipitate formed, and the mixture was stirred for 2 hours at 0° C. The precipitate was collected, washed with water and methanol and recrystallized from CHCl$_3$—CH$_3$OH to obtain a white crystalline solid (30.1 g, 89.6%). $^1$H NMR (CDCl$_3$): 2.78 (t, 4H), 3.48 (q, 4H); 5.10 (s, 4H); 5.24 (bs, 2H); 7.34 (s, 10H).

3,4-Dimethoxy-5-iodo-benzaldehyde (compound 102, FIG. 1)

A mixture of 5-iodovanillin (7 g, 25.18 mmole), potassium carbonate (8.78 g, 63.53 mmole) and iodomethane (6.43 g, 45.30 mmole) was suspended in 60 mL of DMF and stirred at room temperature for 14 hours. The reaction mixture was quenched with water and extracted with diethyl ether. The organic layer was dried over MgSO$_4$, filtered and evaporated in vacuo to obtain a solid which was recrystallized from hexane/ethyl acetate (2:1) (6.28 g, 85.4%).

3,4-Dimethoxy-5-N-benzyloxycarbonylethylthiobenzaldehyde (compound 103, FIG. 1)

A suspension of 3,4-dimethoxy-5-iodo-benzaldehyde (6.18 g, 21.16 mmole) and copper (11.55 g, 181.74 mmole) in 50 mL of DMF was heated at 140° C. for 2 hours and N,N-dibenzyloxycarbonyl cystamine (14.19 g, 33.78 mmole) was added. The solution was heated at 140° C. for 40 hours, filtered and the residue washed with ethyl acetate. The combined filtrate was evaporated to leave a solid which was recrystallized from ethyl acetate and hexane (7.05 g, 88.5%).

3-(N,N-Dimethylamino)-1-(3,4,5-trimethoxyphenyl)-1-propane (compound 104, FIG. 1)

3,4,5-Trimethoxyacetophenone (50 g, 237.8 mmole), paraformaldehyde (9.75 g, 304.7 mmole), dimethylamine hydrochloride (26.42 g, 324.0 mmole) and 5 mL conc. HCl were dissolved in 200 mL absolute ethanol and refluxed for 10 hours. Additional dimethylamine hydrochloride (13.21 g, 162.0 mmole) and paraformaldehyde (9.75 g, 304.7 mmole) were added and the solution returned to reflux. After 54 hours (total reaction time), 80 mL of 10% HCl and 500 mL of water were added and the solution was extracted with ethyl ether. The acidic aqueous layer was adjusted to pH 10 with 10% NaOH. The basic solution was extracted with ethyl acetate, dried over MgSO$_4$, filtered and evaporated in vacuo to provide 57.5 g of a yellow oil (92%). $^1$H NMR (CDCl$_3$): 2.30 (s, 6H); 2.74 (t, 2H); 3.11 (t, 2H); 3.91 (s, 9H); 7.23 (s, 1H); 7.32 (s, 1H).

3-(N,N,N-Trimethylamino-1-(3,4,5-trimethoxyphenyl)-1-propanone iodide (compound 105, FIG. 1)

3-(N,N,N-Dimethylamino-1-(3,4,5-trimethoxyphenyl)-1-propanone (57 g, 213.5 mmole) was dissolved in 200 mL of anhydrous diethyl ether. To this solution was added methyl iodide (57.6 g, 405.7 mmole). A white precipitate formed immediately, and the reaction stirred at room temperature for an additional 2 hours. The product was isolated by suction filtration (83.8 g, 96%).

3,4,5-Trimethoxyphenylvinylketone (compound 106, FIG. 1)

3-(N,N,N-Trimethylamino-1-(3,4,5-trimethoxyphenyl)-1-propanone iodide (30 g, 73.3 mmole) and potassium carbonate (16.0 g, 115.9 mmole) were suspended in acetone (500 mL). The solution was stirred overnight at room temperature and then heated at reflux for 5 hours. The solution was then filtered, and evaporated to an oil which was purified by flash column chromatography using 1:1 hexane/ethyl acetate as solvent (9.2 g, 56.4%). $^1$H NMR (CDCl$_3$): 3.92 (s, 9H); 5.92 (d, 1H); 6.44 (d, 1H); 7.12 (m, 1H); 7.22 (s, 2H).

1-(3,4-Dimethoxy-5-N-benzyloxycarbonylethylthiophenyl)-4-(3,4,5-trimethoxyphenyl)-1,4-butanedione (compound 107, FIG. 2)

Freshly prepared 3,4,5-trimethoxyphenylvinylketone (8.46 g, 38.11 mmole), 3,4-dimethoxy-5-N-benzyloxycarbonylethylthiobenzaldehyde (7.05 g, 18.8 mmole), 3-benzyl-5-(2-hydroxyethyl)-4-methyl-thiazolium chloride (2.0 g, 7.41 mmole) and 32 ml of trimethylamine were stirred at 65° C. overnight. The reaction was quenched with water, acidified with 10% HCl and extracted with chloroform. The organic layer was washed with saturated aqueous sodium chloride, dried over MgSO$_4$, filtered and evaporated in vacuo to an oil that was purified by flash column chromatography using 1:1 hexane/ethyl acetate as eluent (8.36 g, 76.7%). $^1$H NMR (CDCl$_3$): 3.10 (t, 2H); 3.45 (m, 6H); 3.90 (s, 3H); 3.93 (s, 9H); 3.94 (s, 3H); 5.08 (s, 2H); 5.30 (bt, 1H); 7.29 (s, 2H); 7.33 (s, 5H); 7.46 (d, 1H); 7.72 (d, 1H).

1-(3,4-Dimethoxyphenyl-5-N-benzyloxy carbonylethylthiophenyl)-4-(3,4,5-trimethoxyphenyl)-1,4-butanediol (compound 109, FIG. 2)

1-(3,4-Dimethoxy-5-N-benzyloxycarbonylethylthiophenyl)-4-(3,4,5-trimethoxyphenyl)-1,4-butanedione (2.26 g, 5.16 mmole) was dissolved in 23 mL of THF and the solution was diluted with 36 mL of methanol. To this solution was added sodium borohydride (264.9 mg, 9.29 mmole) in 10 mL of water dropwise, and the solution stirred at room temperature for 2.5 hours. The reaction mixture was then cooled, quenched with water, and extracted with chloroform. The organic layer was dried over MgSO$_4$, filtered and evaporated in vacuo to provide 2.21 g of diol (97.6%).

2-(3,4-Dimethoxy-5-N-benzyloxycarbonyl ethylthiophenyl)-5-(3,4,5-trimethoxyphenyl)tetrahydrothiophene (compound 111, FIG. 2)

1-(3,4-Dimethoxy-5-N-benzyloxycarbonylethylthiophenyl)-4-(3,4,5-trimethoxyphenyl)-1,4-butanediol (2.66 g, 4.547 mmole) and 2.6 g of P$_4$S$_{10}$ were dissolved in 30 mL pyridine and heated at 90° C. for 16 hours. The solvent was removed by distillation in vacuo and the residue was acidified with 10% HCl and extracted with dichloromethane. The organic layer was washed with 10% HCl, water and saturated aqueous sodium chloride, dried over MgSO$_4$, filtered and evaporated to give a gummy residue that was purified by flash column chromatography using 2:1 hexane/ethyl acetate as solvent and then by HPLC using hexane and ethyl acetate as solvent.

trans-2-(3,4-Dimethoxy-5-N-aminoethyl thiophenyl)-5-(3,4,5-trimethoxyphenyl)-tetrahydrothiophene (compound 1, FIG. 2)

Compound 1 is prepared from 2-(3,4-dimethoxy-5-N-benzyloxycarbonylethylthiophenyl)-5-(3,4,5-trimethoxyphenyl)tetrahydrothiophene by treatment with KOH (5 equivalents) in ethylene glycol at 100 °C. for 20 hours. The mixture is quenched with water and extracted with an organic solvent. The organic layer is dried, and evaporated to leave a solid that is purified by chromatography.

EXAMPLE 2

Preparation of trans-2-(3,4-Dimethoxy-5-aminoethylsulfonylphenyl)-5-(3,4,5-trimethoxyphenyl)tetrahydrothiophene (compound 2, FIG. 2)

Figure 3:
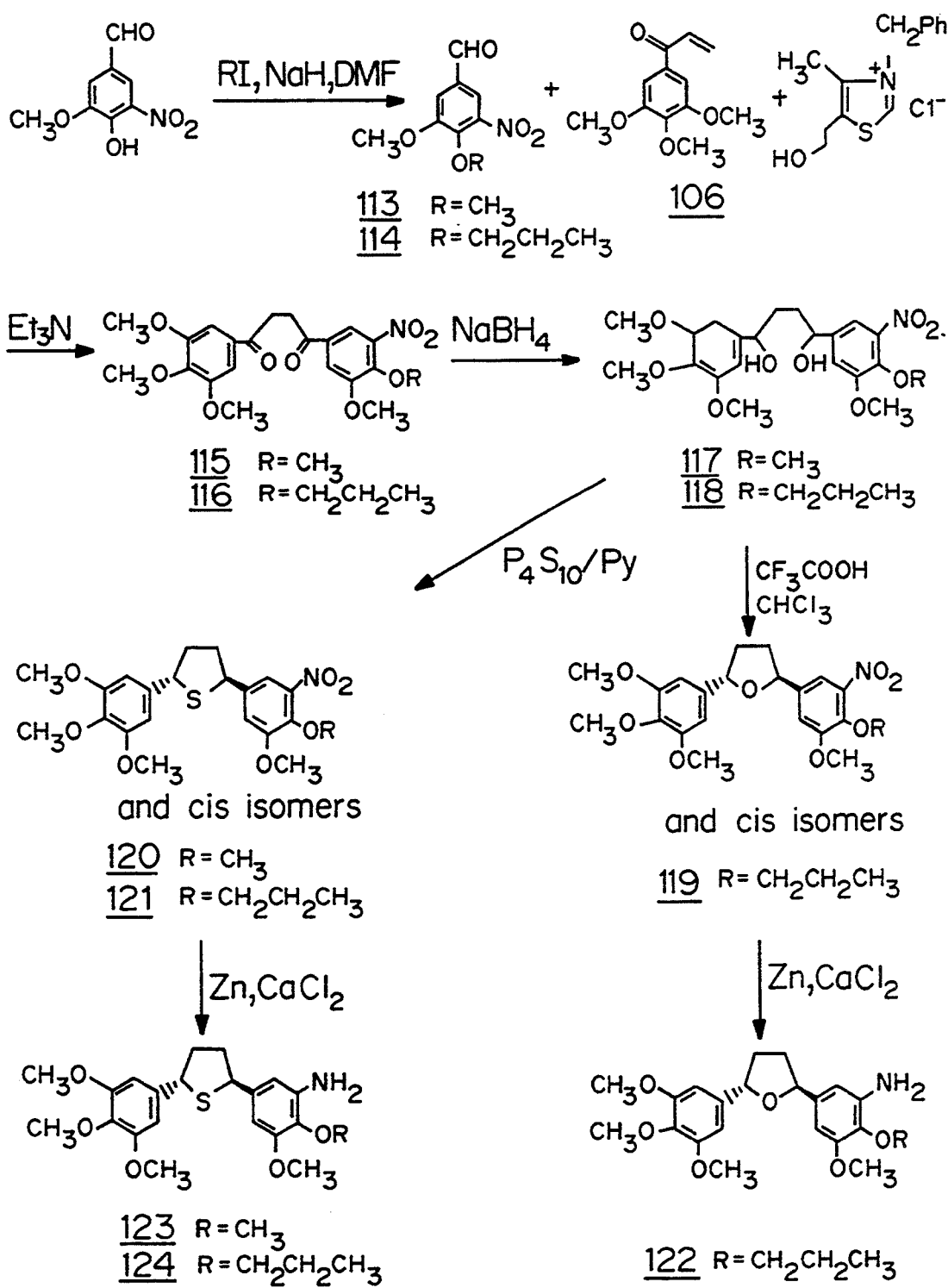
FIG. 3 is a schematic illustration of a process for a preparation of trans-2-(3-methoxy-4-propoxy-5-aminophenyl)-5-(3,4,5-trimethoxyphenyl)-tetrahydrofuran (compound 122, FIG. 3), trans-2-(3,4-dimethoxy-5-aminophenyl)-5-(3,4,5-trimethoxyphenyl)-tetrahydrothiophene (compound 123, FIG. 3), and trans-2-(3-methoxy-4-propoxy-5-aminophenyl)-5-(3,4,5-trimethoxyphenyl)tetrahydrothiophene compound 124, FIG. 3).

1-(3,4-Dimethoxy-5-N-benzyloxycarbonylethylsulfonylphenyl)-4-(3,4,5-trimethoxyphenyl)-1,4-butanedione (Compound 108, FIG. 3)

A solution of magnesium monoperoxyphthalic acid (MMPP, 5.98 g, 9.68 mmole) in water (15 mL) was added to a solution of 1-(3,4-dimethoxy-5-benzyloxycarbonylethylthiophenyl)-4-(3,4,5-trimethoxyphenyl)-1,4-butanedione (3 g, 5.16 mmole) in 40 mL of acetonitrile at room temperature. The solution was stirred at room temperature for 2 hours, and then water added, and the mixture extracted with dichloromethane. The organic layer was washed with 1N NaOH, water and then saturated aqueous NaCl, filtered and evaporated in vacuo to a solid that was recrystallized in ethyl acetate and hexane to provide 2.97 g of dione (93.7%).

1-(3,4-Dimethoxy-5-N-benzyloxycarbonylethylsulfonylphenyl)-4-(3,4,5-trimethoxyphenyl)-1,4-butanediol (compound 110, FIG. 2)

1-(3,4-Dimethoxy-5-N-benzyloxycarbonylethylsulfonylphenyl)-1,4-butanedione (2.87 g, 4.68 mmole) was dissolved in 20 mL THF and the solution diluted with 32 mL methanol. To this solution was added sodium borohydride (318.8 mg, 8.43 mmole) in 9 mL dropwise, and the solution stirred at room temperature for 2.5 hours. The solution was cooled and quenched with water, the aqueous layer extracted with dichloromethane and the organic layer dried over MgSO$_4$, filtered and evaporated in vacuo to provide 2.86 g of diol (99%).

trans-2-(3,4-Dimethoxy-5-N-benzyloxy carbonylethylsulfonylphenyl)-5-(3,4,5-trimethoxyphenyl) tetrahydrothiophene (compound 112, FIG. 2)

1-(3,4-Dimethoxy-5-N-benzyloxycarbonylethylsulfonylphenyl)-4-(3,4,5-trimethoxyphenyl)-1,4-butanediol (2.8 g, 4.54 mmole) was dissolved in 25 mL pyridine and treated with 2.82 g of P$_4$S$_{10}$ and then heated at 90° C. for 16 hours. The solvent was removed by distillation in vacuo, and the residue was acidified with 10% HCl and extracted with dichloromethane. The organic layer was washed with 10% HCl, water, and saturated sodium chloride solution, dried over MgSO$_4$, filtered and then evaporated to give a gummy residue that was purified by flash chromatography with 1:1 hexane:ethyl acetate, followed by HPLC using hexane and ethyl acetate as solvent (yield 34 mg). $^1$H NMR (CDCl$_3$): 2.09 (m, 2H); 2.60 (m, 2H); 3.60 (m, 4H); 3.82 (s, 3H); 3.90 (s, 6H); 3.92 (s, 3H); 3.96 (s, 3H); 4.81 (m, 2H); 5.09 (s, 2H); 5.49 (bs, 1H); 6.70 (s, 2H); 7.34 (d, 1H); 7.35 (s, 5H); 7.56 (d, 1H).

trans-2-(3,4-Dimethoxy-5-aminoethyl sulfonylphenyl)-5-(3,4,5-trimethoxyphenyl)-tetrahydrothiophene (compound 2, FIG. 2)

trans-2-(3,4-Dimethoxy-5-benzyloxycarbonylethylsulfonylphenyl)-5-(3,4,5-trimethoxyphenyl)-tetrahydrothiophene (32.6 mg, 0.052 mmole) was dissolved in 3 mL ethanol. To this solution was added 1.2 mL cyclohexene and 46.9 mg 10% Pd-C catalyst. The mixture was refluxed for 2 hours, and then the catalyst removed by filtration. The catalyst was washed with ethanol, and the combined filtrate evaporated under reduced pressure to an oil that was purified by flash chromatography using hexane/ethyl acetate (1:1) followed by chloroform/acetone (4:1) to provide 4.1 mg product. $^1$H NMR (CDCl$_3$): 2.09 (m, 2H); 2.60 (m, 2H); 2.68 (t, 2H); 3.10 (bs, 2H); 3.45 (t, 2H); 3.82 (s, 3H); 3.89 (s, 6H); 3.93 (s, 3H); 3.97 (s, 3H); 4.81 (m, 2H); 6.70 (s, 2H); 7.30 (s, 1H); 7.50 (s, 1H).

EXAMPLE 3

Figure 4:
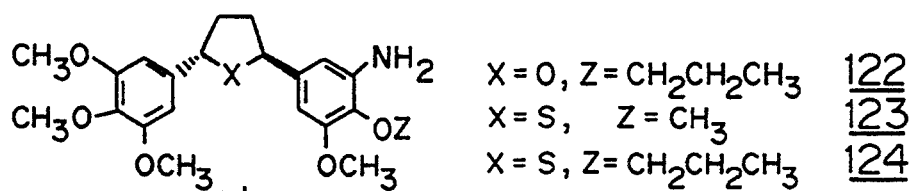
FIG. 4 is a schematic illustration of a process for the preparation of trans-2-(3-methoxy-4-propoxy-5-benzylaminophenyl)-5-(3,4,5-trimethoxyphenyl) tetrahydrofuran (compound 3, FIG. 4), trans-2-(3-methoxy-4-propoxy-5-hydroxyethylaminophenyl)-5-(3,4,5-trimethoxyphenyl)-tetrahydrofuran (compound 4, FIG. 4), trans-2-(3-methoxy-4-propoxy-5-N,N-diallylaminophenyl)-5-(3,4,5-trimethoxyphenyl)-tetrahydrofuran (compound 5, FIG. 4), trans-2-(3,4-dimethoxy-5-benzylaminophenyl)-5-(3,4,5-trimethoxyphenyl)-tetrahydrothiophene (compound 6, FIG. 4), trans-2-(3-methoxy-4-propoxy-5-benzylaminophenyl)-5-(3,4,5-trimethoxyphenyl)-tetrahydrothiophene (compound 7, FIG. 4), trans-2-(3,4,5-dimethoxy-5-hydroxyethylaminophenyl)-5-(3,4,5-trimethoxyphenyl)tetrahydrothiophene (compound 8, FIG. 4), trans-2-(3-methoxy-4-propoxy-5-hydroxethylaminophenyl)-5-(3,4,5-trimethoxyphenyl)-tetrahydrothiophene (compound 9, FIG. 4), trans-2-(3,4-dimethoxy-5-N-diallylaminophenyl)-5-(3,4,5-trimethoxyphenyl)-tetrahydrothiophene (compound 10, FIG. 4), and trans-2-(3-methoxy-4-propoxy-5-N,N-diallylaminophenyl)-5-(3,4,5-trimethoxyphenyl)tetrahydrothiophene (compound 11, FIG. 4), and cis- and trans-2-[5-(N'-substituted-N'-substituted ureidyl)-3-methoxy-4-propoxyphenyl]-5-(3,4,5-trimethoxyphenyl)tetrahydrofuran or tetrahydrothiophene (compounds 12-32 and 38-41, FIG. 4).
Figure 4:
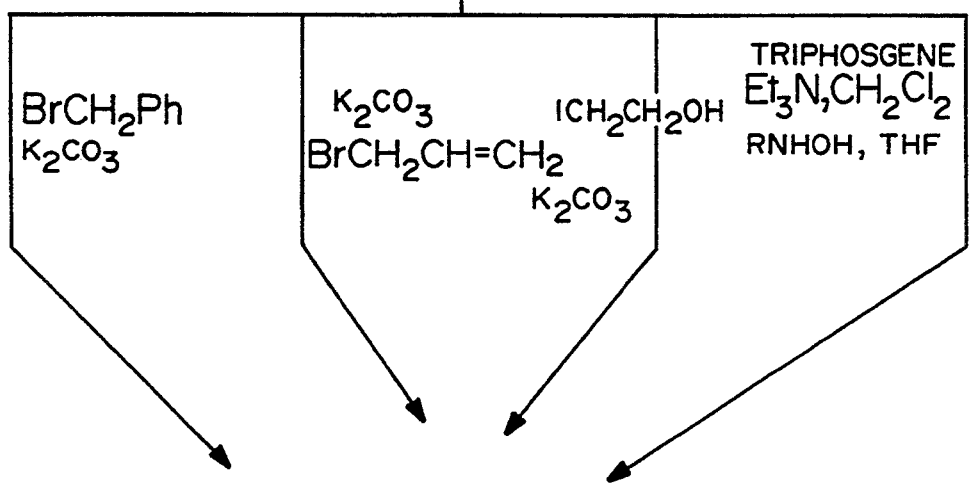
Figure 4:
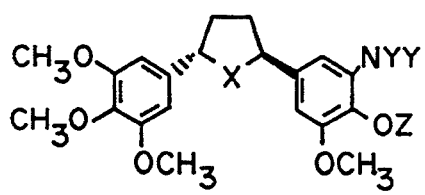

Preparation of trans-2-(3-Methoxy-4-propoxy-5-N-benzylaminophenyl)-5-(3,4,5-tri-methoxyphenyl)-tetrahydrofuran (compound 3, FIG. 4)

3-Methoxy-4-propoxy-5-nitrobenzaldehyde (compound 114, FIG. 3)

A mixture of sodium hydride (6.09 g, 152.3 mmole) in 20 mL of dry dimethylformamide (DMF) was cooled to 0° C. and then 5-nitrovanillin (25 g, 126.8 mmole) in 41 mL of DMF was added dropwise. After 30 minutes, propyl iodide (25.87 g, 152.0 mmole) was added dropwise at 0° C. When the addition was completed, the reaction was maintained at room temperature for 2 hours and then stirred overnight at 70° C. Water was added, and the solution extracted with ethyl ether, washed with 10% NaOH, dried over MgSO$_4$, filtered and then evaporated in vacuo to an oil (19 g, 62.7%).

1-(3-Methoxy-4-propoxy-5-nitrophenyl)-4-(3,4,5-trimethoxyphenyl)-1,4-butanedione (compound 116, FIG. 3)

A solution of 3,4,5-trimethoxyphenylvinylketone (13.25 g, 59.64 mmol), 3-methoxy-4-propoxy-5-nitrobenzaldehyde (11.95, 50 mmole), 3-benzyl-5-(2-hydroxyethyl)-4-methylthiazolium chloride (5.36 g, 19.91 mmole) and triethylamine (50 mL) were stirred at 60° C. overnight, and then quenched with water, acidified with 10% HCl and extracted with chloroform. The organic layer was washed with saturated aqueous sodium chloride, dried over magnesium sulfate, filtered and evaporated in vacuo to an yellow oil that was purified by flash chromatography using 2:1 hexane/ethyl acetate as the solvent to yield a white solid (9.59 g, 41.6%). $^1$H NMR (CDCl$_3$): 1.07 (t, 3H), 1.86 (m, 2H), 3.40 (d, 4H), 3.88 (s, 3H), 3.92 (s, 9H), 4.04 (t, 2H), 7.29 (s, 2H), 7.54 (d, 1H), 8.07 (d, 1H).

1-(3-Methoxy-4-propoxy-5-nitrophenyl)-4-(3,4,5-trimethoxyphenyl)-1,4-butanediol (compound 118, FIG. 3)

To a solution of 1-(3-methoxy-4-propoxy-5-nitrophenyl)-4-(3,4,5-trimethoxyphenyl)-butane-1,4-dione (11.53 g, 25 mmole) in 350 mL of methanol and 250 mL of tetrahydrofuran was added dropwise a solution of sodium borohydride (3.076 g, 81.34 mmol) in 140 mL of water. After the addition was completed, the mixture was stirred at room temperature for 3 hours, quenched with water and extracted with dichloromethane. The organic layer was dried over magnesium sulfate, filtered and evaporated to provide a foam (11.53 g, 99.24%). $^1$H NMR (CDCl$_3$): 1.05 (t, 3H), 1.80–1.95 (m, 6H), 3.80–3.98 (m, 12H), 4.1 (t, 2H), 4.72 (m, 2H), 6.6 (s, 2H), 7.15 (s, 1H), 7.35 (s, 1H).

2-(3-Methoxy-4-propoxy-5-nitrophenyl)-5-(3,4,5-trimethoxyphenyl)-tetrahydrofuran (compound 119, FIG. 3)

A suspension of P$_4$S$_{10}$ (19.25 g, 43.3 mmol) in 250 mL of pyridine was heated at 120° C. for 75 minutes. To this suspension was then added a solution of 1-(3-methoxy-4-propoxy-5-nitrophenyl)-4-(3,4,5-trimethoxyphenyl)-butane-1,4-diol (4.65 g, 10 mmol) in 50 mL of pyridine. The temperature was reduced to 90° C. and stirring continued for an additional 90 minutes. After cooling, ice and water were added, the mixture was extracted with methylene chloride. The organic layer was washed with water, 5% HCl, water, sodium bicarbonate and saturated aqueous sodium chloride, and then dried over magnesium sulfate, filtered and evaporated.

The mixture of cis and trans compounds were separated by HPLC using Water's prep Nova-Pak HR silica cartridge (9:1 hexane: ethyl acetate) to provide 300 mg (6.5%) trans and 250 mg (5.42%) of cis isomer. Trans isomer. $^1$H NMR (CDCl$_3$): 1.05 (t, 3H), 1.80–1.90 (m, 2H), 2.10–2.20 (m, 2H), 2.60–2.70 (m, 2H), 3.85–3.95 (m, 12H), 4.10 (t, 2H), 4.85 (m, 2H), 6.75 (s, 2H), 7.20 (d, 1H), 7.45 (d, 1H). Cis isomer. $^1$H NMR (CDCl$_3$): 1.05 (t, 3H), 1.80–1.90 (m, 2H), 2.10–2.20 (m, 2H), 2.60–2.70 (m, 2H), 3.85–3.95 (m, 12H), 4.10 (t, 2H), 4.70 (m, 2H), 6.75 (s, 2H), 7.20 (d, 1H), 7.45 (d, 1H).

trans-2-(3-Methoxy-4-propoxy-5-aminophenyl)-5-(3,4,5-trimethoxyphenyl) tetrahydrofuran (compound 122, FIG. 3)

trans-2-(3-Methoxy-4-propoxy-5-nitrophenyl)-5-(3,4,5 trimethoxyphenyl)-tetrahydrofuran (2.235 g, 5 mmol) was dissolved in 45 mL of absolute ethanol. To this solution was added calcium chloride (0.5 g, 5 mmol) in 10 mL of water followed by freshly activated zinc dust (7.5 g). The mixture was refluxed for 12 hours, and the solid then removed by vacuum filtration through Celite. The filtrate was washed with water, dried over magnesium sulfate, and evaporated in vacuo to a white foam (2.085 g, 97.28%).

trans isomer. $^1$H NMR: (CDCl$_3$): 1.10 (t, 3H), 1.80–1.90 (m, 2H), 2.00–2.15 (m, 2H), 2.50–2.60 (m, 2H), 3.80–3.97 (m, 12H), 4.10 (t, 2H), 5.20–5.35 (m, 2H), 6.45 (s, 1H), 6.55 (s, 1H), 6.75 (s, 2H).

The cis product can be obtained in the same manner as described above using cis-3-(3,4,5-trimethoxyphenyl)-2-(3-methoxy-4-propoxy-5-nitrophenyl)-tetrahydrofuran as the starting material.

Cis isomer. $^1$H NMR: (CDCl$_3$): 1.10 (t, 3H), 1.80–1.90 (m, 2H), 2.00–2.15 (, 2H), 2.50–2.60 (m, 2H), 3.80–3.97 (m, 12H), 4.10 (t, 2H), 5.10–5.20 (m, 2H), 6.45 (s, 1H), 6.55 (s, 1H), 6.75 (s, 2H).

trans-2-(3-Methoxy-4-propoxy-5-benzylaminophenyl)-5-(3,4,5-trimethoxyphenyl)-tetrahydrofuran (compound 3, FIG. 4)

trans-4-(3-Methoxy-4-propoxy-5-nitrophenyl)-5-(3,4,5-trimethoxyphenyl)-tetrahydrofuran (50 mg, 0.12 mmole) and potassium carbonate (1.0 g) were suspended in 2 mL of DMF. Benzyl bromide (205.1 mg, 1.2 mmole) was added and the suspension was stirred at room temperature for 20 hours. The reaction was quenched with water and extracted with dichloromethane. The organic layer was dried over MgSO$_4$, filtered and evaporated in vacuo to an oil that was purified by column chromatography with hexane/ethyl acetate solvent (yield 50.2 mg, 82.6%). $^1$H NMR (CDCl$_3$): 1.05 (t, 3H); 1.83 (m, 4H); 2.32 (m, 2H); 3.85 (s, 3H); 3.90 (s, 6H); 3.91 (s, 3H); 4.05 (t, 2H); 4.28 (d, 2H); 4.67 (bs, 1H); 5.08 (m, 2H); 6.42 (s, 1H); 6.57 (s, 1H); 6.65 (s, 1H); 7.20 (m, 5H).

EXAMPLE 4

Preparation of trans-2-(3-Methoxy-4-propoxy-5-hydroxyethylaminophenyl)-5-(3,4,5-trimethoxyphenyl)-tetrahydrofuran (compound 4, FIG. 4)

A mixture of trans-2-(3-methoxy-4-propoxy-5-aminophenyl)-5-(3,4,5-trimethoxyphenyl) tetrahydrofuran (20 mg. 0.048 mmol), potassium carbonate (0.4 g), and 2-iodoethanol (82.47 mg, 0.48 mmol) was suspended in 2 mL of DMF. The reaction mixture was stirred at room temperature for 20 hours, quenched with water and extracted with dichloromethane. The organic layer was dried over magnesium sulfate, filtered and evaporated in vacuo to an oil which was purified by column using 3:1 hexane/ethyl acetate as solvent (12.8 mg, 57.9%). $^1$H NMR (CDCl$_3$): 1.02 (t, 3H), 1.79 (m, 2H), 1.99 (m, 2H), 2.43 (m, 2H), 3.33 (m, 2H), 3.81 (m, 2H), 3.82 (s, 3H), 3.83 (s, 3H), 3.88 (s, 6H), 3.90 (t, 2H), 5.18 (m, 2H), 6.40 (d, 2H), 6.61 (s, 2H).

EXAMPLE 5

Preparation of trans-2-(3-Methoxy-4-propoxy-5-N,N-diallylphenyl)-5-(3,4,5-trimethoxyphenyl)-tetrahydrofuran (compound 5, FIG. 4)

A mixture of trans-2-(3-methoxy-4-propoxy-5-aminophenyl)-5-(3,4,5-trimethoxyphenyl) tetrahydrofuran (20 mg, 0.048 mmol), potassium carbonate (0.4 g), and 2-allyliodide (80.56 mg, 0.48 mmol) was suspended in 2 mL of DMF. The reaction mixture was stirred at room temperature for 20 hours, and then quenched with water and extracted with dichloromethane. The organic layer was dried over magnesium sulfate, filtered and evaporated in vacuo to an oil which was purified by column using 4:1 hexane/ethyl acetate as solvent (5.1 mg, 21.4%). $^1$H NMR (CDCl$_3$): 1.02 (t, 3H), 1.79 (m, 2H), 1.99 (m, 2H), 2.43 (m, 2H), 3.81 (m, 2H), 3.85 (s, 3H), 3.87 (s, 6H), 3.89 (s, 3H), 3.90 (m, 2H), 5.10–5.20 (m, 6H), 5.80 (m, 2H), 6.57 (s, 1H), 6.63 (s, 2H), 6.63 (s, 1H).

EXAMPLE 6

Preparation of trans-2-(3,4-Dimethoxy-5-N-benzylaminophenyl)-5-(3,4,5-trimethoxyphenyl)-tetrahydrothiophene (compound 6, FIG. 4)

3,4-Dimethoxy-5-nitrobenzaldehyde (compound 113, FIG. 3)

A suspension of sodium hydride (4.87 g, 121.7 mmole) in 18 mL dry DMF was cooled to 0° C. and then 5-nitrovanillin (20 g, 101.4 mmole) in 30 mL of DMF was added dropwise. After 30 minutes, methyl iodide (43.18 g, 304.2 mmole) was added dropwise at 0° C. When the addition was completed, the mixture was warmed to room temperature and stirred overnight. Water was added and the solution extracted with ethyl ether, the organic layer was washed with 10% NaOH solution, dried over MgSO$_4$, filtered and evaporated in vacuo to an oil (8.7 g, 40.7%).

1-(3,4-Dimethoxy-5-nitrophenyl)-4-(3,4,5-trimethoxyphenyl)-1,4-butanedione (compound 115, FIG. 3)

A mixture of freshly prepared 3,4,5-trimethoxyphenylvinylketone (7.12 g, 32.08 mmole), 3,4-dimethoxy-5-nitrobenzaldehyde (5.64 g, 26.73 mmole), 3-benzyl-5-(2-hydroxyethyl)-4-methylthiazolium chloride (2.79 g, 10.69 mmole) and triethylamine (28 mL) were stirred at 65° C. overnight. The reaction was quenched with water, acidified with 10% HCl and extracted with dichloromethane. The organic layer was washed with saturated aqueous sodium chloride, dried over MgSO$_4$, filtered and evaporated to an oil which was purified by flash column chromatography using 1:1 hexane and ethyl acetate as eluent (4.71 g, 40.7%).

1-(3,4-Dimethoxy-5-nitrophenyl)-4-(3,4,5-trimethoxyphenyl)-1,4-butanediol (compound 117, FIG. 3)

1-(3,4-Dimethoxy-5-nitrophenyl)-4-(3,4,5-trimethoxyphenyl)-1,4-butanedione (4.65 g, 10.74 mmole) was dissolved in 40 mL THF and the solution was diluted with 75 mL of methanol. To this solution sodium borohydride (0.73 g, 19.33 mmole) in 20 mL of water was added dropwise. The solution was stirred at room temperature for 2.5 hours, and the reaction mixture cooled, quenched with water, and the aqueous layer extracted with dichloromethane. The organic layer was dried over MgSO$_4$, filtered and evaporated in vacuo to provide 4.61 g of product (98.3%).

2-(3,4-Dimethoxy-5-nitrophenyl)-5-(3,4,5-trimethoxyphenyl)-tetrahydrothiophene (compound 120, FIG. 3)

1-(3,4-Dimethoxy-5-nitrophenyl)-4-(3,4,5-trimethoxyphenyl)-1,4-butanediol (4.61 g, 10.55 mmole) and 6.57 g of P$_4$S$_{10}$ were suspended in 60 mL of pyridine and heated at 90° C. for 16 hours. The solvent was removed by distillation in vacuo. The residue was acidified with 10% HCl and extracted with dichloromethane. The organic layer was washed with 10% HCl, water and saturated aqueous sodium chloride, dried over MgSO$_4$, filtered and evaporated to give a gummy residue that was purified by flash chromatography using 3:1 hexane/ethyl acetate as the solvent (335.6 mg, 7.3%). $^1$H NMR (CDCl$_3$): 2.08 (m, 2H); 2.60 (m, 2H); 3.82 (s, 3H); 3.90 (s, 6H); 3.95 (s, 3H); 3.98 (s, 6H); 4.81 (m, 2H); 6.70 (s, 2H); 7.22 (d, 1H); 7.44 (d, 1H).

trans-2-(3,4-Dimethoxy-5-aminophenyl)-5-(3,4,5-trimethoxyphenyl)-tetrahydrothiophene (compound 123, FIG. 3)

trans-2-(3,4-Dimethoxy-5-nitrophenyl)-5-(3,4,5-trimethoxyphenyl)-tetrahydrothiophene (0.3 g, 0.69 mmole) was suspended in 10 ml of ethanol. To this was added CaCl$_2$ (72.63 mg, 0.65 mmole) in 2 mL water, followed by zinc metal (1.01 g). The suspension was refluxed for 5 hours, filtered, and the residue was washed with ethanol. The combined filtrate was washed with 10% NaHCO$_3$, water and saturated aqueous sodium chloride, dried over MgSO$_4$ and evaporated in vacuo to an oil that was purified by flash column chromatography using 1:1 hexane/ethyl acetate as solvent (30 mg, 10.8%). $^1$H NMR (CDCl$_3$): 2.10 (m, 2H); 2.57 (m, 2H); 3.81 (s, 3H); 3.83 (s, 3H); 3.87 (s, 3H); 3.89 (s, 6H); 4.80 (m, 2H); 6.45 (d, 1H); 6.51 (d, 1H); 6.70 (s, 2H).

trans-2-(3,4-Dimethoxy-5-benzylaminophenyl-5-(3,4,5-trimethoxyphenyl)-tetrahydrothiophene (compound 6, FIG. 4)

trans-2-(3,4-Dimethoxy-5-aminophenyl)-5-(3,4,5-trimethoxyphenyl)-tetrahydrofuran (10 mg, 0.025 mmole) and potassium carbonate (0.2 g) were suspended in 1 mL of DMF. To this solution was added benzyl bromide (42.23 mg, 0.25 mmole). The mixture was stirred at room temperature for 20 hours, quenched with water and then extracted with dichloromethane. The organic layer was dried over MgSO$_4$, filtered and evaporated in vacuo to an oil that was purified by column chromatography using hexane/ethyl acetate (3:1).

EXAMPLE 7

Preparation of trans-2-(3-Methoxy-4-propoxy-5-benzylaminophenyl)-5-(3,4,5-trimethoxyphenyl) tetrahydrothiophene (Compound 7, FIG. 4)

3-Methoxy-4-propoxy-5-nitrobenzaldehyde (compound 114, FIG. 4), 1-(3-methoxy-4-propoxy-5-nitrophenyl)-4-(3,4,5-trimethoxyphenyl)-1,4-butanedione (compound 116, FIG. 4), and 1-(3-methoxy-4-propoxy-5-nitrophenyl)-4-(3,4,5-trimethoxyphenyl)-1,4-butanediol (compound 118, FIG. 4) were prepared as described in Example 3.

2-(3-Methoxy-4-propoxy-5-nitrophenyl)-5-(3,4,5-trimethoxyphenyl)-tetrahydrothiophene (compound 121, FIG. 3)

Compound 121 was prepared in the same way as compound 120 (Example 6), using compound 118 as the starting material.

trans-2-(3-Methoxy-4-propoxy-5-aminophenyl)-5-(3,4,5-trimethoxyphenyl)-tetrahydrothiophene (compound 124, FIG. 3)

Compound 124 was prepared in the same way as compound 123 (Example 6), using compound 121 as the starting material.

trans-2-(3-Methoxy-4-propoxy-5-benzylaminophenyl)-5-(3,4,5-trimethoxyphenyl)-tetrahydrothiophene (Compound 7, FIG. 4)

trans-2-(3-Methoxy-4-propoxy-5-aminophenyl)-5-3,4,5-trimethoxyphenyl)-tetrahydrothiophene (10 mg, 0.023 mmole) and potassium carbonate (0.2 g) were suspended in 1 mL DMF. To this mixture was added benzyl bromide (39.50 mg, 0.23 mmole). The mixture was stirred at room temperature for 20 hours, quenched with water, and then extracted with dichloromethane. The organic layer was dried over MgSO$_4$, filtered and evaporated in vacuo to an oil that was purified by column chromatography using hexane/ethyl acetate (3:1) as solvent.

EXAMPLE 8 trans-2-(3,4-Dimethoxy-5-N,N-dihydroethylaminophenyl)-5-(3,4,5-trimethoxyphenyl)-tetrahydrothiophene (compound 8, FIG. 4)

Compound 8 was prepared by the method described above for compound 4, using compound 123 as the starting material.

EXAMPLE 9 trans-2-(3-Methoxy-4-propoxy-5-N-hydroxyethylaminophenyl)-5-(3,4,5-trimethoxyphenyl)-tetrahydrothiophene (Compound 9, FIG. 4)

Compound 9 was prepared in the same manner as compound 4, described above, using compound 122 as the starting material.

Figure 5:
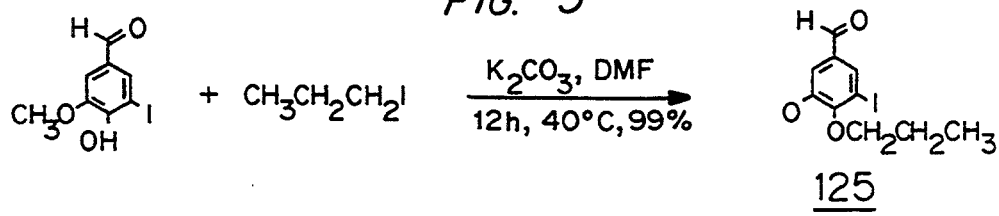
FIG. 5 is a schematic illustration of a process for the preparation of trans-2-(3-methoxy-4-propoxy-5-hydroxyethylsulfonyl)-5-(3,4,5-trimethoxyphenyl)tetrahydrothiophene (compound 38).
Figure 5:
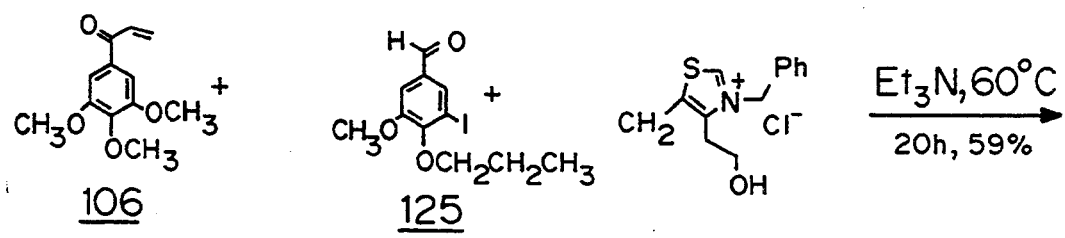
Figure 5:
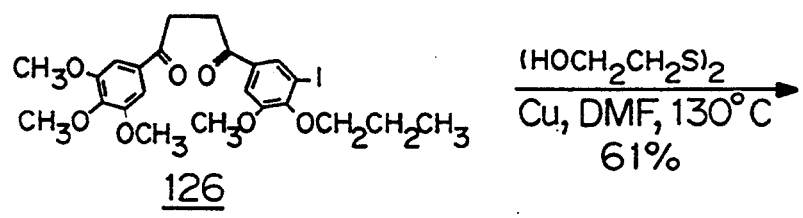
Figure 5:
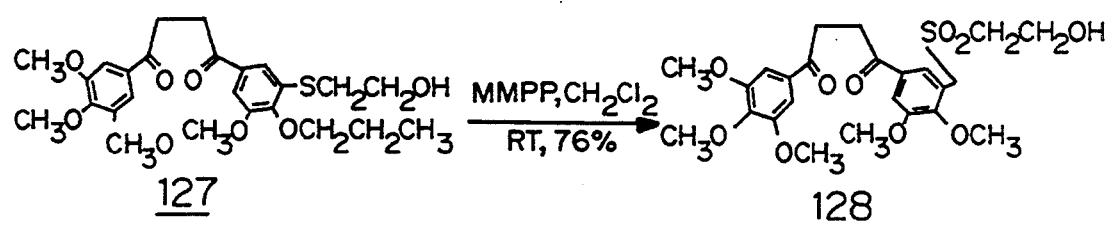
Figure 5:
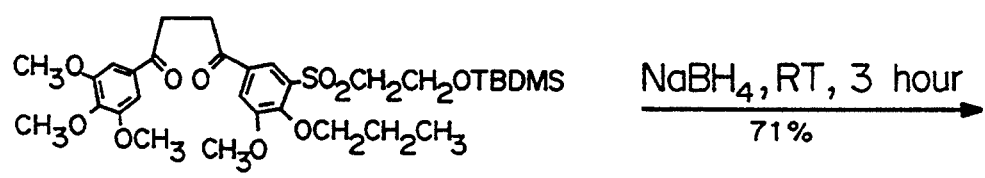
Figure 5:
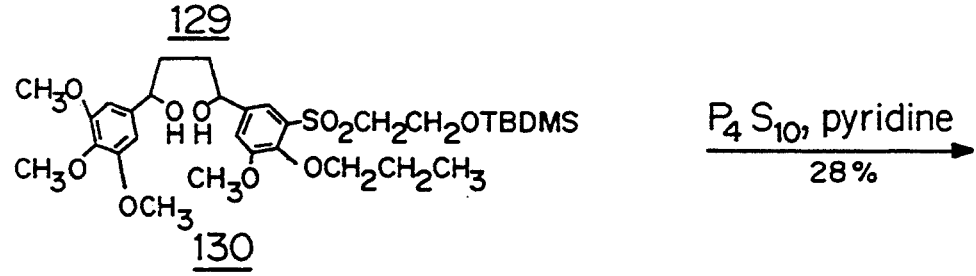
Figure 5:
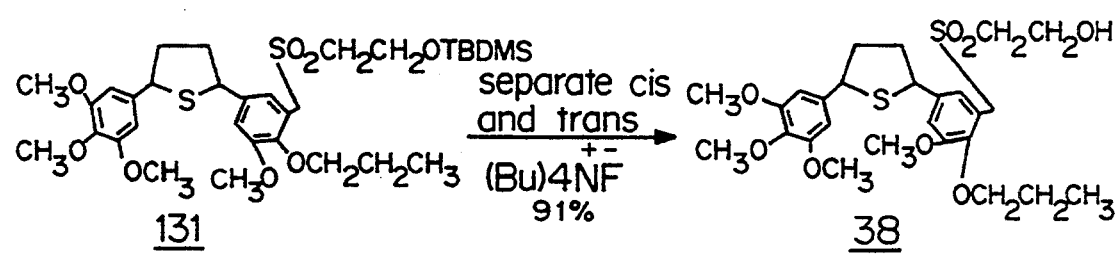

EXAMPLE 10 trans-2-(3,4-Dimethoxy-5-N,N-diallylaminophenyl)-5-(3,4,5-trimethoxyphenyl)-tetrahydrothiophene (Compound 10, FIG. 5)

Compound 10 was prepared by the method described above for compound 5, using compound 123 as the starting material.

EXAMPLE 11 trans-2-(3-Methoxy-4-propoxy-5-N,N-diallylaminophenyl)-5-(3,4,5-trimethoxyphenyl)-tetrahydrothiophene (Compound 11, FIG. 4)

Compound 11 was prepared in the same manner as compound 5, using compound 124 as the starting material.

EXAMPLE 12 cis- and trans-2-[N'-hydroxyl-N'-(substituted)]-N-[2-propoxy-3-methoxy-5-{5-(3,4,5-trimethoxyphenyl)-(tetrahydrofuran or tetrahydrothiophene)}-phenyl]-urea (compounds 12–32 and 38–41, FIG. 4).

3-Methoxy-4-propoxy-5-nitrobenzaldehyde (compound 114, FIG. 3).

A mixture of 5-nitrovanillin (19.72 g, 100 mmol), potassium carbonate (35 g, 253.23 mmol) and propyl iodide (32.86 mL, 335.83 mmol) in 160 mL of N,N-dimethylformamide was stirred at 60° C. for 12 hours. The mixture was then cooled, quenched with water and extracted with methylene chloride. The organic layer was washed several times with water, dried over magnesium sulfate, filtered and evaporated in vacuo to an oil which was purified by flash chromatography on silica gel (230–400 mesh) using 2:1 hexane/ethyl acetate as eluent, to provide 3-methoxy-4-propoxy-5-nitrobenzaldehyde (13.54 g, 57%). $^1$H NMR (CDCl$_3$): 1.00 (t, 3H), 18.5 (m, 2H), 4.00 (s, 3H), 4.25 (t, 2H), 7.65 (s, 1H), 7.85 (s, 1H), 9.95 (s, 1H).

Compounds 122 and 124 are prepared as described above.

cis and trans 2-[N'-Hydroxyl]-N-[2-propoxy-methoxy-5-{5-(3,4,5-trimethoxyphenyl)-tetrahydrofuran}-phenyl]urea (compound 12, FIG. 4)

trans-2-(3-Methoxy-4-propoxy-5-aminophenyl)-5-(3,4,5-trimethoxyphenyl)-tetrahydrofuran (41.7 mg, 0.1 mmol), triethylamine (20 mL), and triphosgene (10 mg, 0.034 mmol) in 5 mL of dry dichloromethane were refluxed for 2 hours under an argon atmosphere. The reaction was monitored with thin layer chromatography. On indication that the amine had been converted to isocyanate, the reaction was cooled to room temperature and hydroxylamine hydrochloride (10.5 mg, 0.15 mmol) in 0.5 mL of THF, 29 mL of triethylamine, and 0.1 mL of water added. The solution was stirred at room temperature overnight under an argon atmosphere. The solvent was then removed in vacuo, and the resulting oil dissolved in dichloromethane. The organic layer was washed with water, dried over magnesium sulfate, filtered and concentrated to an oil in vacuo. The oil was purified by flash chromatography on silica gel with 1:1.5 hexane/ethyl acetate as eluent (38 mg, 79.83%). $^1$H NMR (CDCl$_3$): 1.00 (t, 3H), 1.75 (m, 2H), 2.00 (m, 2H), 2.50 (m, 2H), 3.80–4.00 (m, 14H), 5.20 (m, 2H), 6.60 (s, 2H), 6.75 (s, 1H), 7.40 (s, 1H), 7.85 (br, 1H), 8.50 (s, 1H).

cis and trans 2-(3-Methoxy-4-propoxy-5-nitrophenyl)-5-(3,4,5-trimethoxyphenyl)tetrahydrothiophene (Compound 119, FIG. 3).

Compound 119 was prepared as described in Example 3.

The nitro group in compound 119 can be reduced to provide the corresponding amine (compound 122, FIG. 3) in a manner similar to that described above for the reduction of the nitro group in compound 121 to provide compound 124.

A wide variety of hydroxy urea derivatives of 2,5-diaryl tetrahydrofurans and tetrahydrothiophenes can be obtained using the general procedure set out above for the preparation of compound 12, by reaction of the appropriately substituted hydroxy amine with a 2,5-diaryl tetrahydrofuran or tetrahydrothiophene that has an appropriately placed amine function. The following compounds were obtained using this general method.

trans-2-[5-N'-Methyl-N'-hydroxyureidyl)-3-methoxy-4-propoxyphenyl]-5-(3,4,5-trimethoxyphenyl)-tetrahydrofuran (compound 13, FIG. 4).

$^1$H NMR (CDCl$_3$):1.00 (t, 3H), 1.75 (m, 2H), 2.00 (m, 2H), 2.50 (m, 2H), 3.2 (s, 3H), 3.80–4.00 (m,14H), 5.20 (m,2H), 6.60 (s,2H), 6.75 (s, 1H), 7.40 (s, 1H), 7.85 (s, H), 8.50 (s, 1H).

trans-2-[5-(N'-Isopropyl-N'-hydroxyureidyl)-3-methoxy-4-propoxyphenyl]-5-(3,4,5-trimethoxyphenyl)-tetrahydrofuran (compound 14, FIG. 4).

$^1$H NMR (CDCl$_3$): 1.00 (t, 3H), 1.2 (d, 6H), 1.75 (m, 2H), 2.00 (m, 2H), 2.50 (m, 2H), 3.80–4.00 (m, 14H), 4.6

(m, 1H), 5.20 (m, 2H), 6.60 (s, 2H), 6.75 (s, 1H), 6.77 (s, 1H), 7.90 (s, 1H), 8.50 (s, 1H).

trans-2-[5-(N'-t-Butyl-N'-hydroxyureidyl)-3-methoxy-4-propoxyphenyl]-5-(3,4,5-trimethoxyphenyl) tetrahydrofuran (compound 15, FIG. 4).

$^1$H NMR (CDCl$_3$):1.00 (t, 3H), 1.4 (s, 9H), 1.75 (m, 2H), 2.00 (m, 2H), 2.50 (m, 2H), 3.80–4.00 (m, 14H), 5.20 (m, 2H), 6.60 (s, 2H), 6.75 (s, 1H), 6.77 (s, 1H), 7.90 (s, 1H), 8.50 (s, 1H).

trans-2-[5-(N'-Cyclohexyl-N'-hydroxyureidyl)-3-methoxy-4-propoxyphenyl]-5-(3,4,5-trimethoxyphenyl)-tetrahydrofuran (compound 16, FIG. 4).

$^1$H NMR (CDCl$_3$):1.00 (t, 3H), 1.30 (m, 2H), 1.6 (m, 4H), 1.75 (m, 5H), 2.00 (m, 3H), 2.50 (m, 2H), 3.80–4.00 (m, 14H), 5.20 (m,2H), 6.60 (s, 2H), 6.75 (s, 1H), 6.77 (s, 1H), 7.85 (s, 1H), 8.50 (s, 1H).

trans-2-[5-(N'-Benzyl-N'-hydroxyureidyl)-3-methoxy-4-propoxyphenyl]-5-(3,4,5-trimethoxyphenyl)-tetrahydrofuran (compound 17, FIG. 4).

$^1$H NMR (CDCl$_3$):1.00 (t, 3H), 1.75 (m, 2H), 2.00 (m, 2H), 2.50 (m, 2H), 3.80–4.00 (m, 14H), 4.7 (s, 2H), 5.20 (m, 2H), 6.60 (s, 2H), 6.75 (s, 1H), 7.2–7.5 (m, 6H), 7.90 (s, 1H), 8.50 (s, 1H).

cis-2-[5-(N'-Hydroxyureidyl)-3-methoxy-4-propoxyphenyl]-5-(3,4,5-trimethoxyphenyl) tetrahydrofuran (compound 18, FIG. 4).

$^1$H NMR (CDCl$_3$):1.00 (t, 3H), 1.75 (m, 2H), 2.00 (m, 2H), 2.50 (m, 2H), 3.80–4.00 (m, 14H), 5.00 (m, 2H), 6.60 (s, 2H), 6.70 (s, 1H), 7.40 (s, 1H), 7.85 (s, H), 8.50 (s, 1H).

cis-2-[5-(N'-Hydroxy-N'-methylureidyl)-3-methoxy-4-propoxyphenyl]-5-(3,4,5-trimethoxyphenyl)-tetrahydrofuran (compound 19, FIG. 4).

$^1$H NMR (CDCl$_3$):1.00 (t, 3H), 1.75 (m, 2H), 2.00 (m, 2H), 2.50 (m, 2H), 3.2 (s, 3H), 3.80–4.00 (m, 14H), 5.00 (m, 2H), 6.60 (s, 2H), 6.70 (s, 1H), 7.70 (s, 1H), 7.85 (br, H), 8.50 (s, 1H).

cis-2-[5-(N'-Hydroxy-N'-i-propylureidyl)-3-methoxy-4-propoxyphenyl]-5-(3,4,5-trimethoxyphenyl)-tetrahydrofuran (compound 20, FIG. 4).

$^1$H NMR (CDCl$_3$):1.00 (t, 3H), 1.2 (d, 6H), 1.75 (m, 2H), 2.00 (m, 2H), 2.50 (m, 2H), 3.80–4.00 (m,14H), 4.6 (m, 1H), 5.00 (m, 2H), 6.60 (s, 2H), 6.75 (s, 1H), 6.77 (s, 1H), 7.90 (s, 1H), 8.50 (s, 1H).

cis-2-[5-(N'-tert-Butyl-N'-hydroxyureidyl)-3-methoxy-4-propoxyphenyl]-5-(3,4,5-trimethoxyphenyl)-tetrahydrofuran (compound 21, FIG. 4).

$^1$H NMR (CDCl$_3$):1.00 (t, 3H), 1.4 (s, 9H), 1.75 (m, 2H), 2.00 (m, 2H), 2.50 (m, 2H), 3.80–4.00 (m,14H), 5.00 (m,2H), 6.60 (s, 2H), 6.75 (s, 1H), 6.77 (s, 1H), 7.90 (s, 1H), 8.50 (s, 1H).

cis-2-[5-(N'-Cyclohexyl-N'-hydroxyureidyl)-3-methoxy-4-propoxyphenyl]-5-(3,4,5-trimethoxyphenyl)-tetrahydrofuran (compound 22, FIG. 4).

$^1$H NMR (CDCl$_3$):1.00 (t,3H), 1.30 (m, 2H), 1.6 (m,4H), 1.75 (m, 5H), 2.00 (m, 3H), 2.50 (m, 2H), 3.80–4.00 (m,14H), 5.00 (m,2H), 6.60 (s, 2H), 6.75 (s, 1H), 6.77 (s, 1H), 7.85 (s, 1H), 8.50 (s, 1H).

cis-2-[5-N'-Benzyl-N'-hydroxyureidyl)-3-methoxy-4-propoxyphenyl]-5-(3,4,5-trimethoxyphenyl)-tetrahydrofuran (compound 23, FIG. 4).

$^1$H NMR (CDCl$_3$):1.00 (t, 3H), 1.75 (m, 2H), 2.00 (m, 2H), 2.50 (m, 2H), 3.80–4.00 (m,14H), 4.7 (s, 2H), 5.0 (m,2H), 6.60 (s, 2H), 6.70 (s, 1H), 7.2–7.5 (m, 6H), 8.00 (s, 1H), 8.50 (s, 1H).

trans-2-[5-(N'-Hydroxyureidyl)-3-methoxy-4-propoxyphenyl]-5-(3,4,5-trimethoxyphenyl)tetrahydrothiophene (compound 24, FIG. 4).

$^1$H NMR (CDCl$_3$):1.00 (t, 3H), 1.80 (m,2H), 2.12 (m,2H), 2.60 (m, 2H), 3.80–4.00 (m,12H), 4.01 t, 2H), 4.75 (m,2H), 6.60 (s, 2H)), 6.70 (s, 1H), 7.40 (s, 1H), 7.85 (s, H), 8.50 (s, 1H).

trans-2-[5-(N'-Hydroxy-N'-methylureidyl)-3-methoxy-4-propoxyphenyl]-5-(3,4,5-trimethoxyphenyl)tetrahydrothiophene (compound 25, FIG. 4).

$^1$H NMR (CDCl$_3$):1.00 (t, 3H), 1.75 (m,2H), 2.00 (m,2H), 2.50 (m,2H), 3.20 (s, 3H), 3.80–4.00 (m,12H), 4.80 (m,2H), 6.60 (s, 2H), 6.70 (s, 1H), 7.70 (s, 1H), 7.85 (s, 1H), 8.50 (s, 1H).

trans-2-[5-(N'-Hydroxy-N'-i-propylylureidyl)-3-methoxy-4-propoxyphenyl]-5-(3,4,5-trimethoxyphenyl)tetrahydrothiophene (compound 26, FIG. 4).

$^1$H NMR (CDCl$_3$):1.00 (t, 3H), 1.2 (d, 6H), 1.75 (m, 2H), 2.00 (m, 2H), 2.50 (m, 2H), 3.80–4.00 (m,12H), 4.1 (t,2H), 4.60 (m, 1H), 4.8 (m, 2H), 6.60 (s, 2H), 6.75 (s, 1H), 6.77 (s, 1H), 7.90 (s, 1H), 8.50 (s, 1H).

trans-2-(N'-hydroxyl-N'-tert-butyl-N-(2-propoxy-3-methoxy-5-(3,4,5-trimethoxyphenyl)-tetrahydrothiophene) phenyl urea (compound 27, table 2).

$^1$H NMR (CDCl$_3$):1.00 (t,3H), 1.4 (s, 9H), 1.75 (m,2H), 2.00 (m,2H), 2.50 (m,2H), 3.80–4.00 (m,12H), 4.1 (t, 2H), 4.8 (m, 2H), 6.60 (s, 2H), 6.75 (s, 1H), 7.40 (s, 1H), 7.85 (s, H), 8.50 (s, 1H).

cis-2-[5-(N'-Hydroxyureidyl)-3-methoxy-4-propoxyphenyl]-5-(3,4,5-trimethoxyphenyl)tetrahydrothiophene (compound 28, FIG. 4).

$^1$H NMR (CDCl$_3$):1.00 (t, 3H), 1.75 (m, 2H), 2.00 (m, 2H), 3.20 (s, 3H), 3.80–4.00 (m, 12H), 4.1 (t, 2H), 4.65 (m, 2H), 6.60 (s, 2H), 6.70 (s, 1H), 7.70 (s, 1H), 7.85 (s, 1H), 8.50 (s, 1H).

cis-2-[5-(N'-Hydroxy-N'-methylureidyl)-3-methoxy-4-propoxyphenyl]-5-(3,4,5-trimethoxyphenyl) tetrahydrothiophene (compound 29, FIG. 4).

$^1$H NMR (CDCl$_3$):1.00 (t, 3H), 1.75 (m,2H), 2.00 (m,2H), 2.50 (m,2H), 3.20 (s, 3H), 3.80–4.00 (m, 12H), 4.1 (t, 2H), 4.65 (m,2H), 6.60 (s, 2H), 6.70 (s, 1H), 7.70 (s, 1H), 7.85 (s, 1H), 8.50 (s, 1H).

Cis-2-[5-(N'-Hydroxy-N'-isopropylureidyl)-3-methoxy-4-propoxyphenyl]-5-(3,4,5-trimethoxyphenyl)-tetrahydrothiophene (compound 30, table 2)

$^1$H NMR (CDCl$_3$):1.00 (t, 3H), 1.2 (d, 6H), 1.75 (m, 2H), 2.00 (m, 2H), 2.50 (m, 2H), 3.80–4.00 (m, 14H), 4.60 (m, 1H), 4.65 (m, 2H), 6.60 (s, 2H), 6.70 (s,1H), 7.40 (s, 1H), 7.85 (s, H), 8.50 (s, 1H).

Cis-2-[5-(N'-t-Butyl-N'-isopropylureidyl)-3-methoxy-4-propoxyphenyl]-5-(3,4,5-trimethoxyphenyl)-tetrahydrothiophene (compound 31, table 2).

¹H NMR (CDCl₃):1.00 (t, 3H), 1.4 (s, 9H), 1.75 (m, 2H), 2.00 (m, 2H), 2.50 (m, 2H), 3.80–4.00 (m, 12H), 4.1 (t, 2H), 4.65 (m, 2H), 6.60 (s, 2H), 6.75 (s, 1H), 7.40 (s, 1H), 7.85 (s, H), 8.50 (s, 1H).

Cis-2-[5-(N'-Cyclohexyl-N'-isopropylureidyl)-3-methoxy-4-propoxyphenyl]-5-(3,4,5-trimethoxyphenyl)-tetrahydrothiophene (compound 32, table 2).

¹H NMR (CDCl₃):1.00 (t, 3H), 1.30 (m, 2H), 1.6 (m, 4H), 1.75 (m, 5H), 2.00 (m, 2H), 2.50 (m, 2H), 3.80–4.00 (m, 14H), 4.6 (m, 2H), 6.60 (s, 2H), 6.75 (s, 1H), 6.77 (s, 1H), 7.90 (s, 1H), 8.50 (s, 1H).

trans-2-[5-(N'-Ethyl-N'-hydroxyureidyl)-3-methoxy-4-propoxyphenyl]-5-(3,4,5-trimethoxyphenyl)-tetrahydrofuran (compound 38, table 2).

¹H NMR (CDCl₃):1.00 (t, 3H), 1.2 (t, 3H), 1.75 (m, 2H), 2.00 (m, 2H), 2.50 (m, 2H), 3.75 (q, 2H), 3.80–4.00 (m, 14H), 5.20 (m, 2H), 6.60 (s, 2H), 6.75 (s, 1H), 6.77 (s, 1H), 7.90 (s, 1H), 8.50 (s, 1H).

trans-2-[5-(N'-n-Butyl-N'-hydroxyureidyl)-3-methoxy-4-propoxyphenyl]-5-(3,4,5-trimethoxyphenyl)-tetrahydrofuran (compound 39, table 2).

¹H NMR (CDCl₃):1.00 (t, 3H), 1.2 (t, 3H), 1.5 (m, 2H), 1.75 (m, 2H), 1.8 (m, 2H), 2.00 (m, 2H), 2.50 (m, 2H), 3.70 (t, 2H), 3.80–4.00 (m, 14H), 5.20 (m, 2H), 6.60 (s, 2H), 6.75 (s, 1H), 6.77 (s, 1H), 7.90 (s, 1H), 8.50 (s, 1H).

cis-2-[5-(N'-Ethyl-N'-hydroxyureidyl)-3-methoxy-4-propoxyphenyl]-5-(3,4,5-trimethoxyphenyl)-tetrahydrofuran (compound 40, table 2).

¹H NMR (CDCl₃):1.00 (t, 3H), 1.2 (t, 3H), 1.75 (m, 2H), 2.00 (m, 2H), 2.50 (m, 2H), 3.75 (q, 2H), 3.80–4.00 (m, 14H), 5.00 (m, 2H), 6.75 (s, 1H), 6.77 (s, 1H), 7.90 (s, 1H), 8.50 (s, 1H).

cis-2-[5-(N'-n-Butyl-N'-hydroxyureidyl)-3-methoxy-4-propoxyphenyl]-5-(3,4,5-trimethoxyphenyl)-tetrahydrofuran (compound 41, table 2).

¹H NMR (CDCl₃):1.00 (t, 3H), 1.2 (t, 3H), 1.5 (m, 2H), 1.75 (m, 2H), 1.8 (m, 2H), 2.00 (m, 2H), 2.50 (m, 2H), 3.70 (t, 2H), 3.80–4.00 (m, 14H), 5.00 (m, 2H), 6.60 (s, 2H), 6.75 (s, 1H), 6.77 (s, 1H), 7.90 (s, 1H), 8.50 (s, 1H).

Figure 8:
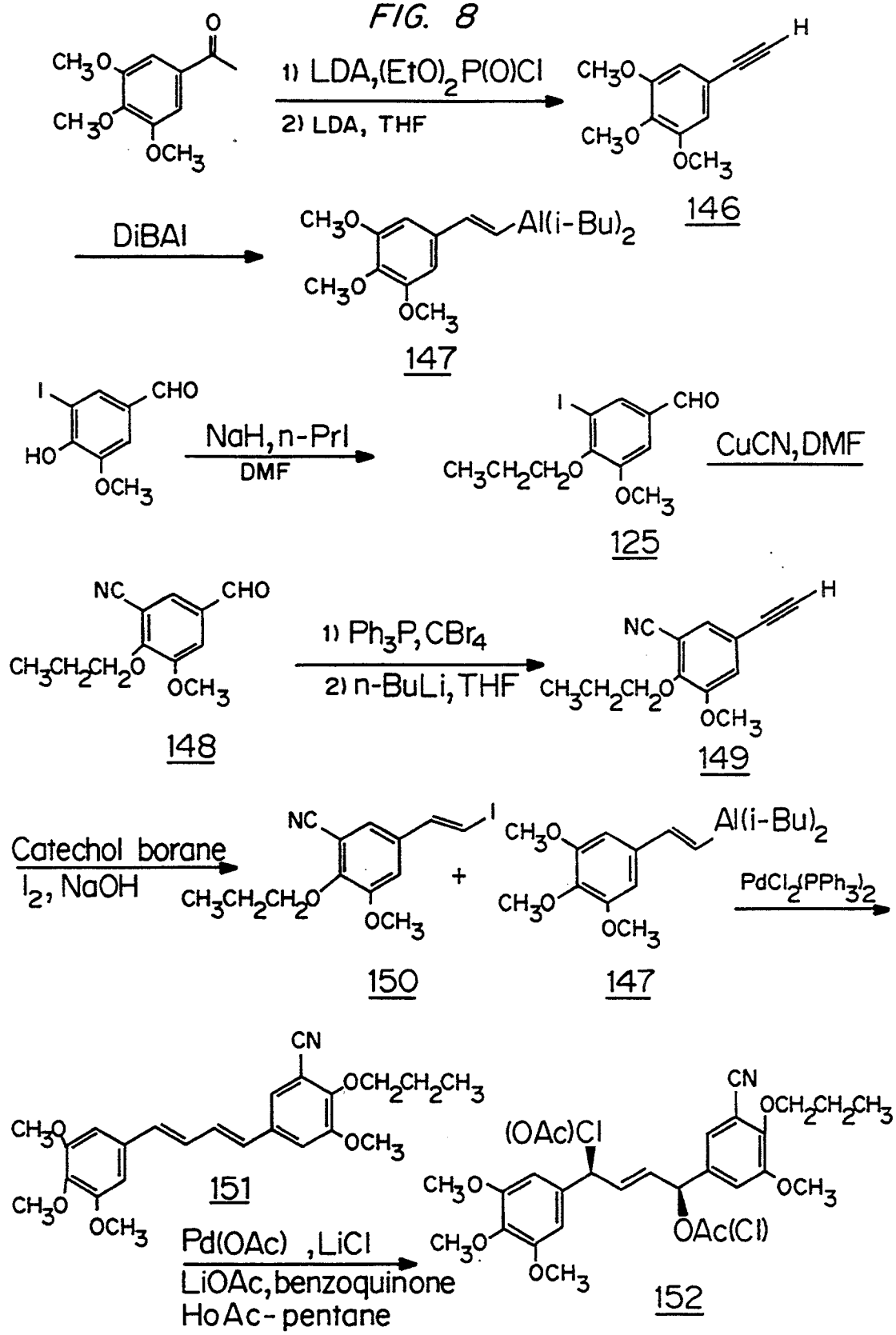
FIG. 8 is a schematic illustration of a process for the preparation of 2-(5-(N-hydroxy-N-methylaminocarbonyl)-amino(substituted)-3-methoxy-4-propoxy)-5-(3,4,5-trimethoxyphenyl)-cyclopentane (compound 158, FIG. 8).
Figure 8:
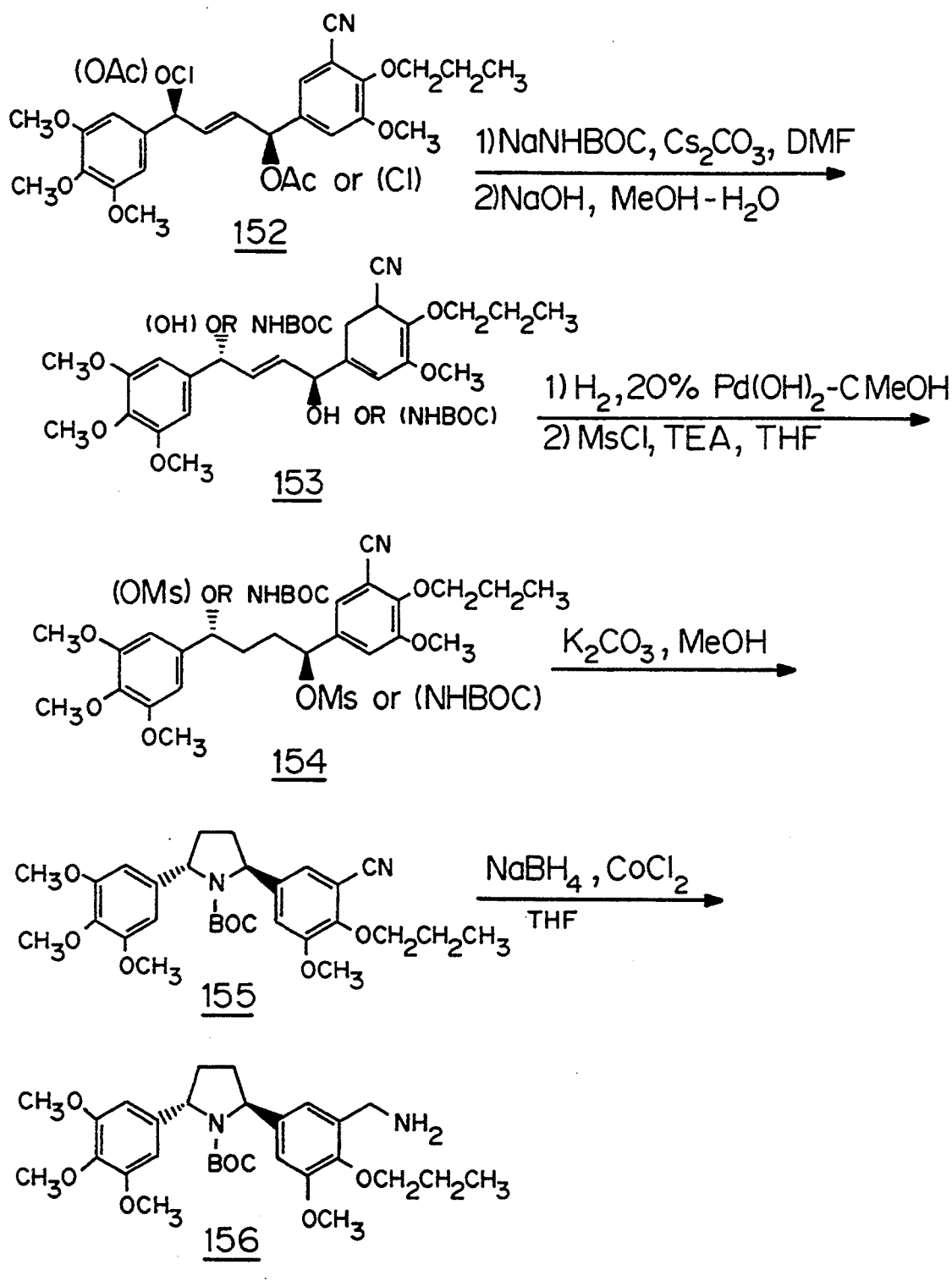
Figure 8:
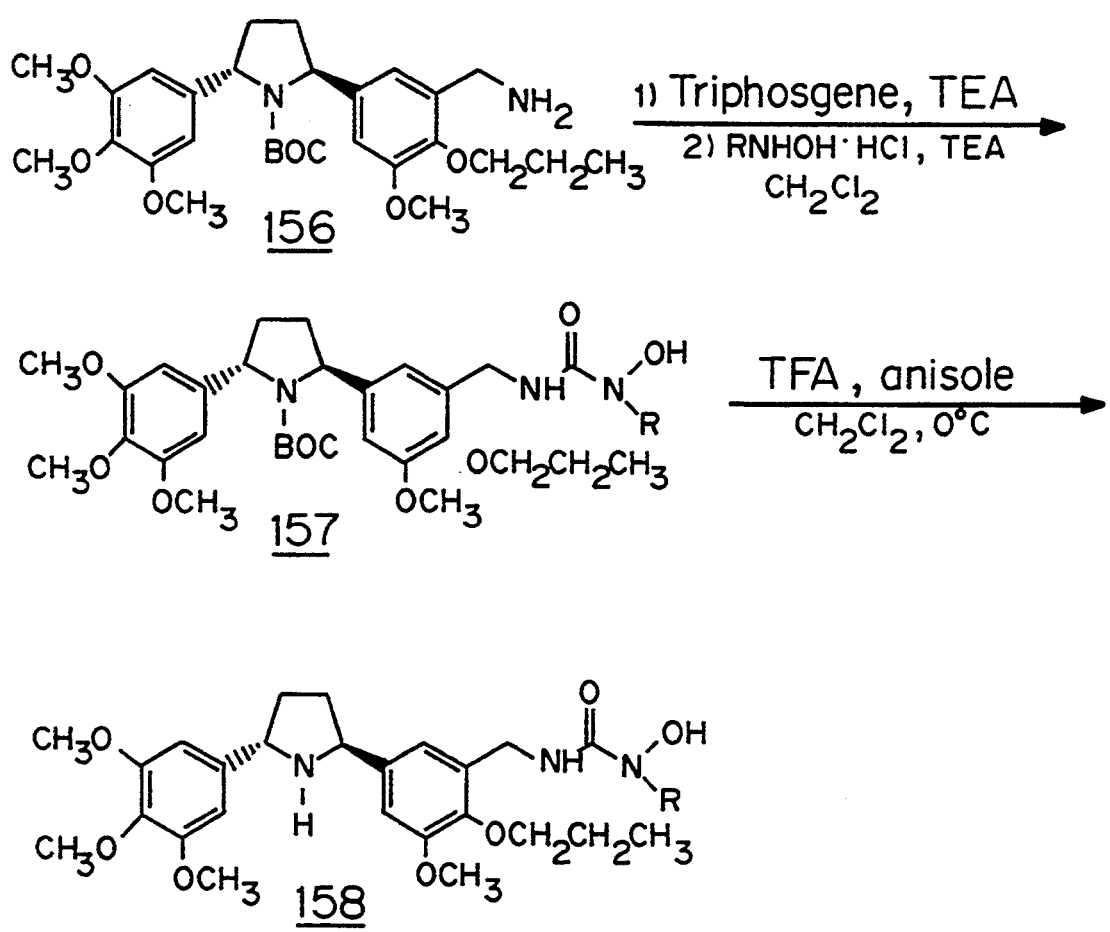

EXAMPLE 13 trans-2-(5-(N-Hydroxy-N-substituted-minocarbonyl)-aminomethyl-4-propoxy-3-methoxy)-5-(3,4,5-trimethoxyphenyl)-tetrahydrofuran (compounds 33–37, FIG. 8)

3-Methoxy-4-propoxy-5-iodobenzaldehyde (compound 125, FIG. 5)

5-Iodovanillin (25 g, 0.09 mol) in DMF (100 mL) was treated with potassium carbonate (32 g, 0.23 mol) and n-propyl iodide (52 g. 0.3 mol, 31 mL) and heated for 16 hours. The solution was allowed to cool to room temperature and then poured into water (500 mL) and extracted with ether (3×250 mL). The organic layers were combined and washed with water and saturated sodium chloride solution, and then dried over magnesium sulfate. The organic layer was evaporated by distillation under diminished pressure to an oil, and then purified by column chromatography (silica, 7:3 petroleum ether-ethyl acetate), to provide an amber colored solid (26.9 g, 93%). ¹H NMR (CDCl₃) 1.07 (t, 3H), 1.85 (m, 2H), 3.89 (s, 3H), 4.06 (t, 3H), 7.39 (s, 1 H), 7.84 (s, 1 H), 9.81 (s, 1 H).

1-(3-Methoxy-4-propoxy-5-iodophenyl)-4-(3,4,5-trimethoxyphenyl)-1,4-butanedione (compound 126, FIG. 5)

3,4,5-Trimethoxyphenylvinylketone (11.6 g, 0.052 mol), 3-methoxy-4-propoxy-5-iodobenzaldehyde (13.8 g, 0.043 mol), and 3-benzyl-5-(2-hydroxyethyl)-4-methylthiazolium chloride (4.6 g. 0.017 mol) were stirred in trimethylamine (35 mL) at 60° C. for 16 hours. The solution was then acidified, poured into chloroform (500 mL) and washed with 10% HCl, water and saturated aqueous sodium chloride. The organic layer was dried over magnesium sulfate, concentrated under reduced pressure, and the product isolated from petroleum ether-ethyl acetate to provide pale yellow microcrystals (27 g, 92%), m.p. 119°–121° C. ¹H NMR (CDCl₃) 1.07 (t, 3 H), 1.86 (m, 2 H), 3.40 (dd, 4H), 3.88 (s, 3H), 3.92 (s, 9H), 4.04 (t, 2 H), 7.29 (d, 1 H), 8.07 (d, 1 H).

Figure 6:
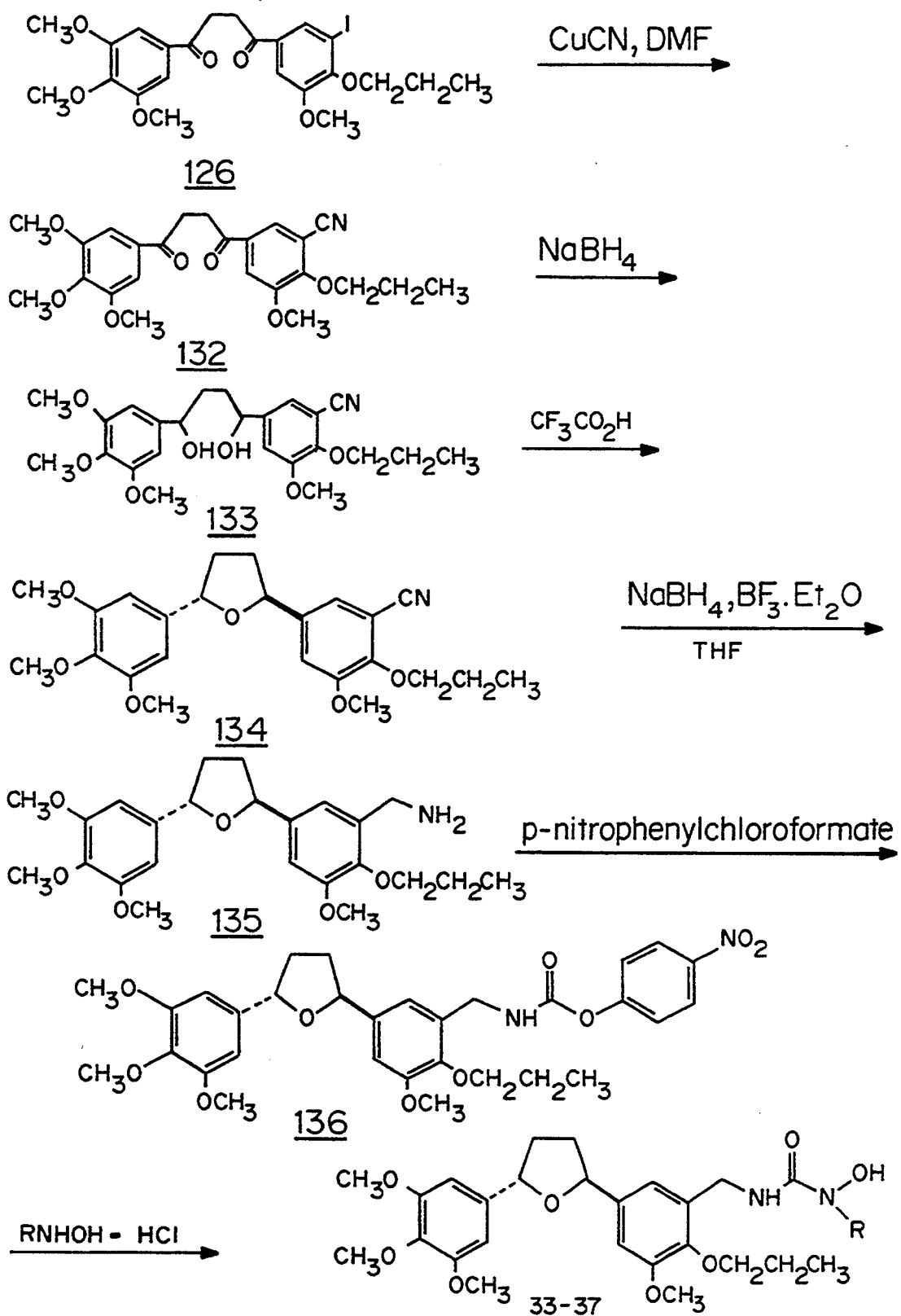
FIG. 6 is a schematic illustration of a process for the preparation of trans-2-(5-(N-hydroxy-N-(substituted)-aminocarbonyl)-aminomethyl-3-methoxy-4-propoxyphenyl)-5-(3,4,5-trimethoxyphenyl)-tetrahydrofuran (compounds 33-37, FIG. 6).

1-(3-Methoxy-4-propoxy-5-cyano)-4-(3,4,5-trimethoxyphenyl)-1,4-butanedione (compound 132, FIG. 6)

1-(3-Methoxy-4-propoxy-5-iodophenyl)-4-(3,4,5-trimethoxyphenyl)-1,4-butanedione (10.0 g, 18.4 mmol) and CuCN (16.6 g, 0.184 mol) in DMF (100 mL) were heated at 140° C. for 2 hours. The solution was cooled and poured onto water (500 mL). The aqueous phase was extracted with chloroform (3×250 mL). The organic layers were combined, washed with water and saturated aqueous sodium chloride, and then dried over magnesium sulfate. The resulting material was concentrated, and the product isolated from hexane-ethyl acetate as pale yellow microcrystals (7.75 g, 95%).

1-(3-Methoxy-4-propoxy-5-cyano)-4-(3,4,5-trimethoxyphenyl)-1,4-butanediol (compound 113, FIG. 6)

To 1-(3-methoxy-4-propoxy-5-cyano)-4-(3,4,5-trimethoxyphenyl)-1,4-butanedione (4.0 g, 9.06 mmol) in 5:1 methanol/THF (125 mL) was added sodium borohydride (617 mg, 16.3 mmol), and the solution stirred overnight. Solvent was removed under reduced pressure and the crude residue was dissolved in dichloromethane (250 mL). The solution was washed with water and brine, dried over magnesium sulfate, and then concentrated under reduced pressure. It was used without further purification.

trans-2-(3-Methoxy-4-propoxy-5-Cyano)-5-(3,4,5-trimethoxyphenyl)-tetrahydrahydrofuran (compound 134, FIG. 6)

To 1-(3-methoxy-4-propoxy-5-cyano)-4-(3,4,5-trimethoxyphenyl)-1,4-butanediol (9.0 mmol) in chloroform (100 mL) at 0° C. was added dropwise trifluoroacetic acid (36 mmol, 2.8 mL) in chloroform (50 mL) over 30 minutes. The solution was then stirred at 0° C. overnight. The solution was washed with 10% potassium carbonate, water, and saturated aqueous sodium chloride, and then dried over magnesium sulfate. The solution was then concentrated under reduced pressure and the trans isomer isolated as colorless needles from petroleum ether-ethyl acetate (3.06 g, 79%).

trans-2-(3-Methoxy-4-propoxy-5-aminomethyl)-5-(3,4,5-trimethoxyphenyl)-tetrahydrofuran (compound 135, FIG. 6)

To trans-2-(3-methoxy-4-propoxy-5-cyano)-5-(3,4,5-trimethoxyphenyl)-tetrahydrofuran (500 mg, 1.17 mmol) in THF (25 mL) was added sodium borohydride (80 mg, 2.1 mmol) and boron trifluoride etherate (400 mg, 2.8 mmol) dropwise over thirty minutes. The solution was then refluxed for four hours, cooled, treated with a few drops of 10% HCl, poured into water and extracted with dichloromethane. The organic layers were combined, washed with water and saturated aqueous sodium chloride, and then dried over magnesium sulfate. The dried solution was concentrated, and then purified by column chromatography (silica, 9:1 dichloromethane-methanol). The product was isolated as an amber oil (207 mg, 41%).

trans-2-[3-Methoxy-4-propoxy-5-(4nitrophenoxy carbonyl)-aminomethyl]-5-(3,4,5-trimethoxyphenyl)-tetrahydrofuran (compound 136, FIG. 6)

Trans-2-(3-methoxy-4-propoxy-5-aminomethyl)-5-(3,4,5-trimethoxyphenyl)-tetrahydrofuran (207 mg. 0.048 mmol), nitrophenylchloroformate (106 mg, 0.53 mmol), and diisopropylethylamine (69 mg, 0.53 mmol) were stirred in dichloromethane (3 mL) for 12 hours. The solution was then concentrated and purified by column chromatography (silica, 85:15 dichloromethane-ether). The product was isolated as a yellow oil (251 mg, 88%).

trans-2-[3-Methoxy-4-propoxy-5-(N-hydroxyaminocarbonyl)-aminomethyl]-5-(3,4,5-trimethoxyphenyl)-tetrahydrofuran (compound 33, FIG. 6)

Trans-2-[3-methoxy-4-propoxy-5-(4-nitrophenoxy carbonyl) aminomethyl]-5-(3,4,5-trimethoxyphenyl)-tetrahydrofuran (57 mg, 0.096 mmol), hydroxylamine hydrochloride (10 mg, 0.15 mmol), and diisopropylethylamine (40 mg, 0.3 mmol) were stirred in dichloromethane (3 mL) for 24 hours. The solution was then diluted with dichloromethane and washed with 10% sodium bicarbonate, water, and saturated aqueous sodium chloride, and then dried over magnesium sulfate. The solution was then concentrated, and purified by preparative TLC (silica, 95:5 dichloromethane-methanol). The pure material was isolated as a colorless oil (16 mg, 34%), $^1$H NMR (CDCl$_3$) 1.0 (t, 3 H), 1.75 (m, 2 H), 2.0 (m, 2H), 2.44 (m, 2 H), 3.86 (m, 12 H), 3.91 (t, 2 H), 4.42 (d, 2 H), 5.13 (t, 2 H), 6.3–7.1 (m, 4H).

trans-2-3-Methoxy-4-propoxy-5-(N-hydroxy N-methoxylaminocarbonyl)-5-(3,4,5-trimethoxyphenyl)-tetrahydro-furan (compound 34, FIG. 6)

trans-2-3-methoxy-4-propoxy-5-(N-hydroxyaminocarbonyl) aminomethyl-5-(3,4,5-trimethoxyphenyl)-tetrahydrofuran (42 mg, 0.070 mmol), N-methyl hydroxylamine hydrochloride (9 mg, 0.11 mmol), and diisopropylethylamine (0.33 mmol) in dichloromethane (3 mL) were stirred for 24 hours. The solution was diluted with dichloromethane and washed with 10% sodium bicarbonate, water and saturated sodium chloride, and then dried over magnesium sulfate. The solution was then concentrated, and purified by preparative TLC (silica, 95:5 dichloromethane-methanol). The product was isolated as a colorless oil weighing (14 mg, 40%). $^1$H NMR (CDCl$_3$) 1.0 (t, 3 H), 1.75 (m, 2 H), 2.0 (m, 2H), 2.44 (m, 2 H), 3.04 (s, 3 H), 3.86 (m, 12 H), 3.91 (t, 2 H), 4.42 (d, 2 H), 5.13 (m, 2 H), 6.3–7.1 (m, 4H).

trans-2-3-Methoxy-4-propoxy-5-(N-Hydroxy-N-isopropylaminocarbonyl)-5-(3,4,5-trimethoxyphenyl)-tetrahydrofuran (compound 35, FIG. 6)

trans-2-3-methoxy-4-propoxy-5-(N-hydroxyaminocarbonyl) aminomethyl-5-(3,4,5-trimethoxyphenyl)-tetrahydrofurn (40 mg, 0.067 mmol), N-isopropyl hydroxylamine hydrochloride (11 mg, 0.1 mmol), and diisopropylethylamine (0.2 mmol) were stirred in dichloromethane (3 mL) for 24 hours. The solution was diluted with dichloromethane, washed with 10% sodium bicarbonate, water and saturated aqueous sodium chloride, and then dried over magnesium sulfate. The solution was concentrated, and then purified by preparative TLC (silica, 95:5 dichloromethane-methanol). The product was isolated as a colorless solid (16 mg, 45%). $^1$H NMR (CDCl$_3$) 1.0 (t, 3 H), 1.1 (d, 6 H), 1.75 (m, 2 H), 2.0 (m, 2H), 2.44 (m, 2 H), 3.04 (s, 3 H), 3.86 (m, 12 H), 3.91 (t, 2 H), 4.40 (m, 1 H), 4.42 (d, 2 H), 5.13 (m, 2 H), 6.3–7.1 (m, 4H).

trans-2-3-Methoxy-4-propoxy-5-(N-hydroxy-N-cyclohexylaminocarbonyl) aminomethyl-5-(3,4,5-trimethoxyphenyl)-tetrahydrofuran (Compound 36, FIG. 6)

trans-2-3-methoxy-4-propoxy-5-(N-hydroxy-N-isopropylaminocarbonyl)-5-(3,4,5-trimethoxyphenyl)-tetrahydrofuran (59 mg, 0.1 mmol), N-cyclohexyl hydroxylamine hydrochloride (23 mg, 0.15 mmol), and diisopropylethylamine (0.2 mmol) were stirred in dichloromethane (3 mL) for 24 hours. The solution was diluted with dichloromethane, washed with 10% sodium bicarbonate, water and saturated sodium chloride, and then dried over magnesium sulfate. The solution was then concentrated and purified by preparative TLC (silica, 95:5 dichloromethane-methanol), to provide the product a colorless solid (24 mg., 42%) $^1$H NMR (CDCl$_3$) 1.0 (t, 3 H), 1.1–1.8 (m, 10 H), 1.75 (m, 2 H), 2.0 (m, 2 H), 2.44 (m, 2H), 3.04 (s, 3 H), 3.86 (m, 13 H), 3.91 (t, 2 H), 4.42 (d, 2 H), 5.13 (m, 2 H), 6.3–7.1 (m, 4H).

trans-2-3-Methoxy-4-propoxy-5-(N-hydroxy-N-benzylaminocarbonyl)-5-(3,4,5-trimethoxyphenyl)-tetrahydro-furan (compound 37, FIG. 6)

trans-2-3-methoxy-4-propoxy-5-(N-hydroxy-N-cyclohexylaminocarbonyl) aminomethyl-5-(3,4,5-trimethoxyphenyl)-tetrahydrofuran (53 mg, 0.089 mmol), N-benyl hydroxylamine hydrochloride (21 mg, 0.133 mmol), diisopropylethylamine (0.27 mmol), and stirred in dichloromethane (3 mL) for 24 hours. The reaction was diluted with dichloromethane and the organic layer was washed with 10% sodium bicarbonate, water, and saturated aqueous sodium chloride, and then dried over magnesium sulfate. The solution was then concentrated and purified by preparative TLC (silica, 95:5 dichloromethane-methanol), and the product isolated as a colorless oil (22 mg., 42%). $^1$H NMR (CDCl$_3$) 1.0 (t, 3 H), 1.75 (m, 2 H), 2.0 (m, 2H), 2.44 (m, 2 H), 3.86 (m, 12 H), 3.91 (t, 2 H), 4.42 (d, 2 H), 4.65 (s, 2 H), 5.13 (t, 2 H), 6.3–7.1 (m, 4H), 7.3–7.5 (m, 5 H).

EXAMPLE 14

Cis and trans-5-(3,4,5-Trimethoxyphenyl)-2-(3-methoxy-4-propoxy-5-hydroxyethylsulfonyl)-tetrahydrothiophene (Compound 42, FIG. 5)

Compounds 125 and 126 were prepared as described above.

1-(3-Methoxy-4-propoxy-5-hydroxyethylthiophenyl)-4-(3,4,5-trimethoxyphenyl)-butane-1,4-dione (Compound 127, FIG. 5).

To a solution of 1-(3-methoxy-4-propoxy-5-iodophenyl)-4-(3,4,5-trimethoxyphenyl)-butane-1,4-dione (13.55 g, 25 mmol) in 100 mL of DMF was added 13.5 g (212.43 mmol) of copper powder. The slurry was heated at 130° C. for 2 hours and a solution of 2-hydroxyethyldisulfide (4.88 mL, 40 mmol) in 25 mL of DMF added. Heating was continued for an additional 20 hours. The mixture was then cooled, filtered and washed with ethyl acetate. Water (125 mL) was added and the mixture extracted with ethyl acetate. The organic layer was washed several times with water, dried over magnesium sulfate and evaporated. The crude product was purified by flash chromatography on silica gel using 1:1 hexane/ethyl acetate as eluent (7.5 g, 61%). $^1$H NMR (CDCl$_3$): 1.07 (t, 3H), 1.85 (m, 2H), 2.38 (t, 1H), 3.13 (t, 2H), 3.41 (s, 4H), 3.72 (q, 2H), 3.90 (s, 3H), 3.93 (s, 9H), 4.07 (t, 2H), 7.29 (s, 2H), 7.49 (d, 1H), 7.73 (d, 1H).

1-(3-Methoxy-4-propoxy-5-hydroxyethylsulfonylphenyl)-4-(3,4,5-trimethoxyphenyl)-butane-1,4-dione (compound 128, FIG. 5).

A suspension of magnesium monoperoxyphthalic acid (18.51 g, 37.42 mmol) in 60 mL of water was added to 1(3-methoxy-4-propoxy-5-hydroxyethylthiophenyl)-4-(3,4,5-trimethoxyphenyl)-butane-1,4-dione (9.84 g, 20 mmol) in 180 mL of acetonitrile. The solution was stirred for 2 hours, and then 600 mL of water added, and the mixture extracted with methylene chloride. The organic layer was washed with 5% sodium hydroxide solution, water, and saturated aqueous sodium chloride and then dried with magnesium sulfate and evaporated to a white solid. The solid was purified by flash column chromatography using 2:1 ethyl acetate/hexane (7.98 g, 76%). $^1$H NMR (CDCl$_3$): 1.04 (t, 3H), 1.88 (m, 2H), 2.77 (bs, 1H), 3.43 (s, 4H), 3.66 (t, 2H), 3.91 (s, 9H), 3.94 (s, 3H), 3.99 (m, 2H), 4.21 (t, 2H), 7.27 (s, 2H), 7.83 (d, 1H), 8.21 (d, 1H).

1-(3-Methoxy-4-propoxy-5-dimethyl-tert-butylsiloxyethylsulfonylphenyl)-4-(3,4,5-trimethoxyphenyl)-butane-1,4-dione (compound 129, FIG. 5).

A suspension of 5.24 g (10 mmol) of 1-(3-methoxy-4-propoxy-5-hydroxyethylsulfonylphenyl)-4-(3,4,5-trimethoxyphenyl)-butane-1,4-dione, tert-butyldimethylsilyl chloride (1.81 g, 12 mmol), and imidazole (0.82 g, 12.05 mmol) in 55 mL of methylene chloride was stirred at room temperature for 12 hours. The solution was filtered, evaporated to an oil, and then purified by flash chromatography on silica gel using 1:1 hexane/ethyl acetate (5.42 g, 85%), $^1$H NMR (CDCl$_3$): −0.07 (s, 6H), 0.75 (s, 9H), 1.06 (t, 3H), 1.90 (m, 2H), 3.43 (s, 4H), 3.68 (t, 2H), 4.00 (t, 2H), 4.22 (t, 2H), 7.29 (s, 2H), 7.80 (d, 1H), 8.20 (d, 1H).

1-(3-Methoxy-4-propoxy-5-dimethyl-tert-butylsiloxyethylsulfonylphenyl)-4-(3,4,5-trimethoxyphenyl)-butane-1,4-diol (Compound 130, FIG. 5).

To a solution of 1-(3-methoxy-4-propoxy-5-dimethyl-tert-butylsiloxyethylsulfonylphenyl)-4-(3,4,5-trimethoxyphenyl)-butane-1,4-dione (6.38 g, 10 mmol) in 90 mL of methanol and 25 mL tetrahydrofuran was added dropwise sodium borohydride (903 mg, 23.88 mmol) in 40 mL of water. After the addition was completed, the reaction mixture was stirred at room temperature for 3 hours, quenched with water and extracted with dichloromethane. The organic layer was dried over magnesium sulfate, filtered and evaporated to a form (4.57 g, 71%). $^1$H NMR (CDCl$_3$): −0.05 (s, 6H), 0.77 (s, 9H), 1.04 (t, 3H), 1.86 (m, 6H), 3.65 (m, 2H), 3.74 (m, 2H), 3.84 (s, 3H), 3.87 (s, 6H), 3.89 (s, 3H), 3.97 (t, 2H), 4.11 (t, 2H), 4.72 (m, 2H), 6.57 (s, 1H), 7.22 (s, 1H), 7.43 (s, 1H).

trans-2-(3-Methoxy-4-propoxy-5-dimethyl-tert-butylsiloxyethylsulfonyl)-5-(3,4,5-trimethoxyphenyl)-tetrahydrothiophene (compound 131, FIG. 5).

A suspension of P$_4$S$_{10}$ (2.90 g, 6.53 mmol) in 48 mL of pyridine was heated at 120° C. for 75 minutes. To the suspension was added a solution of 1-(3-methoxy-4-propoxy-5-dimethyl-tert-butylsiloxyethylsulfonylphenyl)-4-(3,4,5-trimethoxyphenyl)-butane-1,4-diol (3.21 g, 5 mmol) in 20 mL of pyridine. The temperature was reduced to 90° C. and stirring continued for an additional 90 minutes. Ice and water were then added, and the mixture extracted with methylene chloride. The organic layer was washed with water, 5% HCl, sodium bicarbonate and saturated sodium chloride solution, and then dried with magnesium sulfate, filtered and evaporated. The resulting cis and trans thiophenes were separated by HPLC using Water's prep Nova-Pak HR silica cartridge (9:1 hexane; ethyl acetate) to provide 580 mg (20%) of the trans isomer and 145 mg (5%) of the cis isomer. Trans isomer. NMR (CDCl$_3$): −0.05 (s, 6H), 0.80 (s, 9H), 1.10 (t, 3H), 1.95 (m, 2H), 2.05 (m, 2H), 2.6 (m, 2H), 3.7 (t, 3H), 3.95 (m, 12H), 4.00 (t, 3H), 4.2 (t, 3H), 4.9 (m, 2H), 6.8 (s, 2H), 7.40 (d, 1H), 7.60 (d, 1H).

cis and trans-5-(3,4,5-Trimethoxyphenyl)-2-(3-methoxy-4-propoxy-5-hydroxyethylsulfonyl)-tetrahydrothiophene (compound 38, FIG. 5)

To an ice-water cooled solution of trans-2-(3,4,5-trimethoxyphenyl)-5-(3-methoxy-4-propoxy-5-dimethyl-tert-butylsiloxyethylsulfonyl)-tetrahydrothiophene (80 mg, 0.125 mmol) in 4 mL of dry tetrahydrofuran was added dropwise a solution of tetrabutylammonium fluoride in 2 mL of tetrahydrofuran. The solution was stirred at room temperature for two hours, and then the solvent evaporated under vacuum and passed through a small column of silica gel using 1:1 hexane:ethyl acetate to give a white solid (60 mg, 91%), $^1$H NMR (CDCl$_3$): 1.10 (t, 3H), 1.95 (m, 2H), 2.05 (m, 2H), 2.6 (m, 2H), 3.7 (t, 3H), 3.95 (m, 12H), 4.00 (t, 3H), 4.9 (m, 2H), 6.8 (s, 2H), 7.40 (d, 1H), 7.60 (d, 1H).

EXAMPLE 15

Figure 7:
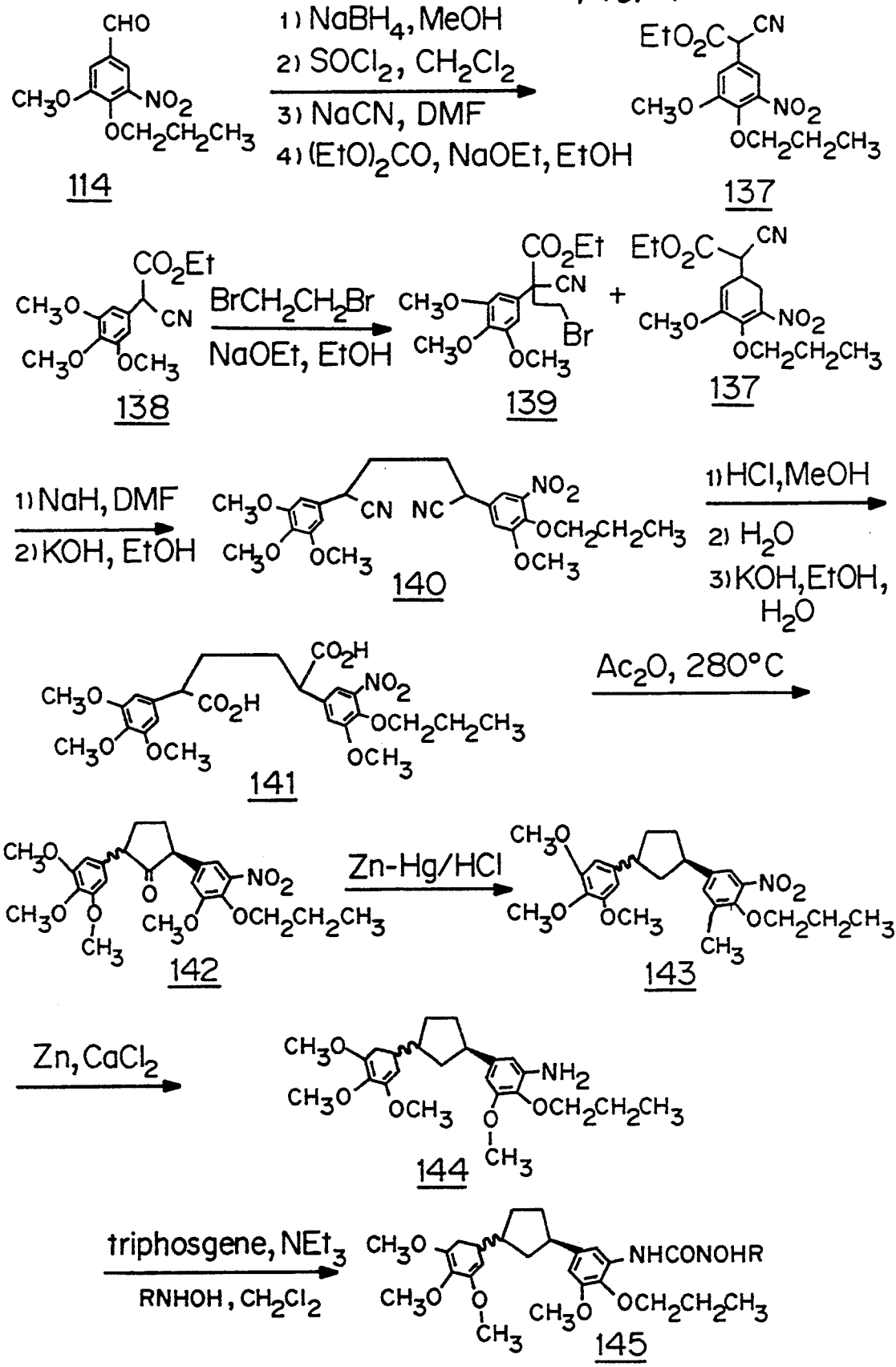
FIG. 7 is a schematic illustration of a process for the preparation of 1-(3-nitro-4-propoxy-5-methoxyphenyl)-3-(3,4,5-trimethoxyphenyl)cyclopentane (compound 143, FIG. 7), 1-(3-amino-4-propoxy-5-methoxyphenyl)-3-(3,4,5-trimethoxyphenyl)cyclopentane (compound 144, FIG. 7), and 2-(N'-hydroxyl-N'-(substituted)-N-(2-propoxy-3-methoxy-5-(5-(3,4,5-trimethoxyphenyl)cyclopentane)phenyl urea (compound 145, FIG. 7).

1-(3-Nitro-4-propoxy-5-methoxyphenyl)-3-(3,4,5-trimethoxyphenyl)cyclopentane (compound 143, FIG. 7).

This compound is synthesized as set out in detail in FIG. 7, following the procedure as outlined by Graham, D. W. et al. ("1,3-Diaryl Cyclopentanes: A New Class of Potent PAF Receptor Antagonists", 197th ACS National Meeting, Dallas, Tex., Apr. 9-14, 1989, Division of Medicinal Chemistry, poster No. 25) starting from compound 114 (FIG. 7). Reduction and functionalization of this compound is carried out similar to that described for compounds 119-121 (FIG. 3).

EXAMPLE 16

2-(5-(N-hydroxy-N-methylaminocarbonyl)-amino(substituted)-3-methoxy-4-propoxy)-5-(3,4,5-trimethoxyphenyl)-cyclopentane (compound 158, FIG. 8)

3,4,5-Trimethoxyacetophenone is converted to the corresponding acetylene (compound 146, FIG. 8) using the procedure outlined by Negishi et al., J. Org. Chem., 45, 2526 (1980), using diethylchlorophosphate and lithium diisopropylamide. 5-Iodovanillin is alkylated with n-propyl iodide as described in Example 6. The resulting alkylated aldehyde (compound 125, FIG. 8) is converted to the corresponding nitrile (compound 148, FIG. 8) as described in Example 13, Compound 148 is converted to the terminal alkyne (compound 149, FIG. 8) via the Corey-Fuchs procedure (Corey, E. J. et al., Tetra, Lett, 3769 (1972)). The E-vinyl iodide (compound 150, FIG. 8) is synthesized from compound 149 using catechol borane and iodine. Heat acetylene and catechol borate at 60° C. for 3 hours. Stir resulting boronate ester with water for 2 hours. Filter boronic acid to remove catechol. Dissolve the boronic acid in THF and sodium hydroxide (3 equivalent). Treat with iodine (1 equivalent) and stir for 30 minutes. The product was isolated by standard extractive workup and column chromatography. The iodide (compound 150) and the vinyl alane (compound 147) are coupled using a palladium catalyst to yield compound 151. Compound 151 is converted to the allylic chloroacetate (compound 152) via palladium catalysis. Compound 152 is converted to the BOC protected amine, and the acetate removed via saponification to yield compound 153. Compound 153 is saturated by hydrogenation and the alcohol moieties converted to mesylates (compound 154). Cyclization of compound 154 to the pyrrole (compound 155) is accomplished with mild base. Compound 155 is then reduced and the resultant amine (156) converted to the hydroxyurea (157) (vide infra). Finally, the pyrrole is deprotected using trifluoroacetic acid and anisole in dichloromethane at zero degrees to yield the compound 158.

EXAMPLE 17

Figure 9:
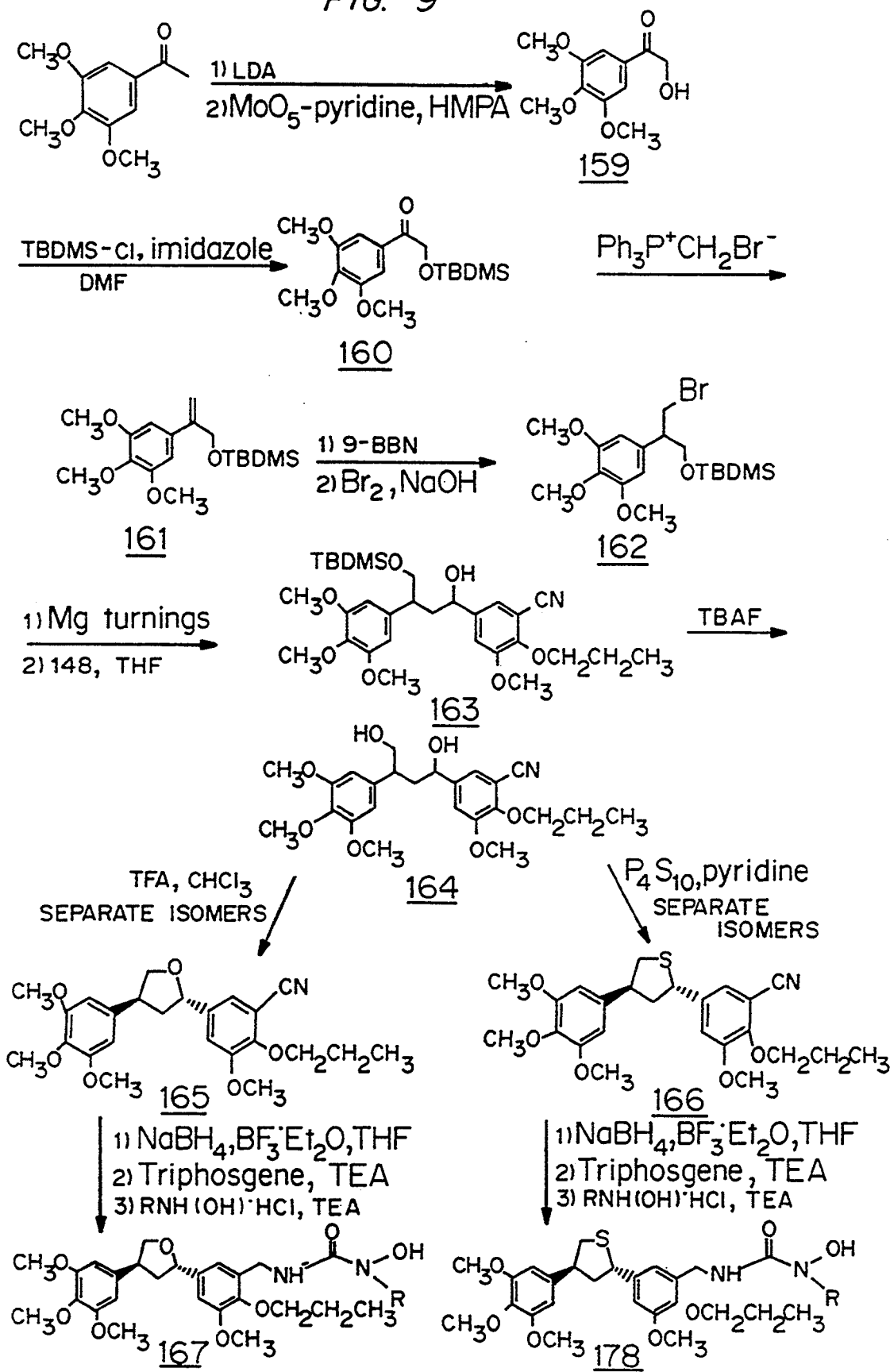
FIG. 9 is a schematic illustration of a process for the preparation of 2-(5-(N-hydroxy-N-methylaminocarbonyl)-amino(substituted)-3-methoxy-4-propoxy)-4-(3,4,5-trimethoxyphenyl)-tetrahydrofuran (compound 167, FIG. 9), and 2-(5-(N-hydroxy-N-methylaminocarbonyl)-amino(substituted)-3-methoxy-4-propoxy)-4-(3,4,5-trimethoxyphenyl)-tetrahydrothiophene (compound 168, FIG. 9).
Figure 9:
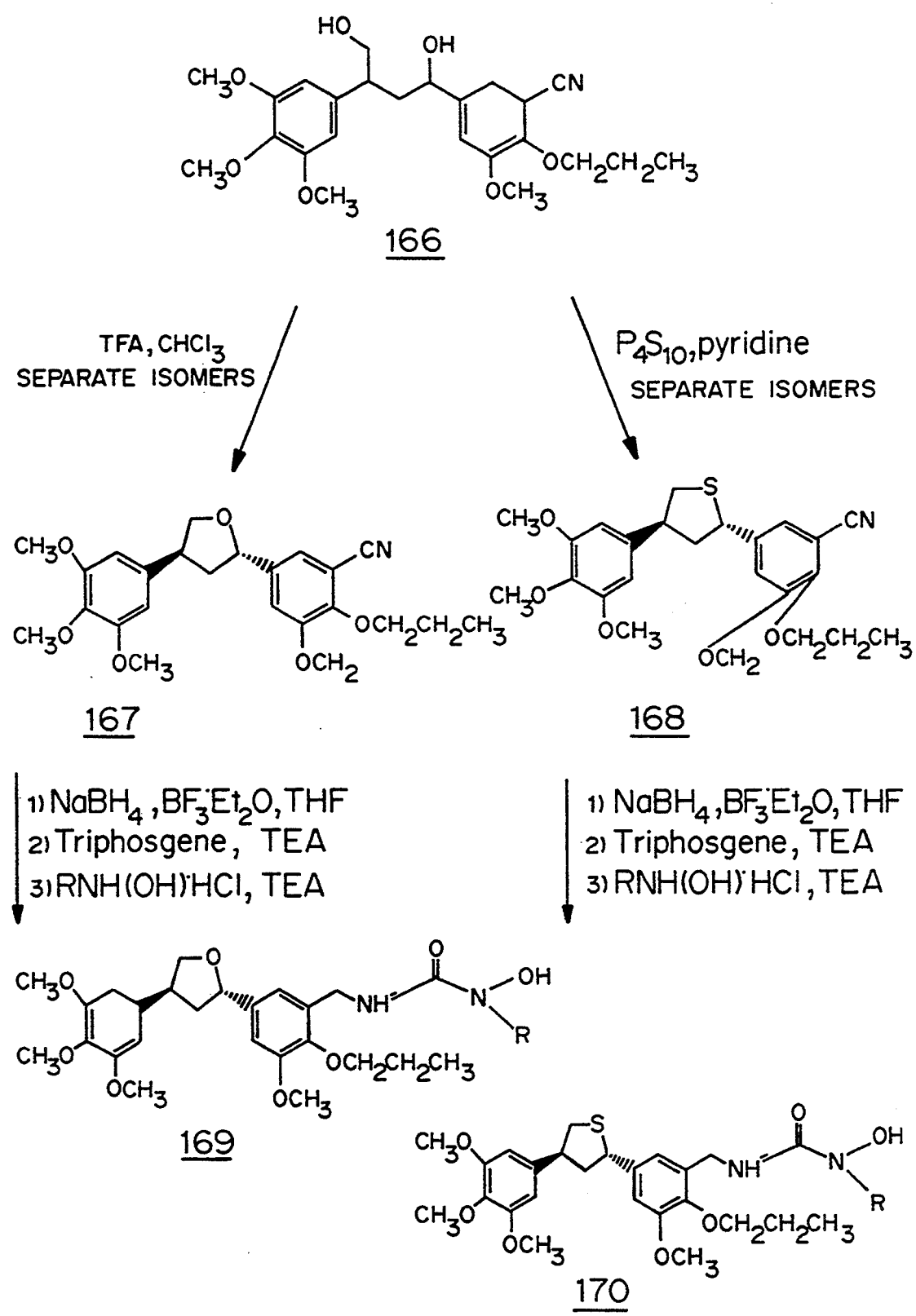

Synthesis of 2,4-Diaryl Tetrahydrofuran and Tetrahydrothiophene (Compounds 167 and 168, FIG. 9).

3,4,5-Trimethoxyacetophenone is oxidized to the corresponding hydroxyketone (compound 159, FIG. 9) and then protected as the silyl ether (compound 160, FIG. 9). Compound 160 is converted to the corresponding olefin (compound 161, FIG. 9) using a Wittig reaction. Compound 161 is converted to the primary bromide compound 162 with 9-BBN (9-borabicyclo[3.3.1-]nonane). Compound 162 is then converted to the Grignard reagent and treated with the compound 148 to yield compound 163. The alcohol protecting group in compound 163 is removed with TBAF (tetrabutylammonium fluoride) and the resulting diol (compound 164) converted to the tetrahydrofuran (165) or tetrahydrothiophene (166) using procedures described above.

Compounds 167 and 168 are converted to the hydroxyureas (167) and (169) by procedures described above.

II. Pharmaceutical Compositions

Humans, equinone, canine, bovine and other animals, and in particular, mammals, suffering from disorders mediated by PAG or products of 5-lipoxygenase can be treated by administering to the patient an effective amount of one or more of the above-identified compounds or a pharmaceutically acceptable derivative or salt thereof in a pharmaceutically acceptable carrier or diluent. The active materials can be administered by any appropriate route, for example, orally, parenterally, intravenously, intradermally, subcutaneously, or topically, in liquid, cream, gel or solid form.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or (c) combination of (a) and (b); e.g., a zinc tannate salt or the like.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by the other means known to those skilled in the art.

The compound in conveniently administered in any suitable unit dosage form, including but not limited to one containing 1 to 3000 mg, preferably 5 to 500 mg of active ingredient per unit dosage form. A oral dosage of 25-250 mg is usually convenient.

The active ingredient should be administered to achieve peak plasma concentrations of the active compound of about 0.01-30 mM, preferably about 0.1-10 mM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regiments should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

the active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, antifungals, antiinflammatories, or antiviral compounds.

Solutions or suspension used for parenteral, intradermal, subcutaneous, or topical application can include the following components: a sterile diluent such as water for injection saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions may also be pharmaceutically acceptable carriers. These may be prepared according to methods known to those skilled in the art, for example, as described in U.S. Pat. No. 4,522,811 ( which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

III. Biological Activity

A wide variety of biological assays have been used to evaluate the ability of a compound to act as a PAG receptor antagonist, including the ability of the compound to bind to PAF receptors, and the effect of the compound on various PAF mediated pathways. Any of these known assays can be used to evaluate the ability of the compounds disclosed herein to act as PAF receptor antagonists.

For example, PAF is known to induce hemoconcentration and increased permeability of microcirculation leading to a decrease in plasma volume. PAF mediated acute circulatory collapse can be used as the basis of an assay to evaluate the ability of a compound to act as a PAF antagonist, by analyzing the effect of the compound on PAF induced decreased plasma volume in an animal model such as mouse.

Endotoxemia causes the release of chemical mediators including eicosanoids, PAF, and tumor necrosis factor (TNF) that stimulate a variety of physiologic responses including fever, hypotension, leukocytosis, and disturbances in glucose and lipid metabolism. Endotoxemia can results in severe shock and death. Endotoxin-induced mouse mortality is a useful animal model to evaluate the pharmacological effect of compounds on endotoxic shock.

Two other common assays used to evaluate the ability of a compound to act as a PAF receptor antagonist are platelet aggregation in vitro and hypotension in rats (Shen, et al., "The Chemical and Biological Properties of PAF Agonists, Antagonists, and Biosynthetic Inhibitors", *Platelet-Activating Factor and Related Lipid Mediators*, F. Synder, Ed. Plenum Press, New York, N.Y. 153 (1987).)

A wide variety of biological assays have also been used to evaluate the ability of a compound to inhibit the enzyme b 5-lipoxygenase. For example, a cytosol 5-lipoxygenase of rat basophilic leukemia cells (RBL) has been widely utilized in studies on leukotriene biosynthesis. Compounds that inhibit 5-lipoxygenase decrease the levels of leukotrienes.

Another biological assay used to evaluate the ability of a compound to inhibit the enzyme 5-lipoxygenase is based on the classic pharmacological model of inflammation induced by the topical application of arachidonic acid to the mouse ear. On application, arachidonic acid is converted by 5-lipoxygenase to various leukotrienes (and other mediators), which induce changes in blood flow, erythema, and increase vasodilation and vasopermeability. The resulting edema is measured by comparing the thickness of the treated ear to a control ear. Agents that inhibit 5-lipoxygenase reduce the edematous response, by lowering the amounts of biochemical mediators formed from arachidonic acid.

2,5-Diaryl tetrahydrofurans and tetrahydrothiophenes disclosed herein were tested for their ability to act as PAF receptor antagonists and inhibit the enzyme 5-lipoxygenase, as described in detail below. The biological activity of other compounds within Formulas I, II, and III can be evaluated easily using the below-described assays or other assays known to those skilled in the art.

EXAMPLE 18

Ability of Compound to Bind to PAF Receptors a) Preparation of Human Platelet Membranes:

Human platelet membranes were prepared from platelet concentrates obtained from the American Red Cross Blood Services (Dedham, Mass.) After several washes with platelet wash solution (150 mM NaCl, 10 mM Tris, and 2 mM EDTA, pH 7.5), the platelet pellets were resuspended in 5 mM $MgCl_2$, 10 mM Tris, and 2 mM EDTA at pH 7.0. The cells were then quickly frozen with liquid nitrogen and thawed slowly at room temperature. The freezing and thawing procedure was repeated at least three times. For further fractionation of membrane fragments, the lysed membrane suspension was layered over the top of a discontinuous sucrose density gradient of 0.25, 1.03, and 1.5 M sucrose prepared in 10 mM $MgCl_2$, 10 mM Tris and 2 mM EDTA, pH 7.0, and centrifugated at 63,500×g for 2 hr. The membrane fractions banding between 0.25 and 1.03 M (membrane A) and between 1.03 and 1.5 M (membrane B) were collected separately. The protein concentration of the membrane preparations was determined by Lowry's method with bovine serum albumin (BSA) as the standard. The membranes were then separated into smaller fractions (4 ml each) and stored at −80° C. and thawed before use.

b) [$^3$H]PAF Binding inhibition:

The ability of [$^3$H]PAF to bind to specific receptors on human platelet (membranes was evaluated at optimal conditions at pH 7.0 and in the presence of 10 mM $MgCl_2$. Membrane protein (100 ug) was added to a final 0.5 ml solution containing 0.15 pmol (0.3 mM concentration) of [$^3$H]PAF and a known amount of unlabeled PAF or PAF receptor antagonist in 10 mM $MgCl_2$, 10 mM Tris and 0.25% BSA at pH 7.0. After incubation for four hours at 0° C., the bound and unbound [$^3$H]PAF were then separated through a Whatman (GF/C glass fiber under vacuum. No degradation of filter bound [$^3$H]PAF has been detected under this assay condition. The nonspecific binding was defined as the total binding in the presence of excess unlabeled PAF (1 mM) where no further displacement was found with higher concentrations of either unlabeled PAF or PAF analogs or PAF receptor antagonists. The specific binding was defined as the difference between total binding and nonspecific binding.

To determine the relative potency of tested compounds. [$^3$H]PAF binding in the presence of inhibitors was normalized in terms of percent inhibition by assigning the total binding in the absence of inhibitors as 0% inhibition and the total binding in the presence of 1 mM unlabeled PAF as 100%. The percent inhibition by the compound can be calculated by the formula expressed below:

% inhibition=[Total binding−total binding in the presence of compound)/nonspecific binding]×100%

The $IC_{50}$ was calculated as the concentration of the inhibitor necessary to obtain 50% inhibition of the specific [$^3$H]PAF binding and was calculated by a nonlinear regression computer software program. GraphPad Inplot, version 3.0 (GraphPad, software, San Diego, Calif.). Tables 1–4 provide the $IC_{50}$ values for a number of 2,5-diaryl tetrahydrothiophenes and tetrahydrofurans.

TABLE 1

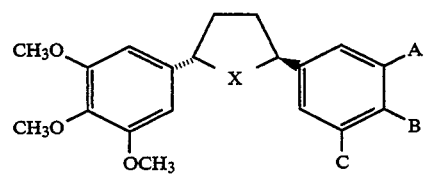

| Cmpd No | X | A | B | C | PAF $IC_{50}$ | *5-LO |
|---|---|---|---|---|---|---|
| 1 | S | $SCH_2CH_2NH_2$ | $OCH_3$ | $OCH_3$ | | 0.0% |
| 2 | S | $O_2CH_2CH_2NH_2$ | $OCH_3$ | $OCH_3$ | >1000 | |
| 3 | O | $HCH_2Ph$ | $OCH_2CH_2CH_3$ | $OCH_3$ | | 21.5% |
| 4 | O | $NHCH_2CH_2OH$ | $OCH_2CH_2CH_3$ | $OCH_3$ | 136 | 0.0% |
| 5 | O | $N(CH_2CH=CH_2)_2$ | $OCH_2CH_2CH_3$ | $OCH_3$ | 98 | 10.0 |
| 6 | S | $NHCH_2Ph$ | $OCH_3$ | $OCH_3$ | >1000 | 4.1% |
| 7 | S | $NHCH_2Ph$ | $OCH_2CH_2CH_3$ | $OCH_3$ | >1000 | 16.2% |
| 8 | S | $NHCH_2CH_2OH$ | $OCH_3$ | $OCH_3$ | 157 | 6.0% |
| 9 | S | $NCH_2CH_2OH_2$ | $OCH_2CH_2CH_3$ | $OCH_3$ | 91.5 | 18.8% |
| 10 | S | $N(CH_2CH=CH_2)_2$ | $OCH_3$ | $OCH_3$ | | |
| 11 | S | $N(CH_2CH=CH_2)_2$ | $OCH_2CH_2CH_3$ | $OCH_3$ | | |

*Inhibitions shown by percentage are at 10 μM

TABLE 2

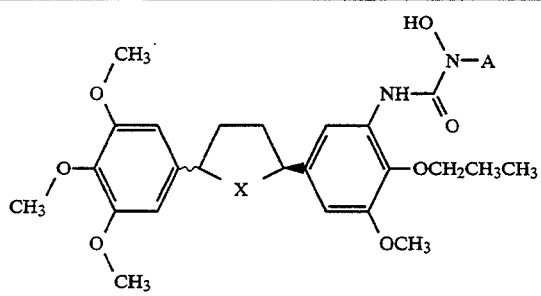

| No. | Isomer | X | A | IC$_{50}$ PAF (nM) | 5-LO IC$_{50}$ ($\mu$M) | 5-LO inhibition* |
|---|---|---|---|---|---|---|
| 12. | trans | O | H | 30 | | 22% |
| 13. | trans | O | CH$_3$ | 17 | 6.9 | |
| 38. | cis | O | CH$_3$CH$_2$ | 5.1 | 0.48 | |
| 14. | trans | O | CH(CH$_3$)$_2$ | 57 | | 40% |
| 39. | trans | O | CH$_3$(CH$_2$)$_3$ | 34.5 | 0.3 | |
| 15. | trans | O | C(CH$_3$)$_3$ | 25 | 2.9 | |
| 16. | trans | O | C$_6$H$_{11}$ | 278 | | 24% |
| 17. | trans | O | CH$_2\phi$ | 423 | 2.24 | |
| 18. | cis | O | H | 300 | | 28% |
| 19. | cis | O | CH$_3$ | 514 | | 56% |
| 40. | cis | O | CH$_3$CH$_2$ | 382 | 3 | |
| 20. | cis | O | CH(CH$_3$)$_2$ | 858 | 2.83 | |
| 41. | cis | O | CH$_3$(CH$_2$)$_3$ | 1313 | 0.5 | |
| 21. | cis | O | C(CH$_3$)$_3$ | 456 | | 54% |
| 22. | cis | O | C$_6$H$_{11}$ | >1000 | 2.5 | |
| 23. | cis | O | CH$_2\phi$ | 585 | 8 | |
| 24. | trans | S | H | 14 | 1 | |
| 25. | trans | S | CH$_3$ | 46 | 1 | |
| 26. | trans | S | CH(CH$_3$)$_2$ | 96.5 | 0.5 | |
| 27. | trans | S | C(CH$_3$)$_3$ | 46 | 0.5 | |
| 28. | cis | S | H | 496 | 3 | |
| 29. | cis | S | CH$_3$ | 300 | 0.64 | |
| 30. | cis | S | CH(CH$_3$)$_2$ | 828 | 2 | |
| 31. | cis | S | C(CH$_3$)$_3$ | 334 | 1.5 | |
| 32. | cis | S | C$_6$H$_{11}$ | 1287 | 2 | |

*All inhibitions shown by percentage are at 10 $\mu$M

TABLE 3

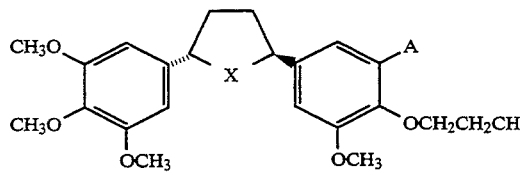

| Cmpd No | X | A | PAF IC$_{50}$ (nM) | IC$_{50}$ $\mu$M | 5-LO inhibition* |
|---|---|---|---|---|---|
| 33 | O | CH$_2$NHCONH(OH) | 280 | | 32.9% |
| 34 | O | CH$_2$NHCONCH$_3$(OH) | 16.7 | 1.6 | |
| 35 | O | CH$_2$NHCONi-Pr(OH) | 284 | 2.5 | |
| 36 | O | CH$_2$NHCONC$_6$H$_{11}$(OH) | 420 | 1.7 | |
| 37 | O | CH$_2$NHCOBn(OH) | 73.6 | 0.4 | |

*All inhibition shown in percentage is at 10 $\mu$M

TABLE 4

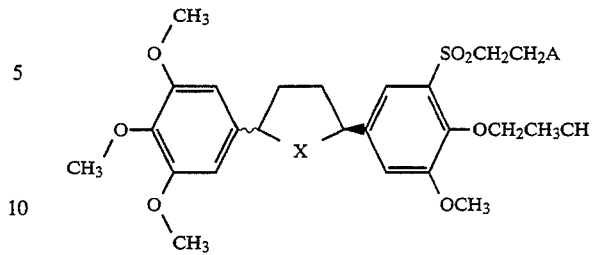

| No. | Isomer | X | A | PAF IC$_{50}$ (nM) | 5-LO inhibition* |
|---|---|---|---|---|---|
| 42. | trans | S | CH | 30 | 10.5% |

*Inhibition shown by percentage is at 10 $\mu$M

EXAMPLE 19

Effect of Compound on PAF-induced Hemoconcentration a) Animals

Female CD-1 mice, weighing 16–20 grams, were obtained from Charles River Laboratory (Wilmington, Mass.). Tap water and rodent laboratory chow (5001, Purina Mills, St. Louis, Mo.) were provided ad libitum. The mice were housed for an average of four days prior to use.

b) Hematocrit measurement

PAF (1-O-alkyl-2-acetyl-sn-glyceryl-3-phosphorylcholine, Sigma Chemical Co.) was dissolved in 0.25% bovine serum albumin (BSA) in 0.9% NaCl solution. Except for dose-response studies. 10 $\mu$g (10 ml/kg) of PAF solution was injected into the tail vein. All test compounds were dissolved in 0.5 DMSO saline solution and intravenously injected at 3 mg/kg body weight 15 minutes prior to PAF challenge. Thirty to fifty $\mu$l blood was collected by cutting the tail end into a heparinized micro-hematocrit tube (O.D. 1.50 mm) 15 minutes after PAF administration. Table 5 provides the mouse hematocrit response to varying concentration of PAF at 15 minutes after injection of PAF. Table 6 provides the effect of various test compounds on PAF-induced mouse hemoconcentration; the reference compound MK287 is trans-2-(3,4,5-trimethoxy)-5-(3-methyoxy-4-oxyallyl-(2-hydroxyethylsulfonyl))-tetrahydrofuran. (Sahoo, et al., Bioorganic Medicinal Chem. Letters, (1991), 1, 327).

TABLE 5

Mouse Hematocrit Response to Varying Concentration of PAF at 15 Minutes After Injection of PAF

| Doses of PAF (ug/kg) | Animal number | Hematocrit (%) | |
|---|---|---|---|
| | | Mean | SEM |
| 0 | 5 | 45.4 | 0.5 |
| 0.049 | 5 | 45.2 | 0.3 |
| 0.195 | 5 | 48.2 | 0.6 |
| 0.781 | 5 | 52.0 | 2.5 |
| 3.125 | 5 | 62.0 | 1.8 |
| 12.5 | 5 | 68.0 | 1.2 |
| 50 | 5 | 72.4 | 1.2 |
| 200 | 5 | 75.8 | 1.2 |

TABLE 6

Effect of Test Compounds on PAF-Induced Mouse Hemoconcentration

| Compound | Animal number | Hematocrit (%) Mean | SEM |
|---|---|---|---|
| Vehicle | 11 | 66.5 | 1.5 |
| Compound | | | |
| 42 | 5 | 45.2 | 0.6 |
| 14 | 5 | 54.4 | 2.4 |
| 12 | 5 | 61.1 | 1.2 |
| 13 | 5 | 62.3 | 2.1 |
| 15 | 5 | 64.6 | 1.5 |

EXAMPLE 20

Effect of 2,5-Diaryl Tetrahydrothiophenes and Tetrahydrofurans on Arachidonic Acid-induced Mouse Ear Edema a) Animals The animals were obtained and treated as in Example 16 above.

b) Edema measurement

Arachidonic acid was applied to both ears of mice in 0.025 ml of freshly prepared vehicle (acetone:pyridine:-water (97:2;1 v/v/v) and dried under a Sun-Lite Hitensity bulb. Except for dose-response studies, 0.5 mg of arachidonic acid was used for all applications. All test compounds were dissolved in 0.5% DMSO saline solution and intravenously injected at 3 mg/kg body weight 15 minutes prior to arachidonic acid treatment. Animals were sacrificed by cervical dislocations at 1 hours after topical application of arachidonic acid. A 7 mm-diameter disc of tissue was removed from each ear by means of a metal punch. Edema was measured by the average wet weight of the body ear tissues.

Table 7 provides out the mouse ear edematous responsive to varying concentrations of arachidonic acid at 1 hours after topical application. Table 8 provides the effect of various test compounds on arachidonic acid induced mouse ear edema.

TABLE 7

Mouse Ear Edema in Response to Varying Concentration of Arachidonic Acid at 1 Hour After Topical Application

| Doses of AA (mg/ear) | Ear number | Ear tissue weight (mg) Mean | SEM |
|---|---|---|---|
| 0 | 4 | 12.4 | 0.08 |
| 0.125 | 4 | 15.8 | 0.63 |
| 0.25 | 4 | 14.9 | 1.05 |
| 0.5 | 4 | 25.1 | 2.88 |
| 1.0 | 4 | 29.8 | 2.56 |
| 2.0 | 4 | 30.3 | 1.67 |

TABLE 8

Effect of Test Compounds on Arachidonic Acid-Induced Mouse Ear Edema

| Compound | Animal number | Inhibition (%) |
|---|---|---|
| 15 | 8 | 54.5 |
| 13 | 8 | 29.0 |
| 42 | 4 | 18.0 |

EXAMPLE 21

Effect of 2,5-Diaryl Tetrahydrothiophenes and Tetrahydrofurans on Endotoxin-induced Mouse Mortality a) Animals The mice were obtained and treated as in Example 16 above.

b) Mortality Measurement

Endotoxin (*E. coli* serotype 0127:B8, lipopolysaccharide, Sigma Chemical Co.) St. Louis, was freshly dissolved in 0.9% NaCl solution. Except for dose-response studies, endotoxin at 50 mg/kg was injected into the tail view. All test compounds were dissolved in 0.5% DMSO saline solution and intravenously injected at 3 mg/kg body weight 15 minutes prior to PAF challenge. Death occurred typically within 12–36 hours. Mortality was recorded 48 hours after endotoxin challenge, as death rarely occurred after 48 hr. The results of these evaluations are provided in Tables 9 and 10. Table 9 sets out the extent of mouse mortality in response to varying concentrations of endotoxin within 48 hours after intravenous injection of endotoxin is set out in Table 9. Table 10 provides the effect of test compounds on endotoxin-induced mouse mortality.

TABLE 9

Mouse Mortality in Response to Varying Concentration of Endotoxin Within 48 Hours After I.V. Injection of Endotoxin

| Doses of endotoxin (mg/kg) | Animal number | Survival (%) |
|---|---|---|
| 12.5 | 10 | 100 |
| 25 | 10 | 80 |
| 37.5 | 10 | 50 |
| 50 | 10 | 0 |
| 75 | 10 | 0 |

TABLE 10

Effect of Test Compounds on Endotoxin-Induced Mouse Mortality

| Compound | Animal number | Survival (%) |
|---|---|---|
| 13 | 6 | 83 |
| 15 | 5 | 17 |

EXAMPLE 22

Effect of Compounds on Cytosol 5-Lipoxygenase of Rate Basophile Leukemia Cells a) Enzyme preparation Washed rat RBL cells ($4 \times 10^8$) were suspended in 20 ml of 50 M potassium phosphate buffer at pH 7.4 containing 10% ethylene glycol/1 mM EDTA (Buffer A). The cell suspension was sonicated at 20 KHz for 30 seconds, and the sonicate was centrifuged at 10000 $\times$g for 10 minutes, followed by further centrifugation at 105000 $\times$g for 1 hr. The supernatant solution (cytosol fraction) containing 5-lipoxygenase was stored at $-70°$ C. Protein concentration was determined according to the procedure of Bradford (Bradford Dye Reagent) with bovine serum albumin as a standard.

b) Enzyme assay

For routine assay of 5-LO the mixture contained 50 mM potassium phosphate buffer at pH 7.4, 2 mM CaClhd 2, 2 mM ATP, 25 M arachidonic acid (0.1 Ci) and enzyme (50–100 mg of protein) in a final volume of 200 L. The reaction was carried out at 24° C. for 3 minutes. The mixture was extracted with 0.2 ml of an ice-cold mixture of ethyl ether:methanol:0.2 M citric acid (30:4:1). The extract was subjected to thin-layer chromatography at $-10°$ C. in a solvent system of petroleum ether:ethyl ether:acetic acid (15:85:0.1). The silica gel zones corresponding to authentic arachidonic acid and its metabolites were scrapped into scintillation vials for counting. The enzyme activity is expressed in terms of the amount of arachidonic acid oxygenated for 3 minutes.

Modifications and variations of the present invention relating to compounds that reduce the chemotaxis and respiratory burst leading to the formation of damaging oxygen radicals of PMNs during an inflammatory or immune response will be obvious to those skilled in the art from the foregoing detailed description of the invention. Such modifications and variations are intended to come within the scope of the appended claims.

We claim:

1. Compounds of the formula:

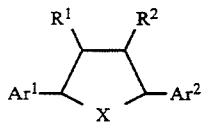

wherein:

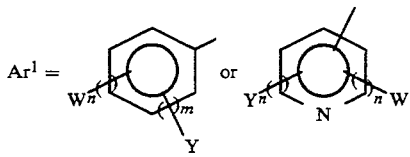

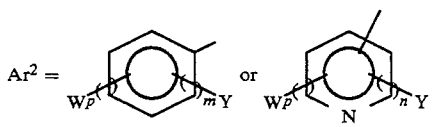

where
X is O, S, S(O), S(O)$_2$, CR$^9$, or NR$^{10}$;
W is independently —AN(OM)C(O)N(R$^3$)R$^4$, —AN(R$^3$)C(O)N(OM)R$^3$, —AN(OM)C(O)R$^4$, —AC(O)N(OM)R$^4$, —N(OM)C(O)N(R$^3$)R$^4$, —N(R$^3$)C(O)N(OM)R$^4$, —N(OM)C(O)R$^4$, —C(O)N(OM)R$^4$, —OR$^6$N(R$^5$)R$^6$—(C$_5$H$_4$N)R$^6$R$^7$, —OR$^6$N(COR$^5$)R$^6$—(C$_5$H$_4$N)R$^6$R$^7$, —OR$^6$OC(O)N(COR$^5$)R$^6$—(C$_5$H$_4$N)R$^6$R$^7$, —OR$^6$O(CO)N(CO$_2$R$^6$)R$^6$(C$_5$H$_4$N)R$^6$R$^7$, —A(C$_5$H$_4$N)R$^6$R$^7$;
n is 1 or 2;
m is 1, 2 or 3;
p is 0 or 1;
A is alkyl, alkenyl, alkynyl, alkyaryl, aralkyl, halo lower alkyl, halo lower alkyl, halo lower alkynyl, —C$^{1-10}$alkyl(oxy)C$^{1-10}$alkyl, —C$^{1-10}$alkyl((thio)C$^{1-10}$alkyl, —(R$^3$)C(O)alkyl, —N(R$^3$)C(O)alkenyl, —N(R$^3$)C(O)alkynyl, —N(R$^3$)C(O)(alkyl)oxy(alkyl), —N(R$^3$(C(O)(alkyl)thio(alkyl), —N(R$^3$)C(O)N(alkyl), —N(R$^3$)C(O)N(alkenyl), —N(R$^3$)C(O)N(alkynyl), —N(R$^3$)C(O)N(alkyl)oxy(alkyl), —N(R$^3$)C(O)N(alkyl)thio(alkyl), —N(R$^3$)C(O$_2$)alkyl, —N(R$^3$)C(O$_2$)alkenyl, —N(R$^3$)C(O$_2$)alkynl, —N(R$^3$)C(O$_2$)(alkyl)oxy(alkyl), —N(R$^3$)C(O$_2$)(alkyl)thio(alkyl) —OC(O$_2$)alkyl, —OC(O$_2$)alkenyl, —OC(O$_2$)alkynyl, —OC(O$_2$)(alkyl)oxy(alkyl), —OC(O$_2$)(alkyl)thio(alkyl), —N(R$^3$)C(S)alkyl, —N(R$^3$)C(S)alkenyl, —N(R$^3$)C(S)alkynyl, —N(R$^3$)C(S)alkyl)oxy(alkyl), —N(R$^3$)C(S)(alkyl)thio(alkyl), —N(R$^3$)C(S)N(alkyl), —N(R$^3$)C(S)N(alkenyl), —N(R$^3$)C(S)N(alkynyl), —N(R$^3$)C(S)N(alkyl)oxy(alkyl), —N(R$^3$)C(S)N(alkyl)thio(alkyl), —N(R$^3$)C(S)S(alkyl), —N(R$^3$)C(S)S(alkenyl), —N(R$^3$)C(S)S(alkynyl), —N(R$^3$)C(S)S(alkyl)oxy(alkyl), —N(R$^3$)C(S)S(alkyl)thio(alkyl), —SC(S)S(alkyl), —SC(S)S(alkenyl), —SC(S)S(alkynyl), —SC(S)S(alkyl)oxy(alkyl), and —SC(S)S(alkyl)thio(alkyl);

M is hydrogen, a pharmaceutically acceptable cation, or a metabolically cleavable leaving group;

Y is independently;
(a) hydrogen;
(b) R$^{1-6}$, R$^8$, R$^{10}$, —OR$^3$, —OR$^{11}$, —OR$^{12}$, R$^3$S—, R$^5$S, R$^3$SO—, R$^5$SO—, R$^3$SO$_2$—, R$^5$SO$_2$—, CF$_3$O—, CF$_3$S—, CF$_3$SO—, —CF$_3$SO$_2$, —OCH$_2$oxycyclopropyl, —OCH$_2$C(O)OR$^3$, —OCH$_2$OR$^3$—OCH$_2$C(O)R$^3$, —OCH$_2$C$_{3-8}$ cycloalkyl, —OCH$_2$CH(R)R$^3$, —OCH$_2$cyclopropyl, —OCH$_2$aryl, —OCH$_2$CH(OH)CH$_2$OH, aryl-CH$_2$—SO$_2$—, (R$^3$)$_2$CHCH$_2$SO$_2$—, —CH$_2$CH(OH)CH$_2$OH, CF$_3$SO$_2$—, R$^3$R$^4$N—, —OCH$_2$CO$_2$R$^3$, —NR$^3$COR$^3$, —OCONH$_2$, —COONR$^3$R$^4$, —CONH$_2$, —CONR$^3$R$^4$, —CR$^3$R$^3$R$^4$, —SO$_2$NR$^3$R$^4$, —SONR$^3$R$^4$, CH$_3$OCH$_2$ONR$^3$R$^6$, —SNR$^3$R$^4$, —CO$_2$R$^3$, —NR$^3$R$^4$SO$_2$R$^3$, —NR$^3$R$^4$SOR, —COR$^3$, —CONR$^3$, —NO$_2$, —CN, —N(R$^5$)CONR$^3$R$^4$, —CH$_2$N(R$^5$)CONR$^3$R$^4$, —R$^6$NR$^3$R$^4$, —OR$^6$NR$^3$R$^4$, —O(O)CR$^5$, —O(O)CNR$^3$R$^4$,

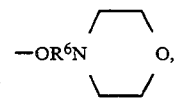

SR$^6$NR$^3$R$^4$, —S(O)R$^6$NR$^3$R$^4$, —SO$_2$R$^6$NR$^3$R$^4$,

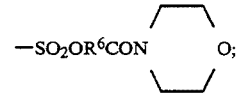

—SR$^6$OH; —S(O)R$^6$OH; —SO$_2$R$^6$OH; or —OR$^6$OC(O)N(CO$_2$R$^6$)R$^6$;

(c) pyridyl, and optionally substituted with a group described in Y section (b);

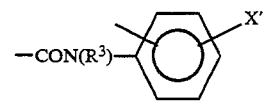

wherein X' is halo, —C(O)aryl, CF$_3$, or OR$^3$; —NR$_3$COR$^3$; —OCONH$_2$; —CR$^3$R$^3$R$^4$; —CH$_2$OR$^3$; —CH$_2$OR$^3$; —CH$_2$CO$_2$R$^3$; —CH$_2$OCOR$^3$; R$^3$CH(R$^3$)CH$_2$SO$_3$—; —NHCH$_2$COOR$^3$; halo such as F, Cl, Br and I; N+R$^3$R$^3$R$^4$R$^7$; —NR$^3$SO$_2$R$^3$; COR$^3$; NO$_2$: or CN;

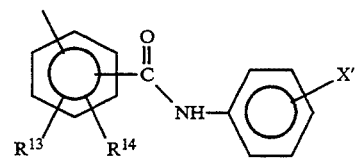

-continued

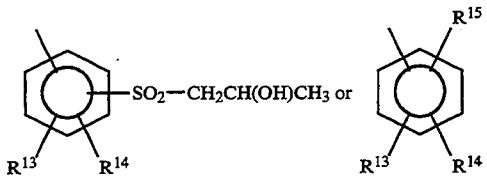

wherein $R^{13}$, $R^{14}$ and $R^{15}$ independently represents: BO— wherein B is —CH₂oxacyclopropyl, —CH₂OR³, —CH₂C(O)R³, —CH₂CH(R³)R³, —CH₂Aryl, —CH₂CH(OH)—CH₂OH; R³C(R³)₂CH₂SO₂; or $R^{13}$—$R^{14}$ or $R^{14}$—$R^{15}$ are joined together to form a bridge such as —OCHR²CHR²—S(O)ₙ— wherein n is 0 to 3; or

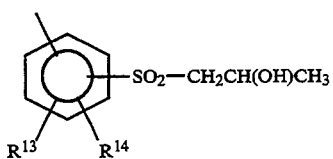

where X' is halo, —C(O)aryl, CF₃, or OR³; —CH₂OR³; —CH₂CO₂R³; —CH₂COR³; —NHCH₂COOR³; —N+R³R³R⁴R⁷.

$R^1$ and $R^2$ are independently hydrogen, halogen, or lower alkyl, halo lower alkyl, halo, —COOH; —CONR¹⁶R¹⁷ where $R^{16}$ and $R^{17}$ independently represent C₁₋₁₆ alkyl and hydrogen, —COOR³, alkenyl, —COR³; —CH₂OR³; lower alkynyl, CH₂NR⁴R³; —CH₂SR³=O; —OR³; or —NR³R³;

$R^3$ and $R^4$ are independently cyclic and acyclic alkyl, alkenyl, alkynyl, aryl, aralkyl, alkyaryl, hydrogen, C₁₋₆ alkoxy-C₁₋₁₀ alkyl, C₁₋₆ alkylthio-C₁₋₁₀ alkyl, and C₁₋₁₀ substituted alkyl (wherein the substituent is independently hydroxy or carbonyl, located on any of C₁₋₁₀);

$R^5$ is cyclic and acyclic lower alkyl, lower alkenyl, lower alkynyl, halo lower alkyl, halo lower alkenyl, halo lower alkynyl, aralkyl, or aryl;

$R^6$ is cyclic and acyclic lower alkyl, lower alkenyl, lower alkynyl, aralkyl, halo lower alkyl, halo lower alkenyl, halo lower alkynyl, or aryl;

$R^7$ is an organic or inorganic anion;

$R^8$ is halo alkyl, halo lower alkyl, halo lower alkenyl, halo lower alkynyl, lower alkenyl, lower alkynyl, aralkyl, or aryl;

$R^9$ is independently hydrogen, halogen, lower alkyl, halo lower alkyl, lower alkenyl, lower alkynyl, —CONR³R⁴, —COR⁵, —CO₂R⁵, —CH₂OR⁵, —CH₂NR⁵R⁵, —CH₂SR⁵, =O, =NR⁵, —NR³R⁴, —NR³R⁴§R⁷, or —OR⁵; and $R^{10}$ is —R³, —R⁸, —C(O)N(OR³)R³, or —OR³, $R^{11}$ is C₁ to C₁₂ alkyl; substituted C₁ to C₁₂ alkyl wherein the substituent is selected from the group consisting of hydroxy and amino, alkenyl, lower alkoxy-alkyl; alkylcarbonylalkyl, -alkylamino, -alkylamino(alkyl or dialkyl), lower alkyl S(O)ₘ- lower alkyl in which m is 0, 1 or 2; imidazolyl lower alkyl, morpholinyl lower alkyl, imidazolyl-carbonyl, morpholinyl carbonyl, morpholinyl (lower alkyl) aminocarbonyl, pyridylthio-lower alkyl; morpholinyl-lower alkyl; hydroxyphenylthio-lower alkyl; cyanophenylthio-lower alkyl; imidazolylthio-lower alkyl; N,N-di-substituted aminophenylthio-lower alkyl wherein the substituents each independently represent lower alkyl; aminophenylthio-lower alkyl; henylsulfinyl-lower alkyl; or phenylsulfonyl lower alkyl;

$R^{12}$ is selected from the group consisting of: alkyl; substituted alkyl wherein the substituent is selected from the group consisting of hydroxy and amino; -lower alkyl-O-R¹⁸, wherein $R^{18}$ is —PO₂(O-H)—M+ wherein M+ is a pharmaceutically acceptable cation; C(O)(CH₂)₂CO₂—M+, or —SO₃—M+; -lower alkylcarbonyl-lower alkyl; carboxy lower alkyl; -lower alkylamino-lower alkyl; N,N-di-substituted amino lower alkyl-, wherein the substituents each independently represent lower alkyl; pyridyl-lower alkyl; imidazoly-lower alkyl; imidazolyl-Y-lower alkyl wherein Y is thio or amino; morpholinyl-lower alkyl; morpholinyl-lower hydroxyalkyl; wherein the substituent is lower alkyl.

2. A compound of claim 1 of the formula:

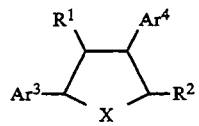

Ar³ and Ar⁴ are independently

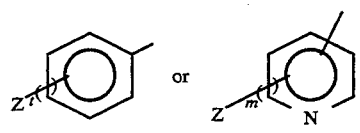

wherein:
X is O, S, S(O), S(O)₂, or NR¹⁰;
t is 1, 2, 3, or 4;
m is 1, 2, or 3.

3. A compound of claims 1 or 2 of the formula:

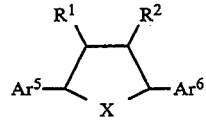

wherein Ar⁵ is:

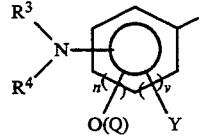

wherein Ar⁶ is:

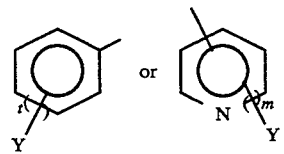

wherein:
v is 0, 1 or 2; and
Q is selected from the group consisting of substituted C₁ to C₁₂ alkyl wherein the substituent is selected from the group consisting of hydroxy and amino, alkylcarbonylalkyl, alkyl; lower alkyl S(O)$_m$-lower alkyl in which m is 1 or 2; imidazolyl lower alkyl, morpholinyl lower alkyl, imidazolylcarbonyl, morpholinyl carbonyl, morpholinyl (lower alkyl) aminocarbonyl, pyridylthio-lower alkyl; morpholinyl-lower alkyl; hydroxyphenylthio-lower alkyl; cyanophenylthio-lower alkyl; imidazolylthio-lower alkyl; aminophenylthio-lower alkyl; N,N-di-substituted aminophenylthio-lower alkyl wherein the amine substituents each independently represent lower alkyl amidinophenylthio-lower alkyl; phenylsulfinyl-lower alkyl; or phenylsulfonyl lower alkyl; —lower alkyl—O—R$^{18}$, wherein R$^{18}$ is —PO$_2$(OH)—M+ wherein M+ is a pharmaceutically acceptable cation; —C(O)(CH$_2$)$_2$CO$_2$—, M+, or —SO$_3$—M+; -lower alkylcarbonyl-lower alky; -carboxy lower alkyl; -lower alkylamino-lower alkyl; N,N-di-substituted amino lower alkyl-, wherein the substituents each independently represent lower alkyl; pyridyl-lower alkyl; imidazolyl-lower alkyl; imidazolyl-Y-lower alkyl wherein Y is thio or amino; morpholinyl-lower alkyl; morpholinyl-lower hydroxyalkyl; N-pyrryl; wherein the amine substituent is lower alkyl.

4. A pharmaceutical composition for the treatment of disorders mediated by platelet activating factor or products of 5-lipoxygenase, comprising an effective amount of a compound of claim 1.

5. A pharmaceutical composition for the treatment of disorders mediated by platelet activating factor or products of 5-lipoxygenase, comprising an effective amount of a compound of claim 2.

6. A pharmaceutical composition for the treatment of disorders by platelet activating factor or products of 5-lipoxygenase, comprising an effective amount of a compound of claim 3.

7. The compounds of claims 1 or 2 wherein X is O or S.

8. The compounds of claims 1 or 3 wherein W is —AN(OM)C(O)N(R$^2$)R$^4$.

9. The compounds of claims 1 or 2 wherein W is —AN(R$^3$)C(O)N(OM)R$^4$.

10. The compounds of claims 1 or 2 wherein W is —AC(O)N(OM)R$^4$.

11. The compounds of claims 1 or 2 wherein W is —N(R$^3$)C(O)N(OM)R$^4$.

12. The compounds of claims 1 or 2 wherein A is alkyl, alkenyl or alkynyl.

13. The compounds of claims 1 or 2 wherein A is —N(R$^3$)C(O)alkyl or —N(R$^3$)C(O)alkenyl.

14. The compounds of claims 1 or 2 wherein M is hydrogen or a pharmaceutically acceptable cation.

15. The compounds of claims 1 or 2 wherein M is a metabolically cleavable leaving group.

16. The compounds of claims 1 or 2 wherein Y is independently, —OR$^3$ or —OR$^{11}$.

17. The compounds of claims 1 or 2 wherein Y is R$^3$CO$_2$— or R$^3$R$^4$N.

18. The compounds of claims 1 or 2 wherein y is —CO$_2$R$^3$, —NO$_2$ or —CN.

19. The compounds of claims 1 or 2 wherein Y is —R$^6$NR$^3$R$^4$ or —SO$_2$R$^6$NR$^3$R$^4$.

20. The compounds of claims 1 or 2 wherein R$^1$ and R$^2$ are hydrogen.

21. The compounds of claims 1 or 2 wherein R$^3$ and R$^4$ are independently, cyclic and acyclic alkyl, alkenyl, alkynyl, aryl, aralkyl or hydrogen.

22. The compounds of claims 1 or 2 wherein R$^4$ is acyclic lower alkyl.

23. The compounds of claims 1 or 2 wherein R$^{11}$ is C$_1$-C$_{12}$ alkyl.

24. The compounds of claims 1 or 2 wherein R$^{11}$ is substituted C$_1$ to C$_{12}$ alkyl, wherein the substituent is selected from the group consisting of hydroxy, alkenyl, lower alkoxy-alkyl or lower alkyl.

25. The compounds of claims 1 or 2 wherein R$^{11}$ is substituted C$_1$ to C$_{12}$ alkyl, wherein the substituent is selected from the group consisting of S(O)$_m$-lower alkyl in which m is 0, 1 or 2, hydroxyphenylthio-lower alkyl, cyanophenylthio-lower alkyl.

* * * * *